US012741945B2

(12) United States Patent
Weeks et al.

(10) Patent No.: US 12,741,945 B2

(45) **Date of Patent: *Sep. 22, 2026**

(54) RNA-TARGETING LIGANDS, COMPOSITIONS THEREOF, AND METHODS OF MAKING AND USING THE SAME

(71) Applicant: THE UNIVERSITY OF NORTH CAROLINA AT CHAPEL HILL, Chapel Hill, NC (US)

(72) Inventors: Kevin Weeks, Carrboro, NC (US); Jeffrey Aubé, Chapel Hill, NC (US); Kelin Li, Chapel Hill, NC (US); Meredith Zeller, Durham, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 1228 days.

This patent is subject to a terminal disclaimer.

(21) Appl. No.: 17/632,695

(22) PCT Filed: Aug. 5, 2020

(86) PCT No.: PCT/US2020/045022

§ 371 (c)(1),
(2) Date: Feb. 3, 2022

(87) PCT Pub. No.: WO2021/026245

PCT Pub. Date: Feb. 11, 2021

(65) Prior Publication Data

US 2022/0289688 A1 Sep. 15, 2022

Related U.S. Application Data

(60) Provisional application No. 63/031,944, filed on May 29, 2020, provisional application No. 62/883,370, filed on Aug. 6, 2019.

(51) Int. Cl.

| | |
|---|---|
| ***C07D 241/42*** | (2006.01) |
| ***A61K 31/498*** | (2006.01) |
| ***A61K 47/00*** | (2006.01) |
| ***C07D 401/12*** | (2006.01) |

(52) U.S. Cl.

CPC .......... *C07D 241/42* (2013.01); *A61K 31/498* (2013.01); *A61K 47/00* (2013.01); *C07D 401/12* (2013.01)

(58) Field of Classification Search

CPC .. C07D 241/42; C07D 401/12; A61K 31/498; A61K 47/00

See application file for complete search history.

(56) References Cited

U.S. PATENT DOCUMENTS

| | | | | |
|---|---|---|---|---|
| 2005/0032805 A1 | 2/2005 | Jefferson et al. | | |
| 2011/0237549 A1 | 9/2011 | Patel et al. | | |
| 2016/0194317 A1 | 7/2016 | Agris | | |
| 2018/0148429 A1* | 5/2018 | Fabritius | .............. | C07D 403/04 |
| 2024/0254107 A1* | 8/2024 | Weeks | ................ | A61K 31/498 |

FOREIGN PATENT DOCUMENTS

| | | |
|---|---|---|
| CN | 103980195 A | 8/2014 |
| CN | 107635986 A | 1/2018 |
| CN | 111705090 A | 9/2020 |
| JP | 2003-029367 A | 1/2003 |
| JP | 2004-509941 A | 4/2004 |
| JP | 2004-532806 A | 10/2004 |
| JP | 2007-522233 A | 8/2007 |
| JP | 2008-508348 A | 3/2008 |
| JP | 2011-505379 A | 2/2011 |
| JP | 2016-147807 A | 8/2016 |
| JP | 7594303 B2 | 12/2024 |
| KR | 10-2024-0016993 A | 2/2024 |
| WO | 2005077938 A1 | 8/2005 |
| WO | 2008-047883 A1 | 4/2008 |
| WO | 2008061108 A2 | 5/2008 |
| WO | 2009073620 A2 | 6/2009 |
| WO | 2011078143 A1 | 6/2011 |
| WO | 2021-026245 A1 | 8/2011 |
| WO | 2011103557 A1 | 8/2011 |
| WO | 2013148228 A1 | 10/2013 |
| WO | 2016-180536 A1 | 11/2016 |
| WO | 201180536 A1 | 11/2016 |
| WO | 2017049409 A1 | 3/2017 |
| WO | 2019045824 A1 | 3/2019 |

(Continued)

OTHER PUBLICATIONS

Hajduk, P. J., Huth, J. R. & Tse, C. Predicting protein druggability. Drug Discov. Today 10, 1675-1682 (2005).

Vukovic, S. & Huggins, D. J. Quantitative metrics for drug-target ligandability. Drug Discov. Today 23, 1258-1266 (2018).

Batey, R. T., Rambo, R. P. & Doudna, J. A. Tertiary Motifs in RNA Structure and Folding. Angew. Chem. Int. Ed. 38, 2326-2343 (1999).

Warner, K. D., Hajdin, C. E. & Weeks, K. M. Principles for targeting RNA with drug-like small molecules. Nat. Rev. Drug Discov. 17, 547-558 (2018).

Sharp, P. A. The Centrality of RNA. Cell 136, 577-580 (2009).

Kozak, M. Regulation of translation via mRNA structure in prokaryotes and eukaryotes. Gene 361, 13-37 (2005).

Corbino, K. A., Sherlock, M. E., McCown, P. J., Breaker, R. R. & Stav, S. Riboswitch diversity and distribution. RNA 23, 995-1011 (2017).

(Continued)

*Primary Examiner* — James H Alstrum-Acevedo

*Assistant Examiner* — Carolyn L. Ladd

(74) *Attorney, Agent, or Firm* — Katten Muchin Rosenman LLP

(57) ABSTRACT

The disclosure is directed to compounds that bind to a target RNA molecule, such as a TPP riboswitch, compositions comprising the compounds, and methods of making and using the same. The compounds contain two structurally different fragments that allow for binding with the target RNA at two different binding sites thereby producing a higher affinity binding ligand compared to compounds that only bind to a single RNA binding site.

16 Claims, 9 Drawing Sheets

Specification includes a Sequence Listing.

(56) References Cited

FOREIGN PATENT DOCUMENTS

WO 2023-111686 A2 6/2023

OTHER PUBLICATIONS

Cech, T. R. & Steitz, J. A. The noncoding RNA revolution—Trashing old rules to forge new ones. Cell 157, 77-94 (2014).
Parsons, C., Slack, F. J., Zhang, W. C., Adams, B. D. & Walker, L. Targeting noncoding RNAs in disease. J. Clin. Invest. 127, 761-771 (2017).
Matsui, M. & Corey, D. R. Non-coding RNAs as drug targets. Nat. Rev. Drug Discov. 16, 167-179 (2017).
Guan, L. & Disney, M. D. Recent advances in developing small molecules targeting RNA. ACS Chem. Biol. 7, 73-86 (2012).
Connelly, C. M., Moon, M. H. & Schneekloth, J. S. The Emerging Role of RNA as a Therapeutic Target for Small Molecules. Cell Chem. Biol. 23, 1077-1090 (2016).
Murray, C. W. & Rees, D. C. The rise of fragment-based drug discovery. Nat. Chem. 1, 187-92 (2009).
Doak, B. C., Norton, R. S. & Scanlon, M. J. The ways and means of fragment-based drug design. Pharmacol. Ther. 167, 28-37 (2016).
Cressina, E., Chen, L., Abell, C., Leeper, F. J. & Smith, A. G. Fragment screening against the thiamine pyrophosphate riboswitch thiM. Chem. Sci. 2, 157-165 (2011).
Moumné, R., Catala, M., Larue, V., Micouin, L. & Tisné, C. Fragment-based design of small RNA binders: Promising developments and contribution of NMR. Biochimie 94, 1607-1619 (2012).
Warner, K. D. et al. Validating fragment-based drug discovery for biological RNAs: Lead fragments bind and remodel the TPP riboswitch specifically. Chem. Biol. 21, 591-595 (2014).
Zeiger, M. et al. Fragment based search for small molecule inhibitors of HIV-1 Tat-TAR. Bioorganic Med. Chem. Lett. 24, 5576-5580 (2014).
Bottini, A. et al. Targeting Influenza A Virus RNA Promoter. Chem. Biol. Drug Des. 86, 663-673 (2015).
Hunter, C. A. & Anderson, H. L. What is cooperativity? Angew. Chemie—Int. Ed. 48, 7488-7499 (2009).
Ichihara, O., Barker, J., Law, R. J. & Whittaker, M. Compound design by fragment-linking. Mol. Inform. 30, 298-306 (2011).
Zeller, M. J., Li, K., Aubé, J. & Weeks, K. M. Multisite ligand recognition and cooperativity in the TPP riboswitch RNA. Prep. (2019).
Siegfried, N. A., Busan, S., Rice, G. M., Nelson, J. A. E. & Weeks, K. M. RNA motif discovery by SHAPE and mutational profiling (SHAPE-MaP). Nat. Methods 11, 959-65 (2014).
Smola, M. J., Rice, G. M., Busan, S., Siegfried, N. A. & Weeks, K. M. Selective 2'-hydroxyl acylation analyzed by primer extension and mutational profiling (SHAPE-MaP) for direct, versatile and accurate RNA structure analysis. Nat. Protoc. 10, 1643-1669 (2015).
Merino, E. J., Wilkinson, K. A., Coughlan, J. L. & Weeks, K. M. RNA structure analysis at single nucleotide resolution by selective 2'-hydroxyl acylation and primer extension (SHAPE). J. Am. Chem. Soc. 127, 4223-4231 (2005).
Liu, Z.-Y. et al. Novel cis-acting element within the capsid-coding region enhances flavivirus viral-RNA replication by regulating genome cyclization. J. Virol. 87, 6804-18 (2013).
Serganov, A., Polonskaia, A., Phan, A. T., Breaker, R. R. & Patel, D. J. Structural basis for gene regulation by a thiamine pyrophosphate-sensing riboswitch. Nature 441, 1167-1171 (2006).
Edwards, T. E. & Ferré-D'Amaré, A. R. Crystal structures of the thi-box riboswitch bound to thiamine pyrophosphate analogs reveal adaptive RNA-small molecule recognition. Structure 14, 1459-68 (2006).
Thore, S., Frick, C. & Ban, N. Structural basis of thiamine pyrophosphate analogues binding to the eukaryotic riboswitch. J. Am. Chem. Soc. 130, 8116-8117 (2008).
Busan, S. & Weeks, K. M. Accurate detection of chemical modifications in RNA by mutational profiling (MaP) with ShapeMapper 2. RNA 24, 143-148 (2018).
Jhoti, H., Williams, G., Rees, D. C. & Murray, C. W. The 'rule of three' for fragment-based drug discovery: Where are we now? Nat. Rev. Drug Discov. 12, 644 (2013).
Chen, L. et al. Probing riboswitch-ligand interactions using thiamine pyrophosphate analogues. Org. Biomol. Chem. 10, 5924-5931 (2012).
Warner, K. D. & Ferré-D'Amaré, A. R. Crystallographic analysis of TPP riboswitch binding by small-molecule ligands discovered through fragment-based drug discovery approaches. Methods Enzymol. 549, 221-233 (2014).
Codd, R. Traversing the coordination chemistry and chemical biology of hydroxamic acids. Coord. Chem. Rev. 252, 1387-1408 (2008).
Jencks, W. P. On the attribution and additivity of binding energies. Proc. Natl. Acad. Sci. U. S. A. 78, 4046-4050 (1981).
Olejniczak, E. T. et al. Stromelysin inhibitors designed from weakly bound fragments: Effects of linking and cooperativity. J. Am. Chem. Soc. 119, 5828-5832 (1997).
Borsi, V., Calderone, V., Fragai, M., Luchinat, C. & Sarti, N. Entropic contribution to the linking coefficient in fragment based drug design: A case study. J. Med. Chem. 53, 4285-4289 (2010).
Reuter, J. S. & Mathews, D. H. RNAstructure: software for RNA secondary structure prediction and analysis. BMC Bioinformatics 11, 129 (2010).
Busan, S., Weidmann, C. A., Sengupta, A. & Weeks, K. M. Guidelines for SHAPE Reagent Choice and Detection Strategy for RNA Structure Probing Studies. Biochemistry 58, 2655-2664 (2019).
Gilbert, S. D. & Batey, R. T. Monitoring RNA-ligand interactions using isothermal titration calorimetry. Methods Mol. Biol. 540, 97-114 (2009).
Turnbull, W. B. Divided We Fall? Studying low affinity fragments of ligands by ITC. Microcal Application Notes (2005).
Otwinowski, Z. & Minor, W. Processing of X-ray diffraction data collected in oscillation mode. Methods Enzymol. (1997). doi:10.1016/S0076-6879(97)76066-X.
Liebschner, D. et al. Macromolecular structure determination using X-rays, neutrons and electrons: recent developments in Phenix. Acta Crystallogr. 75, 861-877 (2019).
Hajduk, P. J. et al. Discovery of potent nonpeptide inhibitors of stromelysin using SAR by NMR. J. Am. Chem. Soc. 119, 5818-5827 (1997).
Howard, N. et al. Application of fragment screening and fragment linking to the discovery of novel thrombin inhibitors. J. Med. Chem. 49, 1346-1355 (2006).
Barker, J. J. et al. Discovery of a novel Hsp90 inhibitor by fragment linking. ChemMedChem 5, 1697-1700 (2010).
Möbitz, H. et al. Discovery of Potent, Selective, and Structurally Novel Dot1L Inhibitors by a Fragment Linking Approach. ACS Med. Chem. Lett. 8, 338-343 (2017).
Hung, A. W. et al. Application of fragment growing and fragment linking to the discovery of inhibitors of *Mycobacterium tuberculosis* pantothenate synthetase. Angew. Chemie—Int. Ed. 48, 8452-8456 (2009).
Jordan, J. B. et al. Fragment-Linking Approach Using19F NMR Spectroscopy to Obtain Highly Potent and Selective Inhibitors of β-Secretase. J. Med. Chem. 59, 3732-3749 (2016).
Maly, D. J., Choong, I. C. & Ellman, J. A. Combinatorial target-guided ligand assembly: Identification of potent subtype-selective c-Src inhibitors. Proc. Natl. Acad. Sci. 97, 2419-2424 (2000).
Shuker, S. B., Hajduk, P. J., Meadows, R. P. & Fesik, S. W. Discovering High-Affinity Ligands for Proteins: SAR by NMR. Science (80-. ). 274, 1531-1534 (1996).
Mondal, M. et al. Fragment Linking and Optimization of Inhibitors of the Aspartic Protease Endothiapepsin: Fragment-Based Drug Design Facilitated by Dynamic Combinatorial Chemistry. Angew. Chemie—Int. Ed. 55, 9422-9426 (2016).
Swayze, E. E. et al. SAR by MS: A ligand based technique for drug lead discovery against structured RNA targets. J. Med. Chem. 45, 3816-3819 (2002).
Registry (STN) [online], Jul. 28, 2019, 1/124-124/124, [searched: Apr. 16, 2024], CAS Registry No. 2361843-5-3, 2348030-71-5, 2341683-75-6, 2341683-74-5, 2334929-63-2, 2330721-20-3, 2329356-91-2, 2327304-70-9.

(56) References Cited

OTHER PUBLICATIONS

Woolson, R. Statistical Methods for the Analysis of Biomedical Data. (John Wiley & Sons, 1987).
The extended European search report dated Feb. 13, 2023, from European Patent Application No. 20850365.6, 7 sheets.
Deigan Warner Katherine et al: "Validating Fragment-Based Drug Discovery for Biological RNAs: Lead Fragments Bind and Remodel the TPP Riboswitch Specifically", Chemistry & Biology, vol. 21, No. 5, May 1, 2014 (May 1, 2014), pp. 591-595, XP093020386, GB ISSN: 1074-5521, DOI: 10.1016/j.chembiol.2014.03.007 Retrieved from the Internet: URL:https://www.cell.com/ccbio/pdfExtended/S1074-5521(14)00113-6> *abstract; table 1*.
Maly D. J., et al.,. Combinatorial target-guided ligand assembly: Identification of potent subtype-selective c-Src inhibitors. Proc. Natl. Acad. Sci. 97, 2419-2424 (2000).
Shuker S. B., et al., Discovering High-Affinity Ligands for Proteins□: SAR by NMR. Science (80-. ). 274, 1531-1534 (1996).
Swaze E. E. et al. SAR by MS: A ligand based technique for drug lead discovery against structured RNA targets. J. Med. Chem. 45, 3816-3819 (2002).
Hajduk P. J., et al.. Predicting protein druggability. Drug Discov. Today 10, 1675-1682 (2005).
Vukovic, S. et al. D. J. Quantitative metrics for drug-target ligandability. Drug Discov. Today 23, 1258-1266 (2018).
Batey R. T., et al., J. A. Tertiary Motifs in RNA Structure and Folding. Angew. Chem. Int. Ed. 38, 2326-2343 (1999).
Warner, K. D., et al. Principles for targeting RNA with drug-like small molecules. Nat. Rev. Drug Discov. 17, 547-558 (2018).
Corbino, K. A., et al. Riboswitch diversity and distribution. RNA 23, 995-1011 (2017).
Cech T. R. et al. The noncoding RNA revolution—Trashing old rules to forge new ones. Cell 157, 77-94 (2014).
Parsons C., et al.. Targeting noncoding RNAs in disease. J. Clin. Invest. 127, 761-771 (2017).
Guan, L. et al. Recent advances in developing small molecules targeting RNA. ACS Chem. Biol. 7, 73-86 (2012).
Connelly C. M., et al., The Emerging Role of RNA as a Therapeutic Target for Small Molecules. Cell Chem. Biol. 23, 1077-1090 (2016).
Murray, C. W. et al.,The rise of fragment-based drug discovery. Nat. Chem. 1, 187-92 (2009).
Doak, B. C., et al.,The ways and means of fragment-based drug design. Pharmacol. Ther. 167, 28-37 (2016).
Cressina, E., et al., Fragment screening against the thiamine pyrophosphate riboswitch thiM. Chem. Sci. 2, 157-165 (2011).
Moumne, R.,et al., Fragment-based design of small RNA binders: Promising developments and contribution of NMR. Biochimie 94, 1607-1619 (2012).
Hunter, C. A. et al., What is cooperativity? Angew. Chemie—Int. Ed. 48, 7488-7499 (2009).
Ichihara O., et al., Compound design by fragment-linking. Mol. Inform. 30, 298-306 (2011).
Zeller, M. J., et al., Multisite ligand recognition and cooperativity in the TPP riboswitch RNA. Prep. (2019).
Siegfried N. A., et al., RNA motif discovery by SHAPE and mutational profiling (SHAPE-MaP). Nat. Methods 11, 959-65 (2014).
Smola, M. J., et al. Selective 2'-hydroxyl acylation analyzed by primer extension and mutational profiling (SHAPE-MaP) for direct, versatile and accurate RNA structure analysis. Nat. Protoc. 10, 1643-1669 (2015).
Merino E. J., et al., RNA structure analysis at single nucleotide resolution by selective 2'-hydroxyl acylation and primer extension (SHAPE). J. Am. Chem. Soc. 127, 4223-4231 (2005).
Serganov, A., et al., Structural basis for gene regulation by a thiamine pyrophosphate-sensing riboswitch. Nature 441, 1167-1171 (2006).
Edwards, T. E. et al.,. Crystal structures of the thi-box riboswitch bound to thiamine pyrophosphate analogs reveal adaptive RNA-small molecule recognition. Structure 14, 1459-68 (2006).
Thore S., Frick, et al., Structural basis of thiamine pyrophosphate analogues binding to the eukaryotic riboswitch. J. Am. Chem. Soc. 130, 8116-8117 (2008).
Busan, S. et. al., Accurate detection of chemical modifications in RNA by mutational profiling (MaP) with ShapeMapper 2. RNA 24, 143-148 (2018).
Woolsen, R. Statistical Methods for the Analysis of Biomedical Data. (John Wiley & Sons, 1987).
Jhoti H., et al.,. The 'rule of three' for fragment-based drug discovery: Where are we now? Nat. Rev. Drug Discov. 12, 644 (2013).
Warner, K. D. et al., Crystallographic analysis of TPP riboswitch binding by small-molecule ligands discovered through fragment-based drug discovery approaches. Methods Enzymol. 549, 221-233 (2014).
Borsi V., et al., Entropic contribution to the linking coefficient in fragment based drug design: A case study. J. Med. Chem. 53, 4285-4289 (2010).
Reuter J. S. et al.,RNA structure: software for RNA secondary structure prediction and analysis. BMC Bioinformatics 11, 129 (2010).
Busan, S.,et al., Guidelines for SHAPE Reagent Choice and Detection Strategy for RNA Structure Probing Studies. Biochemistry 58, 2655-2664 (2019).
Gilbert, S. D. et al.,. Monitoring RNA-ligand interactions using isothermal titration calorimetry. Methods Mol. Biol. 540, 97-114 (2009).
Otwinowski, Z. et al.,Processing of X-ray diffraction data collected in oscillation mode. Methods Enzymol. (1997). doi:10.1016/S0076-6879(97)76066-X.
Liedschner D. et al., Macromolecular structure determination using X-rays, neutrons and electrons: recent developments in Phenix. Acta Crystallogr. 75, 861-877 (2019).
CAS Registry No. 1269059-52-0.
CAS Registry No. 313658-28-5.

* cited by examiner 17, 5.0 μM
31, >10 mM
35, 260 μM
36, 47 μM
38, 10 μM
39, 68 μM
37, 625 nM
40, 10 μM GGUCGCGAGUAAUCGCGACCGCUGCAAGAGAUUGUAGCGUGGGCACUUCGGUGUCCACACGCGAAGGAAAC
CGCGUGUCAACUGUGCAACAGCUGACAAAGAGAUUCCUAAAACUCAGUACUCGGGGUGCCCUUCUGCGUGA
AGGCUGAGAAAUACCCGUAUCACCUGAUCUGGAUAAUGCCAGCGUAGGGAAGUGCUGGAUCCGGUUCGCCG
GAUCAAUCGGGCUUCGGUCCGGUUC

RNA-TARGETING LIGANDS, COMPOSITIONS THEREOF, AND METHODS OF MAKING AND USING THE SAME

CROSS-REFERENCE TO RELATED APPLICATIONS

The present application is a U.S. National Stage entry of International Application No. PCT/US2020/045022, filed Aug. 5, 2020, which claims priority to U.S. Provisional Patent Application Nos. 63/031,944, filed on May 29, 2020 and 62/883,370, filed on Aug. 6, 2019, wherein the entire contents of both application are incorporated herein by reference.

GOVERNMENT SUPPORT

This invention was made with government support under Grant Nos. GM098662 and AI068462 awarded by the National Institutes of Health (NIH). The government has certain rights in the invention.

FIELD OF INVENTION

The disclosure is directed to compounds that binds to a target RNA molecule, such as a TPP riboswitch, compositions comprising the compounds, and methods of making and using the same. The compounds contain two structurally different fragments that allow for binding with the target RNA at two different binding sites, thereby producing a higher affinity binding ligand compared to compounds that only bind to a single RNA binding site.

INCORPORATION-BY-REFERENCE OF SEQUENCE LISTING

The material in the accompanying sequence listing is hereby incorporated by reference in its entirety into this application. The accompanying file, named Sequence Listing 39397600002_ST25 was created on Aug. 5, 2020 and is 4 KB.

BACKGROUND

The vast majority of small-molecule ligands are primarily developed to manipulate biological systems by targeting proteins. Proteins have very complex three-dimensional structures, which are critical for them in order to function properly and which include clefts and pockets into which small-molecule ligands are able to bind[1,2]. The transcriptome—the set of all RNA molecules produced in an organism—also includes promising targets for studying and manipulating biological systems. For example, not only do RNA transcriptomes play an important role in mammalian systems, but they are also present in both bacteria and viruses and thus represent targets for small molecules to modulate gene expression.

Of note is that RNA can adopt three-dimensional structures of complexity rivaling that of proteins[3], a key feature needed for the development of highly selective ligands[4], and RNAs play pervasive roles in governing the behavior of biological systems[5]. Originally viewed as merely being a carrier of genetic information that exists solely to transmit a message for protein coding and guiding the process of protein biosynthesis, the modern view of RNA has evolved to encompass an expanded role, where a diverse range of RNA molecules are now understood to have broad and far-reaching roles in modulating gene expression and other biological processes by various mechanisms. Even a large number of newly discovered noncoding RNAs have been found to be associated with disease such as cancer and nontumorigenic diseases. Thus, the realization that RNAs contribute to disease states apart from coding for pathogenic proteins provides a wealth of previously unrecognized therapeutic targets.

However, even though it has been shown that small-molecule ligands can bind to mRNAs and have the potential to up- or down-regulate translation efficiency, thus tuning protein expression in cells[6,7], there are challenges involved in the identification of small-molecule RNA ligands that are not faced when targeting proteins[4,11,12]. That also includes the development of small-molecules directed to non-coding RNAs, which also represent a rich pool of targets[8-10]. Unfortunately, despite the development of various techniques for the analysis of RNA structure and discovery of new function, the ability to efficiently and rapidly identify or design inhibitors that bind to and perturb the function of RNA lags far behind. Thus, there is a great need in the art to develop new methods and technologies that allow for rapid and efficient identification of small-molecule ligands that target RNA molecules.

SUMMARY

As already mentioned above, the transcriptome represents an attractive but underutilized set of targets for small-molecule ligands. Small-molecule ligands (and ultimately drugs) targeted to messenger RNAs and to non-coding RNAs have the potential to modulate cell state and disease. In the current disclosure, fragment-based screening strategies using selective 2'-hydroxyl acylation analyzed by primer extension (SHAPE) and SHAPE-mutational profiling (MaP) RNA structure probing were employed to discover small-molecule fragments that bind a target RNA structure. In particular, fragments and cooperatively binding fragment pairs that bind to the TPP riboswitch with millimolar to micromolar affinities were identified. Structure-activity-relationship (SAR) studies were carried out in order to obtain information to efficiently design a linked fragment ligand that binds to the TPP riboswitch with high nanomolar affinity. Principles from the current disclosure are not meant to be limiting to the TPP riboswitch, but can also be broadly applicable to other target RNA structures, leveraging cooperativity and multisite binding to develop high-quality ligands for diverse RNA targets.

As such, one aspect of the presently disclosed subject matter is a compound with a structure of formula (I):

Formula (I)

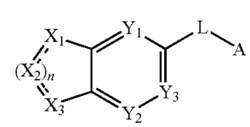

wherein $X_1$, $X_2$, and $X_3$ are, in each instance, independently selected from $CR_1$, $CHR_1$, N, NH, O and S, wherein adjacent $X_1$, $X_2$, and $X_3$ are not simultaneously selected to be O or S;

the dashed lines represent optional double bonds;

$Y_1$, $Y_2$, and $Y_3$ are, in each instance, independently selected from $CR_2$ and N;

n is 1 or 2, wherein when n is 1, only one of the dashed lines is a double bond;

L is selected from

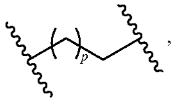
,
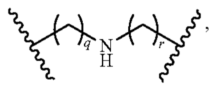
,
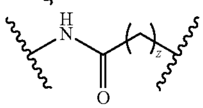
and
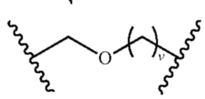
, wherein p, q, r, and v are independently selected from integers 0, 1, 2, 3, 4, 5, 6, 7, 8, 9, and 10, and z is selected from integers 1, 2, 3, 4, and 5; and A is selected from

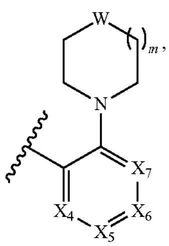
,
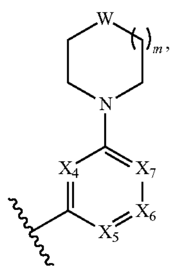
and
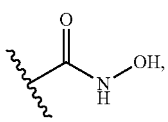
, wherein $X_4$, $X_5$, $X_6$, and $X_7$, are independently selected from $CR_3$ and N;

wherein $R_1$, $R_2$, and $R_3$ are independently selected from —H, —Cl, —Br, —I, —F, —$CF_3$, —OH, —CN, —$NO_2$, —$NH_2$, —NH($C_1$-$C_6$ alkyl), —N($C_1$-$C_6$ alkyl)$_2$, —COOH, —COO($C_1$-$C_6$ alkyl), —CO($C_1$-$C_6$ alkyl), —O($C_1$-$C_6$ alkyl), —OCO($C_1$-$C_6$ alkyl), —NCO($C_1$-$C_6$ alkyl), —CONH($C_1$-$C_6$ alkyl), and substituted or unsubstituted $C_1$-$C_6$ alkyl;

m is 1 or 2; and

W is —O or —$NR_4$, l wherein $R_4$ is selected from selected from —H, —CO($C_1$-$C_6$ alkyl), substituted or unsubstituted $C_1$-$C_6$ alkyl, substituted or unsubstituted aryl, substituted or unsubstituted heteroaryl, substituted or unsubstituted cycloalkyl, —CO(aryl), —CO(heteroaryl), and —CO(cycloalkyl);

provided that at least two of $X_1$, $X_2$, $X_3$, $X_4$, $X_5$, $X_6$, and $X_7$ are N;

or a pharmaceutically acceptable salt thereof.

A further aspect of the presently disclosed subject matter comprises a compound as described herein that binds to a region of an RNA molecule.

A further aspect of the presently disclosed subject matter comprises a composition comprising a therapeutically effective amount of a compound described herein in a pharmaceutically acceptable carrier, diluent, or excipient.

A further aspect of the presently disclosed subject matter comprises a method of treating a disease or disorder associated with a dysfunction in RNA expression, the method comprising administering to a subject in need thereof a dose of a therapeutically effective amount of a composition of a compound described herein.

A further aspect of the presently disclosed subject matter comprises methods for making the compounds described herein.

Still further aspects of the presently disclosed subject matter will be presented below.

BRIEF DESCRIPTION OF THE DRAWINGS

FIG. 4A shows a summary of binding by compound 2 (dark grey, $K_1$) and compound 31 (light grey, $K_2$) fragments. $K_D$ values determined by ITC. FIG. 4B shows ITC data showing single-compound and cooperative binding by fragments 2 and 31. Linking the two fragments shows an additive effect in binding energies, resulting in a sub-micromolar ligand, compound 37 ($K_1$). ITC traces are shown with background traces (ligand titrated into buffer) as light grey, experimental traces in dark gray. Curve fits are shown with the 95% confidence intervals in a grey shading.

FIG. 7A shows an RNA sequence (SEQ ID NO: 6) with the following components: GGUCGCGAGUAAUCGCGACC (SEQ ID NO: 7) is the structure cassette;

GCUGCAAGAGAUUGUAGC (SEQ ID NO: 8) is the RNA barcode (barcode NT underlined); GUGGGCACUUCGGUGUCCAC (SEQ ID NO: 9) is the structure cassette; ACGCGAAGGAAACCGCGUGUCAACUGUGCAACAGCUGACAAAGAGAUUCCU (SEQ ID NO: 10) is the DENV pseudoknot (mutations bold); AAAACU is the linker; CAGUACUCGGGGUGCCCUUCUGCGUGAAGGCUGAGAAAUACCCGUAUCACCUGA UCUGGAUAAUGCCAGCGUAGGGAAGUGCUG (SEQ ID NO: 11) is the TPP riboswitch (mutations bold); and GAUCCGGUUCGCCGGAUCAAUCGGGCUUCGGUCCGGUUC (SEQ ID NO: 12) is the structure cassette. FIG. 7B shows the secondary structure of the RNA-sequence barcode in the context of its self-folding hairpin.

DETAILED DESCRIPTION

Figure 1:
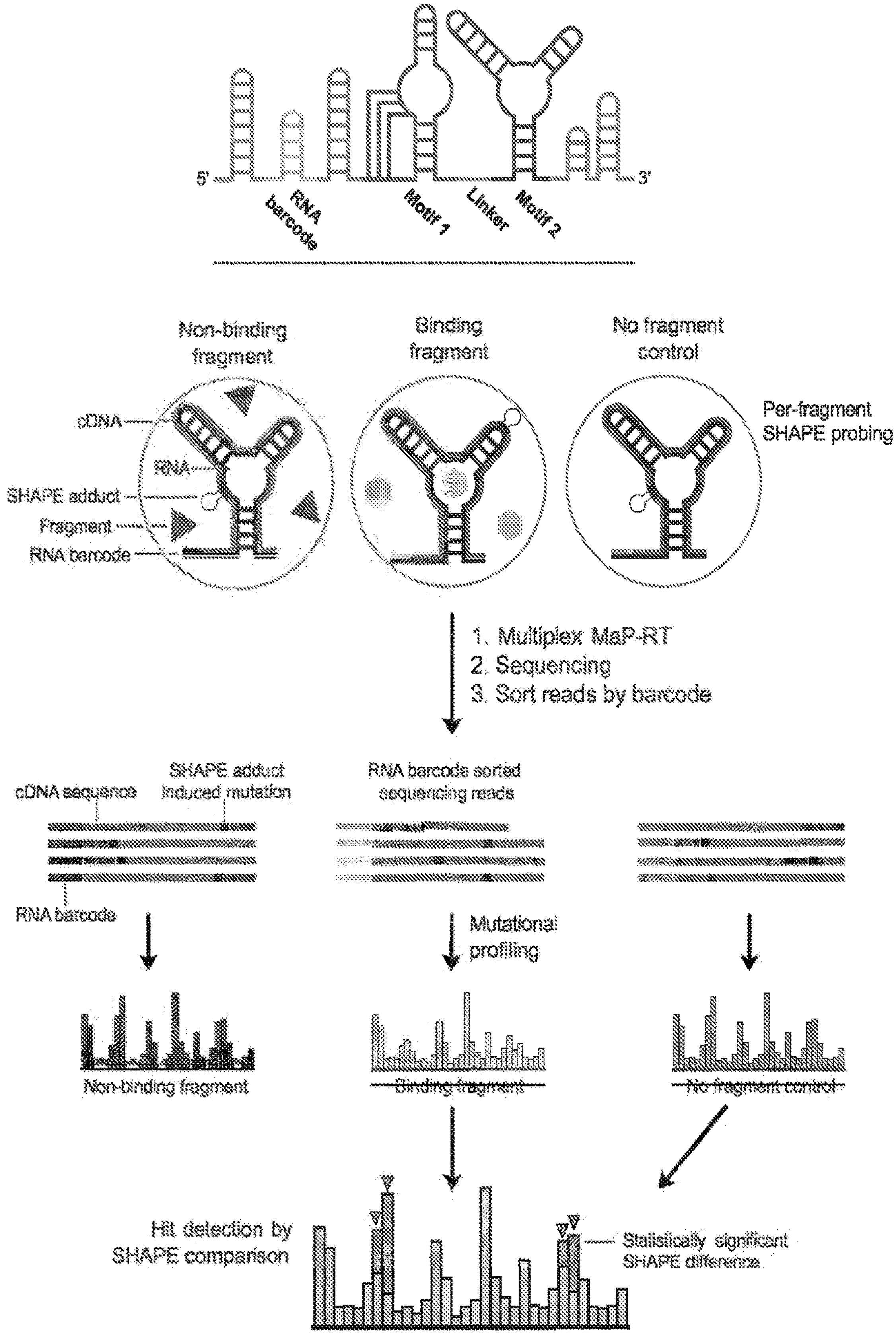
FIG. 1 shows schemes for RNA screening construct and fragment screening workflow. RNA motifs 1 and 2,the barcode helix, and the structure cassette helices are shown. RNA is probed using SHAPE in the presence or absence of a small-molecule fragment and the chemical modifications corresponding to ligand-dependent structural information are read out by multiplex MaP sequencing.

The presently disclosed subject matter will now be described more fully hereinafter. However, many modifications and other embodiments of the presently disclosed subject matter set forth herein will come to mind to one skilled in the art to which the presently disclosed subject matter pertains, having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

As used herein, the term "alkyl group" refers to a saturated hydrocarbon radical containing 1 to 8, 1 to 6, 1 to 4, or 5 to 8 carbons. In some embodiments, the saturated radical contains more than 8 carbons. An alkyl group is structurally similar to a noncyclic alkane compound modified by the removal of one hydrogen from the noncyclic alkane and the substitution therefore of a non-hydrogen group or radical. Alkyl group radicals can be branched or unbranched. Lower alkyl group radicals have 1 to 4 carbon atoms. Higher alkyl group radicals have 5 to 8 carbon atoms. Examples of alkyl, lower alkyl, and higher alkyl group radicals include, but are not limited to, methyl, ethyl, n-propyl, isopropyl, n-butyl, sec butyl, t butyl, amyl, t amyl, n-pentyl, n-hexyl, i-octyl and like radicals.

As used herein, the designations "(CO)" and "C(O)" are used to indicate a carbonyl moiety. Examples of suitable carbonyl moieties include, but are not limited to, ketone and aldehyde moieties.

The term "cycloalkyl" refers to a hydrocarbon with 3-8 members or 3-7 members or 3-6 members or 3-5 members or 3-4 members and can be monocyclic or bicyclic. The ring may be saturated or may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-10 membered ring systems where the heteroatoms are selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

As used herein, the term "substituted" refers to a moiety (such as heteroaryl, aryl, alkyl, and/or alkenyl) wherein the moiety is bonded to one or more additional organic or inorganic substituent radicals. In some embodiments, the substituted moiety comprises 1, 2, 3, 4, or 5 additional substituent groups or radicals. Suitable organic and inorganic substituent radicals include, but are not limited to, hydroxyl, cycloalkyl, aryl, substituted aryl, heteroaryl, heterocyclic ring, substituted heterocyclic ring, amino, mono-substituted amino, di-substituted amino, acyloxy, nitro, cyano, carboxy, carboalkoxy, alkyl carboxamide, substituted alkyl carboxamide, dialkyl carboxamide, substituted dialkyl carboxamide, alkylsulfonyl, alkylsulfinyl, thioalkyl, alkoxy, substituted alkoxy or haloalkoxy radicals, wherein the terms are defined herein. Unless otherwise indicated herein, the organic substituents can comprise from 1 to 4 or from 5 to 8 carbon atoms. When a substituted moiety is bonded thereon with more than one substituent radical, then the substituent radicals may be the same or different.

As used herein, the term "unsubstituted" refers to a moiety (such as heteroaryl, aryl, alkenyl, and/or alkyl) that is not bonded to one or more additional organic or inorganic substituent radical as described above, meaning that such a moiety is only substituted with hydrogens.

It will be understood that the structures provided herein and any recitation of "substitution" or "substituted with" includes the implicit proviso that such structures and substitution are in accordance with permitted valence of the substituted atom and the substituent, and that the substitution results in a stable compound, e.g., which does not spontaneously undergo transformation such as by rearrangement, cyclization, elimination, etc.

As used herein, the term "RNA" refers to a ribonucleic acid which is a polymeric molecule essential in various biological roles in coding, decoding, regulation and expression of genes. RNA and DNA are nucleic acids, and, along with lipids, proteins and carbohydrates, constitute the four major macromolecules essential for all known forms of life. Like DNA, RNA is assembled as a chain of nucleotides, but unlike DNA, RNA is found in nature as a single strand folded onto itself, rather than a paired double strand. Cellular organisms use messenger RNA (mRNA) to convey genetic information (using the nitrogenous bases of guanine, uracil, adenine, and cytosine, denoted by the letters G, U, A, and C) that directs synthesis of specific proteins. Many viruses encode their genetic information using an RNA genome. Some RNA molecules play an active role within cells by catalyzing biological reactions, controlling gene expression, or sensing and communicating responses to cellular signals. One of these active processes is protein synthesis, a universal function in which RNA molecules direct the synthesis of proteins on ribosomes. This process uses transfer RNA (tRNA) molecules to deliver amino acids to the ribosome, where ribosomal RNA (rRNA) then links amino acids together to form coded proteins.

As used herein, the term "non-coding RNA (ncRNA)" refers to an RNA molecule that is not translated into a protein. The DNA sequence from which a functional non-coding RNA is transcribed is often called an RNA gene. Abundant and functionally important types of non-coding RNAs include transfer RNAs (tRNAs) and ribosomal RNAs (rRNAs), as well as small RNAs such as microRNAs, siRNAs, piRNAs, snoRNAs, snRNAs, exRNAs, scaRNAs and the long ncRNAs such as Xist and HOTAIR.

As used herein, the term "coding RNA" refers to an RNA that codes for a protein, i.e., messenger RNS (mRNA). Such RNAs comprise a transcriptome.

As used herein, the term "riboswitch" refers to a regulatory segment of a messenger RNA molecule that binds a small molecule, resulting in a change in production of the protein encoded by the mRNA. Thus, an mRNA that contains a riboswitch is directly involved in regulating its own activity, in response to the concentrations of its effector molecule.

As used herein, the term "TPP riboswitch" also known as the THI element and Thi-box riboswitch, refers to a highly conserved RNA secondary structure. It serves as a riboswitch that binds directly to thiamine pyrophosphate (TPP) to regulate gene expression through a variety of mechanisms in archaea, bacteria and eukaryotes. TPP is the active form of thiamine (vitamin B1), an essential coenzyme synthesized by coupling of pyrimidine and thiazole moieties in bacteria.

As used herein, the term "pseudoknot" refers to a nucleic acid secondary structure containing at least two stem-loop structures in which half of one stem is intercalated between the two halves of another stem. The pseudoknot was first recognized in the turnip yellow mosaic virus in 1982. Pseudoknots fold into knot-shaped three-dimensional conformations but are not true topological knots.

An "aptamer" refers to a nucleic acid molecule that is capable of binding to a particular molecule of interest with high affinity and specificity (Tuerk and Gold, 1990; Ellington and Szostak, 1990), and can be of either human-engineered or natural origin. The binding of a ligand to an aptamer, which is typically RNA, changes the conformation of the aptamer and the nucleic acid within which the aptamer is located. In some instances, the conformation change inhibits translation of an mRNA in which the aptamer is located, for example, or otherwise interferes with the normal activity of the nucleic acid. Aptamers may also be composed of DNA or may comprise non-natural nucleotides and nucleotide analogs. An aptamer will most typically have been obtained by in vitro selection for binding of a target molecule. However, in vivo selection of an aptamer is also possible. Aptamer is also the ligand-binding domain of a riboswitch. An aptamer will typically be between about 10 and about 300 nucleotides in length. More commonly, an aptamer will be between about 30 and about 100 nucleotides in length. See, e.g., U.S. Pat. No. 6,949,379, incorporated herein by reference. Examples of aptamers that are useful for the present invention include, but are not limited to, PSMA aptamer (McNamara et al., 2006), CTLA4 aptamer (Santulli-Marotto et al., 2003) and 4-1BB aptamer (McNamara et al., 2007).

As used herein, the term "PCR" stands for polymerase chain reaction and refers to a method used widely in molecular biology to make millions to billions of copies of a specific DNA sample rapidly, allowing scientists to take a very small sample of DNA and amplify it to a large enough amount to study in detail.

The phrase "pharmaceutically acceptable" indicates that the substance or composition is compatible chemically and/or toxicologically, with the other ingredients comprising a formulation, and/or the subject being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions. Hence, a pharmaceutically acceptable salt can have one or more charged atoms and/or one or more counter ion.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. In certain embodiments, the pharmaceutically acceptable carrier is a non-naturally occurring pharmaceutically acceptable carrier.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented The term "administration" or "administering" includes routes of introducing the compound(s) to a subject to perform their intended function. Examples of routes of administration which can be used include injection (including, but not limited to, subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

The current disclosure is directed to a fragment-based ligand discovery strategy suited for the identification of small molecules that bind to specific RNA regions with high affinity. In general, fragment-based ligand discovery allows for the identification of one or more small-molecule "fragments" of low to moderate affinity that bind a target of interest. These fragments are then either elaborated or linked to create more potent ligands[13,14]. Typically, these fragments exhibit molecular masses of less than 300 Da and, in order to bind detectably, make substantial high-quality contacts with the target of interest.

Fragment-based ligand discovery has only so far been successfully employed to identify initial hit compounds that are single fragment hits binding for a given RNA[15-19]. Identification of multiple fragments that bind the same RNA would make it possible to take advantage of potential additive and cooperative interactions between fragments within the binding pocket[20,21]. However, it has recently been shown that many RNAs bind their ligands via multiple "sub-sites", which are regions of a binding pocket that contact a ligand in an independent or cooperative manner[22]. Further, it has been shown that high-affinity RNA binding can occur even when sub-site binding shows only modest cooperative effects. These features bode well for the effectiveness of fragment-based ligand discovery as applied to RNA targets.

Thus, based on the above, the current disclosure is directed to methods of identifying fragments that bind to an RNA of interest, such as for example the TPP riboswitch. Second, the disclosed methods are directed to establishing the positioning of fragment binding in the RNA at roughly nucleotide resolution. Third, the disclosed methods are directed to identifying second-site fragments that bound near the site of an initial fragment hit. The disclosed method melds the fragment-based ligand discovery approach with SHAPE-MaP RNA structure probing[23,24], which was used both to identify RNA-binding fragments and to establish the individual sites of fragment binding. The ligand ultimately created by linking two fragments has no resemblance to the native riboswitch ligand, and it binds the structurally complex TPP riboswitch RNA with high affinity.

The disclosed methods and the identification of ligands will be described in more detail below.

A. Compounds

A first aspect of the presently disclosed subject matter is a compound with a structure of formula (I):

Formula (I)

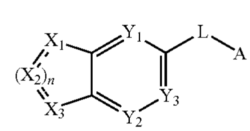

wherein $X_1$, $X_2$, and $X_3$ are, in each instance, independently selected from $CR_1$, $CHR_1$, N, NH, O and S, wherein adjacent $X_1$, $X_2$, and $X_3$ are not simultaneously selected to be O or S;

the dashed lines represent optional double bonds;

$Y_1$, $Y_2$, and $Y_3$ are, in each instance, independently selected from $CR_2$ and N;

n is 1 or 2, wherein when n is 1, only one of the dashed lines is a double bond;

L is selected from

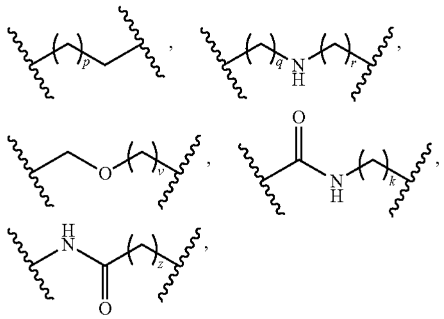

wherein k, p, q, r, and v are independently selected from integers 0, 1, 2, 3, 4, 5, 6, 7, 8, 9, and 10, z is selected from integers 1, 2, 3, 4, and 5; and A is selected from

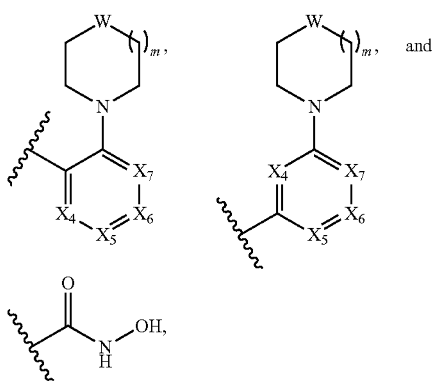

wherein $X_4$, $X_5$, $X_6$, and $X_7$, are independently selected from $CR_3$ and N;

wherein $R_1$, $R_2$, and $R_3$ are independently selected from —H, —Cl, —Br, —I, —F, —$CF_3$, —OH, —CN, —$NO_2$, —$NH_2$, —NH($C_1$-$C_6$ alkyl), —N($C_1$-$C_6$ alkyl)$_2$, —COON, —COO($C_1$-$C_6$ alkyl), —CO($C_1$-$C_6$ alkyl), —O($C_1$-$C_6$ alkyl), —OCO($C_1$-$C_6$ alkyl), —NCO($C_1$-$C_6$ alkyl), —CONH($C_1$-$C_6$ alkyl), and substituted or unsubstituted $C_1$-$C_6$ alkyl;

m is 1 or 2; and

W is —O or —$NR_4$, wherein $R_4$ is selected from selected from —H, —CO($C_1$-$C_6$ alkyl), substituted or unsubstituted $C_1$-$C_6$ alkyl, substituted or unsubstituted aryl, substituted or unsubstituted heteroaryl, substituted or unsubstituted cycloalkyl, —CO(aryl), —CO(heteroaryl), and —CO(cycloalkyl);

provided that at least two of $X_1$, $X_2$, $X_3$, $X_4$, $X_5$, $X_6$, and $X_7$ are N;

or a pharmaceutically acceptable salt thereof.

As in any above embodiment, a compound wherein at least one of $X_1$, $X_2$, or $X_3$ is N.

As in any above embodiment, a compound wherein $X_1$ is N.

As in any above embodiment, a compound wherein $X_2$ is N.

As in any above embodiment, a compound wherein $X_3$ is N.

As in any above embodiment, a compound wherein, in each instance, two of $X_1$, $X_2$, and $X_3$ are N.

As in any above embodiment, a compound wherein $X_1$ and $X_3$ are N.

As in any above embodiment, a compound wherein at least one of $Y_1$, $Y_2$, and $Y_3$ is N.

As in any above embodiment, a compound wherein $Y_1$ is N.

As in any above embodiment, a compound wherein $Y_2$ is N.

As in any above embodiment, a compound wherein $Y_3$ is N.

As in any above embodiment, a compound wherein at least one of $Y_1$, $Y_2$, and $Y_3$ is $CR_2$.

As in any above embodiment, a compound wherein $Y_1$ is $CR_2$.

As in any above embodiment, a compound wherein $Y_2$ is $CR_2$.

As in any above embodiment, a compound wherein $Y_3$ is $CR_2$.

As in any above embodiment, a compound wherein n is 2.

As in any above embodiment, a compound having the structure of formula (II):

Formula (II)

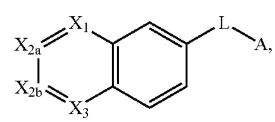

wherein $X_2$a and $X_2$b are independently selected from $CR_1$ and N;

$X_1$ and $X_3$ are independently selected from $CR_1$ and N;

L and A are as provided for Formula (I); and two of $X_1$, $X_{2a}$, $X_{2b}$, and $X_3$ are N.

As in any above embodiment, a compound having the structure of formula (III):

Formula (III)

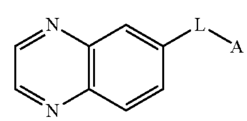

wherein

L and A are as provided for Formula (I).

As in any above embodiment, a compound wherein p, q, r, and v are independently selected from integers 0, 1, 2, and 3.

As in any above embodiment, a compound wherein L is selected from

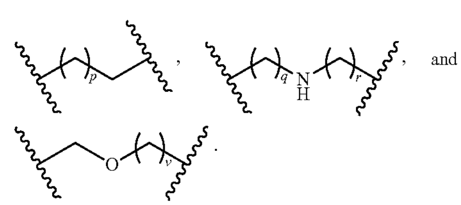

As in any above embodiment, a compound wherein L is

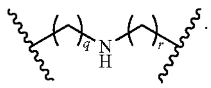

As in any above embodiment, a compound wherein q and r are 0 or 1.

As in any above embodiment, a compound wherein q is 1.

As in any above embodiment, a compound wherein r is 1.

As in any above embodiment, a compound wherein r is 0.

As in any above embodiment, a compound wherein q and r are 1.

As in any above embodiment, a compound wherein q is 1 and r is 0.

As in any above embodiment, a compound wherein m is 1.

As in any above embodiment, a compound wherein W is selected from —NH, —O, and —N($C_1$-$C_6$ alkyl)$_2$.

As in any above embodiment, a compound wherein W is —NH.

As in any above embodiment, a compound wherein at least one of $X_4$, $X_5$, $X_6$, and $X_7$ is N.

As in any above embodiment, a compound wherein $X_4$ is N.

As in any above embodiment, a compound wherein $X_5$ is N.

As in any above embodiment, a compound wherein $X_6$ is N.

As in any above embodiment, a compound wherein $X_7$ is N.

As in any above embodiment, a compound wherein $X_4$ and $X_6$ are N.

As in any above embodiment, a compound wherein $X_5$ and $X_7$ are N.

As in any above embodiment, a compound wherein $X_5$ or $X_6$ are N, and both $X_4$ and $X_7$ are independently $CR_2$.

As in any above embodiment, a compound wherein A is

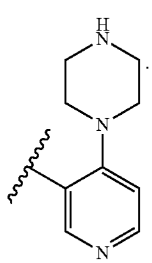

As in any above embodiment, a compound with the structure:

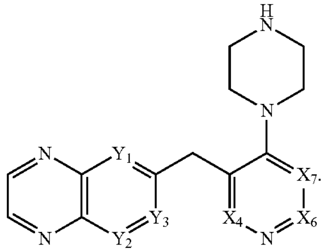

As in any above embodiment, a compound wherein L is

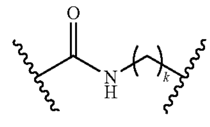

or

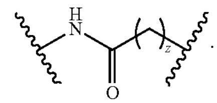

As in any above embodiment, a compound wherein $Y_1$, $Y_2$, and $Y_3$ are, in each instance, independently selected from $CR_2$ and N, wherein $R_1$ is selected from —H, —Cl, —Br, —I, —F, —OH, and —$NH_2$.

As in any above embodiment, a compound wherein z is 2.

As in any above embodiment, a compound wherein $Y_2$ is N.

As in any above embodiment, a compound wherein $Y_2$ is $CR_2$ and $R_1$ is selected from —H, —F, —OH, and —$NH_2$.

As in any above embodiment, a compound wherein A is

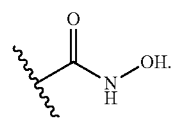 [SMILES: *C(=O)NO]

As in any above embodiment, a compound wherein said compound has the structure:

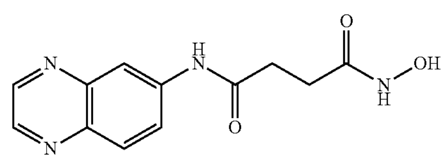

or

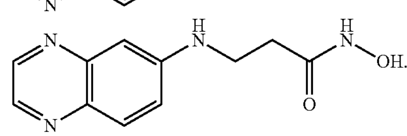

As in any above embodiment, a compound wherein said compound has the structure:

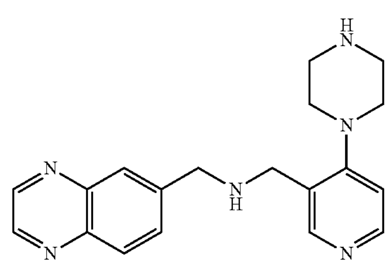

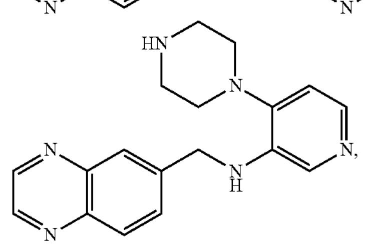

or

-continued

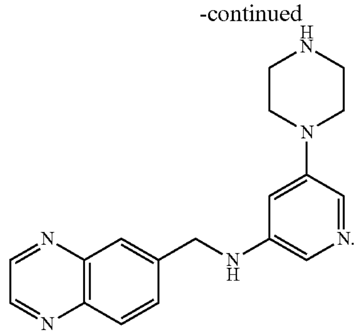

B. Screening Methods

The current disclosure is directed to the development and validation of a flexible selective 2'-hydroxyl acylation analyzed by primer extension (SHAPE)-based fragment screening method. Fragment-based ligand discovery has proven to be an effective approach for identifying compounds that form substantial intimate contacts with macromolecules, including RNA[13,14,17]. A prerequisite for success of this discovery strategy is an adaptable, high-quality biophysical assay to detect ligand binding. Thus, in some embodiments, SHAPE RNA structure probing was utilized to detect ligand binding[23-25], which measures local nucleotide flexibility as the relative reactivity of the ribose 2'-hydroxyl group toward electrophilic reagents. SHAPE can be used on any RNA and provides data on virtually all nucleotides in the RNA in a single experiment, yielding per-nucleotide structural information in addition to simply detecting binding, and is described in more detail below. In addition, the current disclosure is also directed towards applying SHAPE-mutational profiling (MaP)[23,24], which melds SHAPE with a readout by high-throughput sequencing, enabling multiplexing and efficient high-throughput analysis of many thousands of samples.

Thus, in some embodiments, the current disclosure is directed to a screening method utilizing SHAPE and/or SHAPE-MaP for identifying small-molecule fragments and/or compounds that bind to and/or associate with an RNA molecule of interest. The methods disclosed herein further comprise utilizing SHAPE and/or SHAPE-MaP for identifying small-molecule fragments (e.g., fragment 2) that bind to and/or associate with an RNA molecule that is already pre-incubated with another small-molecule fragment (e.g., fragment 1). Not to be bound by theory, but it is believed that fragment I binds to a first binding site and fragment 2 binds to a second binding site (e.g., sub-site) in the same RNA molecule. Thus, combining the structural features of fragment 1 and fragment 2 (e.g., connecting the two fragments with a linker L) to generate compounds as disclosed herein is thought to render linked fragment ligands of increased RNA binding affinity compared to fragment 1 and/or fragment 2 alone.

Screening methods SHAPE and SHAPE-MaP are described in more detail below.

I. SHAPE Chemistry

SHAPE chemistry is based at least in part on the observation that the nucleophilicity of the RNA ribose 2'-position is sensitive to the electronic influence of the adjacent 3'-phosphodiester group. Unconstrained nucleotides sample more conformations that enhance the nucleophilicity of the 2'-hydroxyl group than do base paired or otherwise constrained nucleotides. Therefore, hydroxyl-selective electrophiles, such as but not limited to N-methylisatoic anhydride (NMIA), form stable 2'-O-adducts more rapidly with flexible RNA nucleotides. Local nucleotide flexibility can be interrogated simultaneously at all positions in an RNA molecule in a single experiment because all RNA nucleotides (except a few cellular RNAs carrying post-transcriptional modifications) have a 2'-hydroxyl group. Absolute SHAPE reactivities can be compared across all positions in an RNA because 2'-hydroxyl reactivity is insensitive to base identity. It is also possible that a nucleotide can be reactive because it is constrained in a conformation that enhances the nucleophilicity of a specific 2'-hydroxyl. This class of nucleotide is expected to be rare, would involve a non-canonical local geometry, and would be scored correctly as an unpaired position.

The presently disclosed subject matter provides in some embodiments methods for detecting structural data in an RNA molecule by interrogating structural constraints in an RNA molecule of arbitrary length and structural complexity. In some embodiments, the methods comprise annealing an RNA molecule containing 2'-O-adducts with a (labeled) primer; annealing an RNA molecule containing no 2s-O-adducts with a (labeled) primer as a negative control; extending the primers to produce a library of cDNAs; analyzing the cDNAs; and producing output files comprising structural data for the RNA.

The RNA molecule can be present in a biological sample. In some embodiments, the RNA molecule can be modified in the presence of protein or other small and large biological ligands and/or compounds. The primers can optionally be labeled with radioisotopes, fluorescent labels, heavy atoms, enzymatic labels, a chemiluminescent group, a biotinyl group, a predetermined polypeptide epitope recognized by a secondary reporter, or combinations thereof. The analyzing can comprise separating, quantifying, sizing or combinations thereof. The analyzing can comprise extracting fluorescence or dye amount data as a function of elution time data, which are called traces. By way of example, the cDNAs can be analyzed in a single column of a capillary electrophoresis instrument or in a microfluidics device.

In some embodiments, peak area in traces for the RNA molecule containing 2'-O-adducts and for the RNA molecule containing no 2'-O-adducts versus nucleotide sequence can be calculated. The traces can be compared and aligned with the sequences of the RNAs. Traces observing and accounting for those cDNAs generated by sequencing are one nucleotide longer than corresponding positions in traces for the RNA containing 2'-O-adducts and for the RNA molecule containing no 2'-O-adducts. Areas under each peak can be determined by performing a whole trace Gaussian-fit integration.

Thus provided herein in some embodiments are methods for forming covalent ribose 2'-O-adducts with an RNA molecule in complex biological solutions. In some embodiments, the method comprises contacting an electrophile with an RNA molecule, wherein the electrophile selectively modifies unconstrained nucleotides in the RNA molecule to form covalent ribose 1'-O-adduct.

In some embodiments, an electrophile, such as but not limited to N-methylisatoic anhydride (NMIA), is dissolved in an anhydrous, polar, aprotic solvent such as DMSO. The reagent-solvent solution is added to a complex biological solution containing an RNA molecule. The solution can contain different concentrations and amounts of proteins, cells, viruses, lipids, mono- and polysaccharides, amino acids, nucleotides, DNA, and different salts and metabolites.

The concentration of the electrophile can be adjusted to achieve the desired degree of modification in the RNA molecule. The electrophile has the potential to react with all free hydroxyl groups in solution, producing ribose 2'-O-adducts on the RNA molecule. Further, the electrophile can selectively modify unpaired or otherwise unconstrained nucleotides in the RNA molecule.

The RNA molecule can be exposed to the electrophile at a concentration that yields sparse RNA modification to form 2'-O-adducts, which can be detected by the ability to inhibit primer extension by reverse transcriptase. All RNA sites can be interrogated in a single experiment because the chemistry targets the generic reactivity of the 2'-hydroxyl group. In some embodiments, a control extension reaction omitting the electrophile to assess background, as well as dideoxy sequencing extensions to assign nucleotide positions, can be performed in parallel. These combined steps are called selective 2'-hydroxyl acylation analyzed by primer extension, or SHAPE.

In some embodiments, the method further comprises contacting an RNA molecule containing 1'-O-adduct with a (labeled) primer, contacting an RNA containing no 2'-O-adduct with a (labeled) primer as a negative control; extending the primers to produce a linear array of cDNAs, analyzing the cDNAs, and producing output files comprising structural data of the RNA.

The number of nucleotides interrogated in a single SHAPE experiment depends not only on the detection and resolution of separation technology used, but also on the nature of RNA modification. Given reaction conditions, there is a length where nearly all RNA molecules have at least one modification. As primer extension reaches these lengths, the amount of extending cDNA decreases, which attenuates experimental signal. Adjusting conditions to decrease modification yield can increase read length. However, lowering reagent yield can also decrease the measured signal for each cDNA length. Given these considerations, a preferred maximum length of a single SHAPE read is probably about 1 kilobase of RNA, but should not be limited thereto.

II. SHAPE-MaP

In SHAPE-MaP, SHAPE adducts are detected by mutational profiling (MaP), which exploits an ability of reverse transcriptase enzymes to incorporate non-complementary nucleotides or create deletions at the sites of SHAPE chemical adducts. In some embodiments, SHAPE-MaP can be used in library construction and sequencing. In some embodiments, multiplexing techniques can be employed in SHAPE-MaP.

Typically, RNA is treated with a SHAPE reagent that reacts at conformationally dynamic nucleotides. During reverse transcription, the polymerase reads through chemical adducts in the RNA and incorporates a nucleotide non-complementary to the original sequence into the cDNA. The resulting cDNA is sequenced using any massively parallel approach to create mutational profiles (MaP). Sequencing reads are aligned to a reference sequence and nucleotide-resolution mutation rates are calculated, corrected for background and normalized producing a standard SHAPE reactivity profile. SHAPE reactivities can then be used to model secondary structures, visualize competing and alternative structures or quantify any process or function that modulates local nucleotide RNA dynamics. After SHAPE modification of the RNA molecule, reverse transcriptase is used to create a mutational profile. This step encodes the position and relative frequencies of SHAPE adducts as mutations in the cDNA. cDNA is converted to dsDNA using known methods in the art (e.g., PCR reaction) and dsDNA is further amplified in a second PCR reaction, thereby adding sequencing for multiplexing. After purification, sequencing libraries are of uniform size and each DNA molecule contains the entire sequence of interest.

Thus, in accordance with some embodiments of the presently disclosed subject matter, provided are methods for detecting one or more chemical modifications in a nucleic acid. In some embodiments, the method comprises providing a nucleic acid suspected of having a chemical modification; synthesizing a nucleic acid using a polymerase and the provided nucleic acid as a template, wherein the synthesizing occurs under conditions wherein the polymerase reads through a chemical modification in the provided nucleic acid to thereby produce an incorrect nucleotide in the resulting nucleic acid at the site of the chemical modification; and detecting the incorrect nucleotide.

In accordance with some embodiments of the presently disclosed subject matter, provided are methods for detecting structural data in a nucleic acid. In some embodiments, the method comprises providing a nucleic acid suspected of having a chemical modification; synthesizing a nucleic acid using a polymerase and the provided nucleic acid as a template, wherein the synthesizing occurs under conditions wherein the polymerase reads through a chemical modification in the provided nucleic acid to thereby produce an incorrect nucleotide in the resulting nucleic acid at the site of the chemical modification; detecting the incorrect nucleotide; and producing output files comprising structural data for the provided nucleic acid.

In some embodiments of the presently disclosed subject matter, the provided nucleic acid is an RNA molecule (e.g., a coding RNA and/or a non-coding RNA molecule). In some embodiments, the methods comprise detecting two or more chemical modifications. In some embodiments, the polymerase reads through multiple chemical modifications to produce multiple incorrect nucleotides and the methods comprise detecting each incorrect nucleotide.

In some embodiments, the nucleic acid (e.g., an RNA molecule) has been exposed to a reagent that provides a chemical modification or the chemical modification is preexisting in the nucleic acid (e.g., an RNA molecule). In some embodiments, the preexisting modification is a 2'-O-methyl group, and/or is created by a cell from which the nucleic acid is derived, such as but not limited to an epigenetic modification and/or the modification is 1-methyl adenosine, 3-methyl cytosine, 6-methyl adenosine, 3-methyl uridine, and/or 2-methyl guanosine. In some embodiments, the nucleic acids, such as an RNA molecule, can be modified in the presence of protein or other small and large biological ligands and/or compounds.

In some embodiments, the reagent comprises an electrophile. In some embodiments, the electrophile selectively modifies unconstrained nucleotides in the RNA molecule to form a covalent ribose 2'-O-adduct. In some embodiments, the reagent is 1 M7, 1 M6, NMIA, DMS, or combinations thereof. In some embodiments, the nucleic acid is present in or derived from a biological sample.

In some embodiments, the polymerase is a reverse transcriptase. In some embodiments, the polymerase is a native polymerase or a mutant polymerase. In some embodiments, the synthesized nucleic acid is a cDNA.

In some embodiments, detecting the incorrect nucleotide comprises sequencing the nucleic acid. In some embodiments, the sequence information is aligned with the sequence of the provided nucleic acid. In some embodiments, detecting the incorrect nucleotide comprises employing massively parallel sequencing on the nucleic acid. In some embodiments, the method comprises amplifying the nucleic acid. In some embodiments, the method comprises amplifying the nucleic acid using a site-directed approach using specific primers, whole-genome using random priming, whole-transcriptome using random priming, or combinations thereof.

In accordance with some embodiments of the presently disclosed subject matter, provided are computer program products comprising computer executable instructions embodied in a computer readable medium in performing steps comprising any method step of any embodiment of the presently disclosed subject matter. In accordance with some embodiments of the presently disclosed subject matter provided are nucleic acid libraries produced by any method of the presently disclosed subject matter.

III. SHAPE Electrophiles

As disclosed hereinabove, SHAPE chemistry takes advantage of the discovery that the nucleophilic reactivity of a ribose 2'-hydroxyl group is gated by local nucleotide flexibility. At nucleotides constrained by base pairing or tertiary interactions, the 3'-phosphodiester anion and other interactions reduce reactivity of the 2'-hydroxyl. In contrast, flexible positions preferentially adopt conformations that react with an electrophile, including but not limited to NMIA, to form a 2'-O-adduct. By way of example, NMIA reacts generically with all four nucleotides and the reagent undergoes a parallel, self-inactivating, hydrolysis reaction. Indeed, the presently disclosed subject matter provides that any molecule that can react with a nucleic acid as disclosed herein can be employed in accordance with some embodiments of the presently disclosed subject matter. In some embodiments, the electrophile (also referred to as the SHAPE reagent) can be selected from, but is not limited to, an isatoic anhydride derivative, a benzoyl cyanide derivative, a benzoyl chloride derivative, a phthalic anhydride derivative, a benzyl isocyanate derivative, and combinations thereof. The isatoic anhydride derivative can comprise 1-methyl-7-nitroisatoic anhydride (1M7). The benzoyl cyanide derivative can be selected from the group including but not limited to benzoyl cyanide (BC), 3-carboxybenzoyl cyanide (3-CBC), 4-carboxybenzoyl cyanide (4-CBC), 3-aminomethylbenzoyl cyanide (3-AMBC), 4-aminomethylbenzoyl cyanide, and combinations thereof. The benzoyl chloride derivative can comprise benzoyl chloride (BCD. The phthalic anhydride derivative can comprise 4-nitrophthalic anhydride (4NPA). The benzyl isocyanate derivative can comprise benzyl isocyanate (BIC).

IV. RNA Molecular Design

Because SHAPE reactivities can be assessed in one or more primer extension reactions, information can be lost at both the 5' end and near the primer binding site of an RNA molecule. Typically, adduct formation at the 10-20 nucleotides adjacent to the primer binding site is difficult to quantify due to the presence of cDNA fragments that reflect pausing or non-templated extension by the reverse transcriptase (RT) enzyme during the initiation phase of primer extension. The 8-10 positions at the 5' end of the RNA can be difficult to visualize due to the presence of an abundant full-length extension product.

To monitor SHAPE reactivities at the 5' and 3' ends of a sequence of interest, the RNA molecule can be embedded within a larger fragment of the native sequence or placed between strongly folding RNA sequences that contain a unique primer binding site. In some embodiments, a structure cassette can be designed that contains 5' and 3' flanking sequences of nucleotides to allow all positions within the RNA molecule of interest to be evaluated in any separation technique affording nucleotide resolution, such as but not limited to a sequencing gel, capillary electrophoresis, and the like. In some embodiments, both 5' and 3' extensions can fold into stable hairpin structures that do not to interfere with folding of diverse internal RNAs. The primer binding site of the cassette can efficiently bind to a cDNA primer. The sequence of any 5' and 3' structure cassette elements can be checked to ensure that they are not prone to forming stable base pairing interactions with the internal sequence.

In some embodiments, the RNA molecule of interest comprises two different target motifs that are connected with a nucleotide linker. A target motif can be any nucleotide sequence of interest. Exemplary target motifs include, but are not limited to, riboswitches, viral regulatory elements, structured regions in mRNAs, multi-helix junctions, pseudoknots and/or aptamers. In some embodiments, the first target motif is a pseudoknot, such as a pseudoknot from the 5'UTR of the dengue virus genome. In some embodiments, the second target motif is an aptamer domain, such as a TPP riboswitch aptamer domain. For the nucleotide linker, the number of nucleotides can vary. For example, in some embodiments, the number of nucleotides in the linker ranges from about 1 to about 20 nucleotides, about 1 to about 15 nucleotides, from about 1 to about10 nucleotides, or from about 5 to about 10 nucleotides (or is about 1, 2, 3, 4, 5, 6, 7, 8, 9, 10 nucleotides).

In some embodiments, the RNA molecule further comprises an RNA barcode region. The RNA barcode region is a unique barcode that allows for identification of a particular RNA molecule in a mixture of RNA molecules (e.g., during multiplexing). The location of the RNA barcode region can vary but is typically found adjacent to one of the cassettes present in the RNA molecule. In some embodiments, the RNA barcode is designed to fold into a self-contained structure that does not interact with any other part of the RNA molecule. The structure of the RNA barcode region can vary. In some embodiments, the structure of the RNA barcode region comprises a base pair helix comprising about 1 to about 10 base pairs (or about 1, 2, 3, 4, 5, 6, 7, 8, 9 or 10 base pairs). In some embodiments, the RNA barcode region comprises 7 base pairs. In some embodiments, the base pairs are capped with a tetraloop anchored to an end base pair of the base pair helix. Capping of the base pair helix maintains the overall hairpin stability of the RNA barcode region. In some embodiments, the tetraloop comprises nucleotide sequence GNRA but is not meant to be limited thereto. In some embodiments, the RNA barcode region is designed such that any individual barcode undergoes at least two mutations to be misconstrued as another barcode.

V. Folding of RNA Molecule

The presently disclosed subject matter can be performed with RNA molecules generated by methods including but not limited to in vitro transcription and RNA molecules generated in cells and viruses. In some embodiments, the RNA molecules can be purified by denaturing gel electrophoresis and renatured to achieve a biologically relevant conformation. Further, any procedure that folds the RNA molecules to a desired conformation at a desired pH (e.g., about pH 8) can be substituted. The RNA molecules can be first heated and snap cooled in a low ionic strength buffer to eliminate multimeric forms. A folding solution can then be added to allow the RNA molecules to achieve an appropriate conformation and to prepare it for structure-sensitive probing with an electrophile. In some embodiments, the RNA can be folded in a single reaction and later separated into (+)

and (−) electrophile reactions. In some embodiments, the RNA molecule is not natively folded before modification. Modification can take place while the RNA molecule is denatured by heat and/or low salt conditions.

VI. RNA Molecule Modification

The electrophile can be added to the RNA to yield 2'-O-adducts at flexible nucleotide positions. The reaction can then be incubated until essentially all of the electrophile has either reacted with the RNA or has degraded due to hydrolysis with water. No specific quench step is required. Modification can take place in the presence of complex ligands and biomolecules as well as in the presence of a variety of salts. RNA may be modified within cells and viruses as well. These salts and complex ligands may include salts of magnesium, sodium, manganese, iron, and/or cobalt. Complex ligands may include but are not limited to proteins, lipids, other RNA molecules, DNA, or small organic molecules. In some embodiments, the complex ligand is a small-molecule fragment as disclosed herein. In some embodiments, the complex ligand is a compound as disclosed herein. The modified RNA can be purified from reaction products and buffer components that can be detrimental to the primer extension reaction by, for example, ethanol precipitation.

VII. Primer Extension and Polymerization

Analysis of RNA adducts by primer extension in accordance with the presently disclosed subject matter can include in various embodiments the use of an optimized primer binding site, thermostable reverse transcriptase enzyme, low $MgCl_2$ concentration, elevated temperature, short extension times, and combinations of any of the forgoing. Intact, non-degraded RNA, free of reaction by-products and other small molecule contaminants can also be used as a template for reverse transcription. The RNA component of the resulting RNA-cDNA hybrids can be degraded by treatment with base. The cDNA fragments can then be resolved using, for example, a polyacrylamide sequencing gel, capillary electrophoresis or other separation technique as would be apparent to one of ordinary skill in the art after a review of the instant disclosure.

The deoxyribonucleotide triphosphates dATP, dCTP, dGTP, and dTTP and/or deoxyribonucleotide triphosphate (dNTP) can be added to the synthesis mixture, either separately or together with the primers, in adequate amounts and the resulting solution can be heated to about 50-100° C. from about 1 to 10 minutes. After the heating period, the solution can be cooled. In some embodiments, an appropriate agent for effecting the primer extension reaction can be added to the cooled mixture, and the reaction allowed to occur under conditions known in the art. In some embodiments, the agent for polymerization can be added together with the other reagents if heat stable. In some embodiments, the synthesis (or amplification) reaction can occur at room temperature. In some embodiments, the synthesis (or amplification) reaction can occur up to a temperature above which the agent for polymerization no longer functions.

The agent for polymerization can be any compound or system that functions to accomplish the synthesis of primer extension products, including, for example, enzymes. Suitable enzymes for this purpose include, but are not limited to, *E. coli* DNA polymerase I, Klenow fragment of *E. coli* DNA polymerase, polymerase muteins, reverse transcriptase, and other enzymes, including heat-stable enzymes (i.e., those enzymes that perform primer extension after being subjected to temperatures sufficiently elevated to cause denaturation), such as murine or avian reverse transcriptase enzymes. Suitable enzymes can facilitate combination of the nucleotides in the proper manner to form the primer extension products that are complementary to each polymorphic locus nucleic acid strand. In some embodiments, synthesis can be initiated at the 5' end of each primer and proceed in the 3' direction, until synthesis terminates at the end of the template, by incorporation of a dideoxynucleotide triphosphate, or at a 2'-O-adduct, producing molecules of different lengths.

The newly synthesized strand and its complementary nucleic acid strand can form a double-stranded molecule under hybridizing conditions described herein and this hybrid is used in subsequent steps as is disclosed methods described in U.S. Pat. Nos. 10,240,188 and 8,318,424, which are referenced herein in their entireties. In some embodiments, the newly synthesized double-stranded molecule can also be subjected to denaturing conditions using any of the procedures known in the art to provide single-stranded molecules.

VII. Processing of Raw Data

The subject matter described herein for nucleic acid, such as RNA molecules, chemical modification analysis and/or nucleic acid structure analysis can be implemented using a computer program product comprising computer executable instructions embodied in a computer-readable medium. Exemplary computer-readable media suitable for implementing the subject matter described herein include chip memory devices, disc memory devices, programmable logic devices, and application specific integrated circuits. In addition, a computer program product that implements the subject matter described herein can be located on a single device or computing platform or can be distributed across multiple devices or computing platforms. Thus, the subject matter described herein can include a set of computer instructions, that, when executed by a computer, performs a specific function for nucleic acid, such as RNA structure analysis.

Figures 7A, 7B:
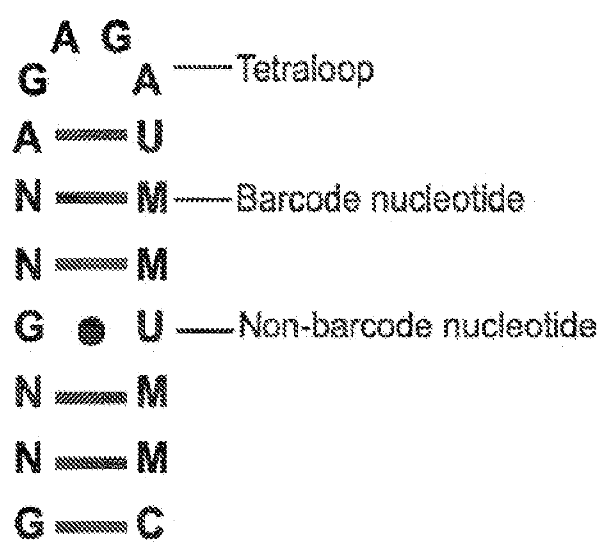
FIGS. 7A and 7B show screening construct design.

Taking into account items I-VII mentioned above, a modular RNA screening construct was designed to implement SHAPE as a high-throughput assay for readout of ligand binding (FIG. 1, top). The construct was designed to contain two target motifs, such as a pseudoknot from the 5'UTR of the dengue virus genome that reduces viral fitness when its structure is disrupted[26] and a TPP riboswitch aptamer domain[27-29]. Including two distinct structural motifs in a single construct allowed each to serve as an internal specificity control for the other. Fragments that bound to both RNA structures were easily identified as nonspecific binders. These two structures were connected by a six-nucleotide linker, designed to be single-stranded, to allow the two RNA structures to remain structurally independent. Flanking the structural core of the construct are structure cassettes[25]; these stem-loop-forming regions are used as primer-binding sites for steps required in the screening workflow and were designed not to interact with other structures in the construct (FIG. 7).

Another component of the screening construct is the RNA barcode; barcoding enables multiplexing that substantially reduces the downstream workload. Each well in a 96-well plate used for screening a fragment library contains an RNA with a unique barcode in the context of an otherwise identical construct; the barcode sequence thus identifies the well position, and the fragment (or fragments) present post multiplexing (FIG. 1). The RNA barcode region was designed to fold into a self-contained structure that does not interact with any other part of the construct. The barcode structure is a seven-base-pair helix capped with a GNRA tetraloop and anchored with a G-C base pair to maintain hairpin stability (FIG. 7). Each set of 96 barcodes was designed such that any individual barcode undergoes two or more mutations to be misconstrued as another barcode.

This construct affords flexibility in choosing RNA structures to screen for ligand binding and supports a simple, straightforward screening experiment (FIG. 1). Each well in a 96-well plate, containing an otherwise identical RNA construct with a unique RNA barcode, is incubated with one or a few small-molecule fragments or a no fragment control (solvent) and then exposed to SHAPE reagent. The resulting SHAPE adducts chemically encode per-nucleotide structural information. Post SHAPE-probing, the information needed to determine fragment identity (RNA barcode) and fragment binding (SHAPE adduct pattern) is permanently encoded into each RNA strand, so RNAs from the 96 wells of a plate can be pooled into a single sample. The fragment screening experiment is processed in a manner very similar to a standard MaP structure-probing workflow[24]. For example, in some embodiments, a specialized relaxed fidelity reverse transcription reaction is used to make cDNAs that contain non-template encoded sequence changes at the positions of any SHAPE adducts on the RNA[30]. These cDNAs are then used to prepare a DNA library for high-throughput sequencing. Multiple plates of experiments can be barcoded at the DNA library level[24] to allow collection of data on thousands of compounds in a single sequencing run (FIG. 1). The resulting sequencing data contain millions of individual reads, each corresponding to specific RNA strands. These reads are sorted by barcode to allow analysis of data for each small-molecule fragment or combination of fragments. Determination and identification of small-molecule fragments (e.g., fragment 1 and/or fragment 2) employing the above described methods, such as SHAPE and/or SHAPE-MaP, are described in more detail in the next section.

C. Ligand Identification and Selection

As mentioned above, SHAPE and SHAPE-MaP were used to identify small-molecule fragments that bind to or associate with an RNA molecule of interest. Particularly when testing small-molecule fragments using SHAPE-Map, the detection of bound fragment signatures from per-nucleotide SHAPE-MaP mutation rates involves multiple steps to normalize data across a large experimental screen and to ensure statistical rigor. Key features of the SHAPE-based hit analysis strategy include: (i) comparison of each fragment-exposed RNA, or "experimental sample", to five negative, no-fragment exposed, control samples to account for plate-to-plate and well-to-well variability; (ii) hit detection performed independently for each of the two structural motifs in the construct, in this disclosure, the pseudoknot and TPP riboswitch; (iii) masking of individual nucleotides with low reactivities across all samples as these nucleotides are unlikely to show fragment-induced changes; and (iv) calculation of per-nucleotide differences in mutation rates between the fragment-exposed experimental sample and the no-fragment-exposed negative control sample. Those nucleotides with a 20% or greater difference in mutation rate between one of the motifs and the no-fragment controls were selected for Z-score analysis. However, a skilled artisan would be able to adjust the difference in mutation rate accordingly recognizing that it can vary. For example, in some embodiments, the difference in mutation rate can be 25%, 30%, 35%, 45%, or 50% or greater. In some embodiments, the difference in mutation rate can be 15%, 10%, or 5% or greater. A fragment was determined to have significantly altered the SHAPE reactivity pattern if three or more nucleotides in one of the two motifs had Z-values greater than 2.7 (as determined by comparison of the Poisson counts for the two motifs[31], see Example 2). However, the Z-values may vary, and a skilled artisan would be able to adjust them accordingly. For example, in some embodiments, the Z-values are greater than 2.8, 2.9, 3.0, 3.1, 3.2, 3.3, 3.4, 3.5, 3.6, 3.7, 3.8, or 3.9. In some embodiments, the Z-values are greater than 1.0, 1.1, 1.2, 1.3, 1.4, 1.5, 1.6, 1.7, 1.8, 1.9, 2.0, 2.1, 2.2, 2.3, 2.4, 2.5, or 2.6.

In order to identify small-molecule fragments with SHAPE and/or SHAPE-MaP that subsequently are linked together to generate compounds as disclosed herein, a series of steps are carried out. First, a primary screen is carried out, which screens a large number of compounds, e.g., at least 100 compounds, to identify any initial lead or hit compounds that exhibit suitable binding activity toward a target RNA molecule. In step 2, these hit compounds are then further examined in structure-activity-relationship (SAR) studies where changes in target RNA binding affinity are determined as the structure of the hit compounds are being modified. When multiple small-molecule fragments are identified as being suitable binding ligands for the target RNA molecule, additional binding studies may be carried out to further investigate the binding site for each small-molecule fragment (i.e., step 3). For example, in some embodiments, the target RNA can be pre-incubated with a first fragment (identified as a target RNA binding ligand according to the SAR studies in step 2) prior to exposure of the target RNA with a second fragment (also identified as an RNA binding ligand in SAR studies of step 2) to identify whether the second fragment can bind to the target RNA when the first fragment is already bound. Once a second fragment with suitable binding activity to the RNA of interest has been identified, it can be linked to the first fragment with a linker to render a compound as disclosed herein (i.e., step 4). Each of the above mentioned steps is described in more detail below.

Step 1: Primary Screening

Figure 2:
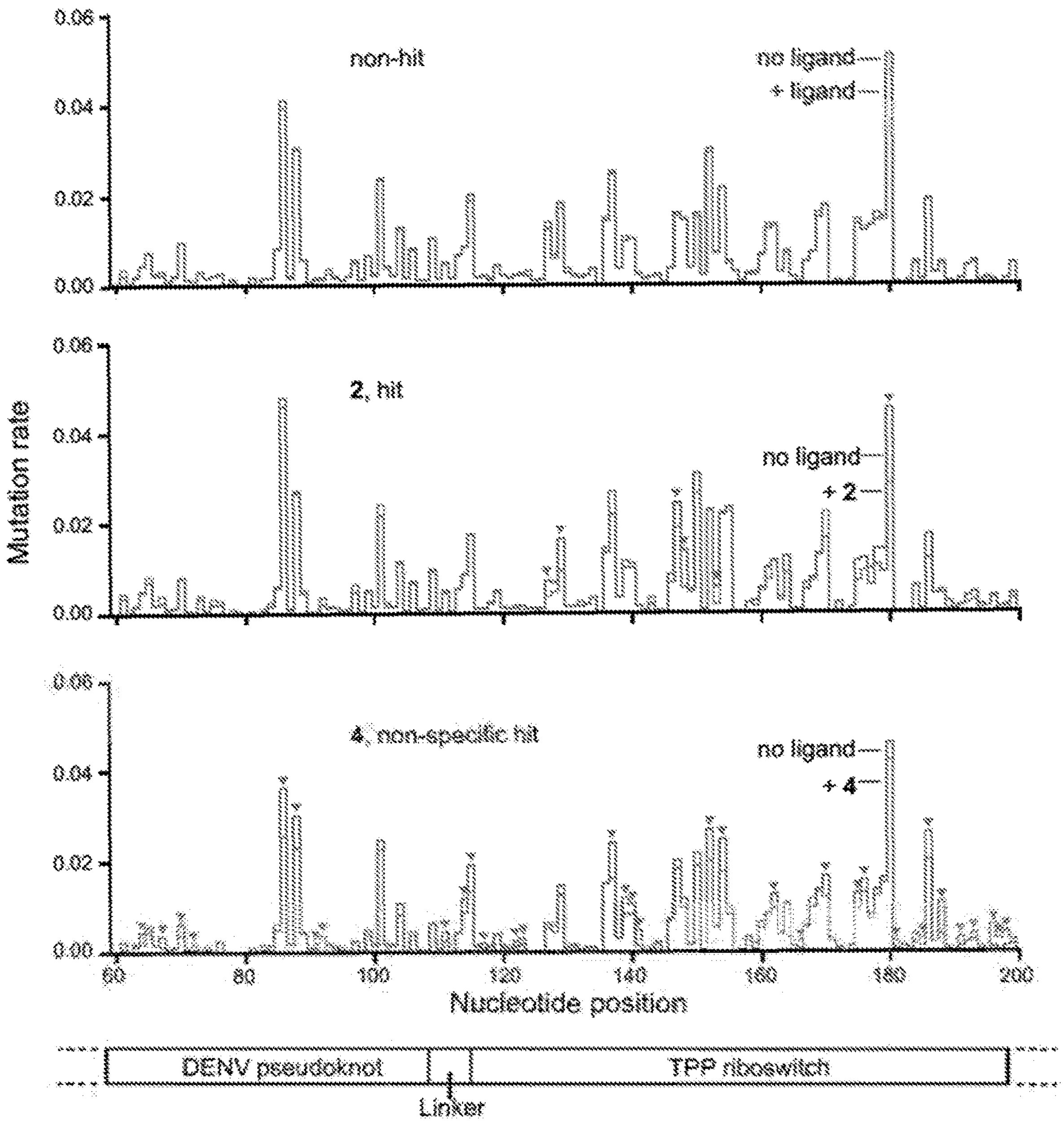
FIG. 2 shows representative mutation rate comparisons for fragment hits and non-hits. Normalized mutation rates for fragment-exposed samples are labeled as ligand, 2, or 4 and are compared to no-ligand traces labeled as no ligand. Statistically significant changes in mutation rate are denoted with triangles (see FIG. 8 for SHAPE confirmation data). (top) Mutation rate comparison for a representative fragment that does not bind the test construct. (middle) Fragment hit to the TPP riboswitch region of the RNA. (bottom) Non-specific hit that induces reactivity changes across the entirety of the test construct. Motif 1 and 2 landmarks are shown below SHAPE profiles.
Figure 8:
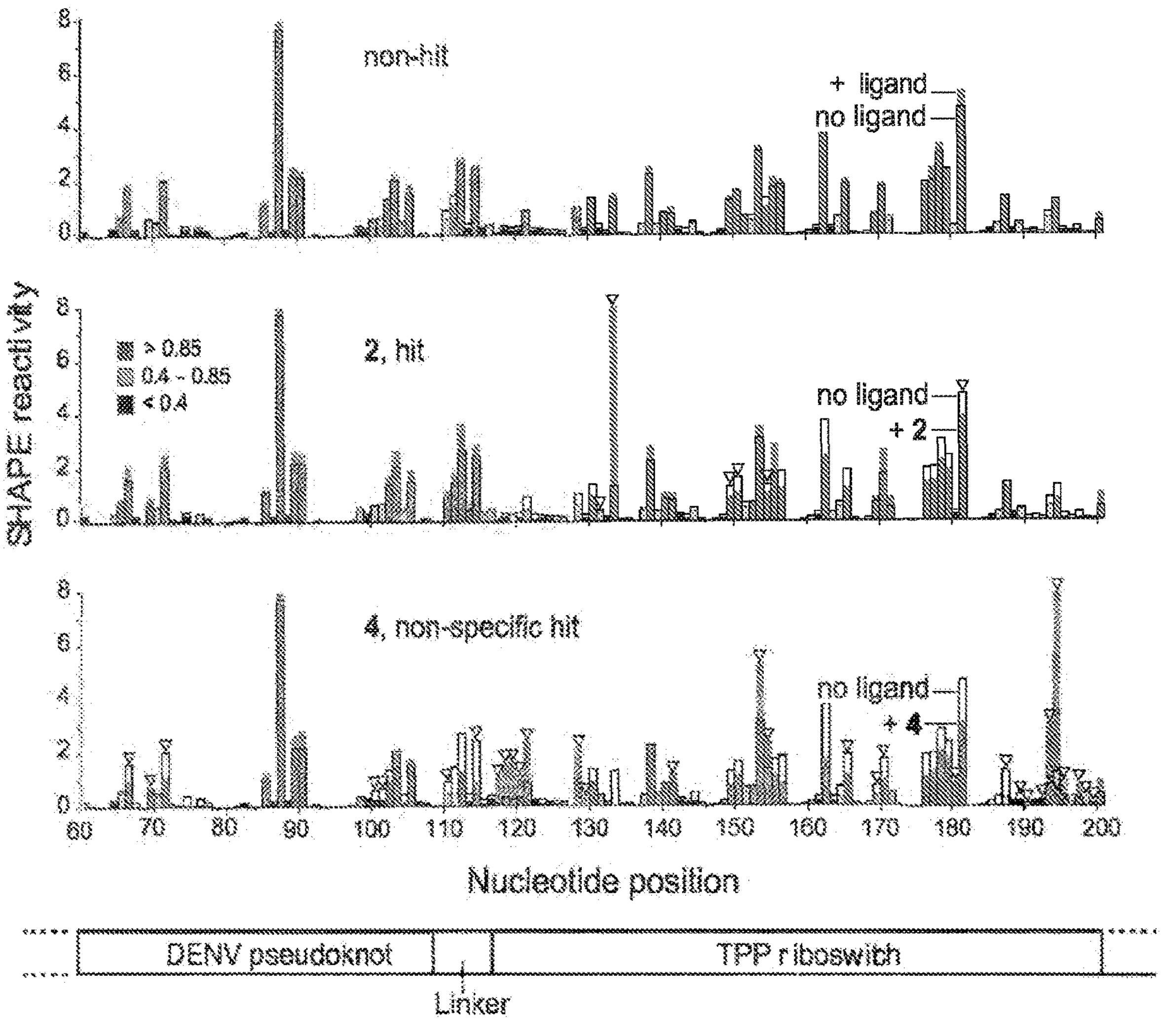
FIG. 8 shows SHAPE profiles for non-hit, hit, and non-specific hit fragments. Mutation rate traces corresponding to fragment-exposed and no-ligand control traces are in solid grey shades and in black outline, respectively. Nucleotides determined to be statistically significantly different in fragment versus no fragment samples are denoted by triangles. Mutation rate traces for the same fragments are shown schematically in FIG. 2.

In the primary screen, 1,500 fragments were tested and 41 fragments were detected as hits, for an initial hit rate of 2.7%. Hit validation was performed via triplicate SHAPE analysis (FIG. 2, FIG. 8), and a compound was only accepted as a true hit if it was detected as a binder in all three replicates. These replicated hit compounds were then analyzed by isothermal titration calorimetry (ITC) to determine binding affinities for an RNA corresponding just to the target motif (omitting flanking sequences in the screening construct). Of these initial hits, eight hits were validated by replicate analysis and ITC (Table 1). Seven of the hits bound the TPP riboswitch, based on their mutation signatures localizing mostly or entirely within the TPP riboswitch region of the test construct. The remaining hit was nonspecific, as this fragment affected nucleotides across all portions of the RNA construct. No compounds were detected that specifically bound the dengue pseudoknot region of the test construct.

TABLE 1

Fragments that bind the TPP riboswitch as detected by SHAPE probing.

| Structure | ID | $K_d$ (μM) |
|---|---|---|
| 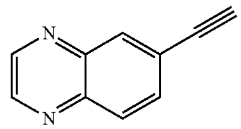 | 1 | 11 ± 0.2 |
| 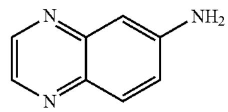 [SMILES: Nc1ccc2nccnc2c1] | 2 | 25 ± 6 ‡ |
| 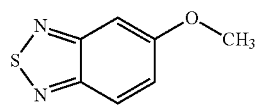 | 3 | 95 ± 3 |
| 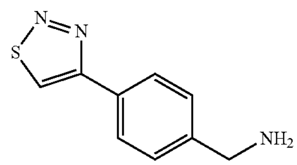 [SMILES: NCc1ccc(-c2csnn2)cc1] | 4 | 220 ± 10 |
| 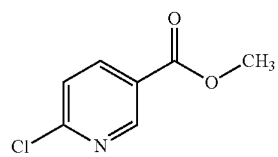 | 5 | 265 ± 80 ‡ |
| 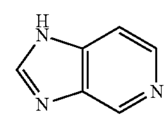 | 6 | 650 ± 100 |
| 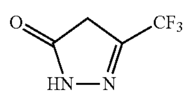 | 7 | insoluble |
| 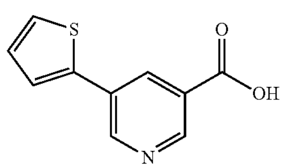 [SMILES: O=C(O)c1cncc(-c2cccs2)c1] | 8 | insoluble |
| 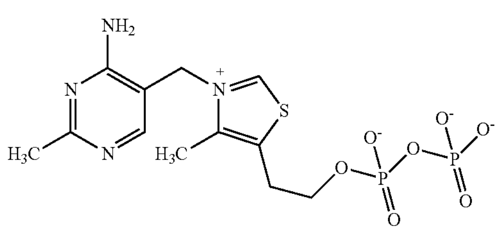 | 9 | 0.029 ± 0.002 |

Hits were detected by SHAPE structure probing and verified by replicate analysis and ITC. Dissociation constant was determined by ITC; error values marked with ‡ denote standard error derived from ≥3 replicates, other error estimates are calculated based on 95% confidence interval for the least-squares regression of the binding curve. The native TPP ligand is included for comparison.

The seven fragments that bound the TPP riboswitch, as validated by ITC, have diverse chemotypes; most have few or no similarities to the native TPP ligand (Table 1). Overall, heteroaromatic nitrogen-containing rings predominate; these likely participate in hydrogen bonding interactions. Three compounds have pyridine rings and two have pyrazine rings. The azole ring moiety is present in three compounds: two thiadiazoles and an imidazole. There is a thiazole ring in the native TPP ligand, but this moiety does not participate in binding interactions with the RNA[28,29,33]. Additionally, a number of the identified fragments contain primary amines, esters and ethers, and fluorine groups that could serve as hydrogen bond acceptors or donors.

Step 2: Structure-Activity Relationships (SARs) of Riboswitch-Binding Fragments Next, analogs of some of the initial hits were examined with the goal of increasing binding affinity and identifying positions at which fragment hits could be modified with a linker without hindering binding. In particular, analogs of compounds 2 and 5 were considered, as these two fragments are structurally distinct and analogs are commercially available. Analog-RNA binding was evaluated by ITC. Sixteen analogs of 2 were tested. Altering the core quinoxaline structure of 2 by removing one or both ring nitrogens resulted in changes of the binding activity (Table 2A).

TABLE 2A

SAR for fragment 2 analogs.

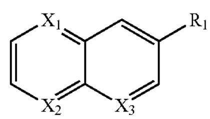

| Molecule | $R_1$ | $X_1$, $X_2$, $X_3$ | $K_d$ (μM) |
|---|---|---|---|
| 2 | 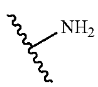 | N, N, C | 25 |

TABLE 2A-continued

SAR for fragment 2 analogs.

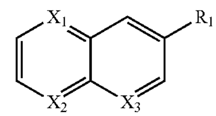

| Molecule | $R_1$ | $X_1$, $X_2$, $X_3$ | $K_d$ (μM) |
|---|---|---|---|
| 10 | 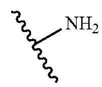 | N, C, C | 3500 |
| 11 | 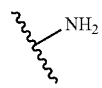 | C, N, C | 2100 |
| 12 | 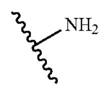 | C, C, C | no binding |
| 13 | H | N, N, N | 354 |
| 14 | H | N, N, C | 120 |

Modifications to the quinoxaline core were examined and dissociation constants were obtained by ITC.

Improvements in binding affinity resulted from introduction of a methylene-linked hydrogen bond donor or acceptor (Table 2B, compounds 16 and 17). Varying substituents at other positions on the quinoxaline ring core resulted in a decrease in binding activity. Compound 2 was a good candidate for further development based on the high degree of flexibility, and even improvement in binding, observed upon modification of the substituent at the C-6 position.

TABLE 2B

Structure-activity relationships for analogs of fragment 2 binding to the TPP riboswitch RNA. Modifications to the pendant groups of the quinoxaline core. Dissociation constants were obtained by ITC.

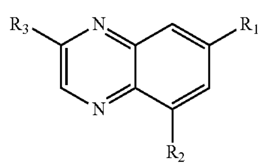

| Molecule | $R_1$ | $R_2$ | $R_3$ | $K_d$ (μM) |
|---|---|---|---|---|
| 15 | 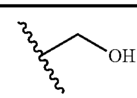 | H | H | 18 |
| 16 | 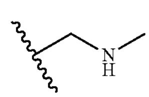 [SMILES: *CNC] | H | H | 12 |
| 17 | 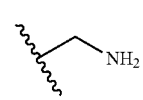 | H | H | 5.0 |
| 18 | 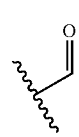 | H | H | 35 |

TABLE 2B-continued

Structure-activity relationships for analogs of fragment 2 binding to the TPP riboswitch RNA. Modifications to the pendant groups of the quinoxaline core. Dissociation constants were obtained by ITC.

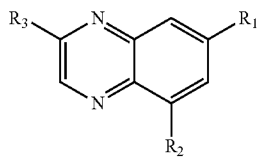

| Molecule | $R_1$ | $R_2$ | $R_3$ | $K_d$ (μM) |
|---|---|---|---|---|
| 19 | 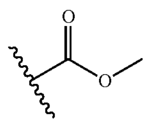 [SMILES: *C(=O)OC] | H | H | 58 |
| 20 | 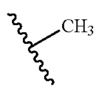 | H | H | 33 |
| 21 | H | 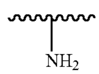 | H | 75 |
| 22 | H | 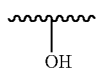 | H | 286 |
| 23 | H | 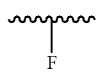 | H | 220 |
| 24 | H | H | 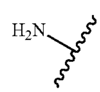 | 379 |
| 25 | H | H | 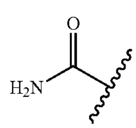 | 600 |

Next, examination of 18 analogs of fragment 5 suggested the core pyridine functionality of the molecule appears to be important for binding, as changing the ring nitrogen position, adding, or removing a ring nitrogen all reduced or abrogated binding (Table 3).

TABLE 3

Structure-activity relationships for analogs of fragment 5 binding to the TPP riboswitch RNA. Modifications to the pyridine core and dissociation constants were obtained by ITC.

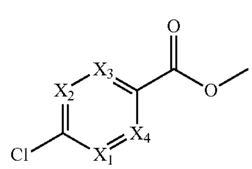

| Molecule | $X_1$, $X_2$, $X_3$, $X_4$ | $K_d$ (μM) |
|---|---|---|
| 6 | N, C, C, C | 266 |
| S1 | C, C, C, N | 490 |
| S2 | N, N, C, C | 420 |
| S3 | N, C, N, C | 1200 |
| S4 | C, C, C, C | no binding |

Modifications to ring substituents generally resulted in a significant loss of binding activity (Table 4). The only affinity-increasing analog featured a chlorine at the C-4 position, S12, yielding a compound had approximately threefold higher affinity for the TPP riboswitch than did fragment 5.

TABLE 4

Structure-activity relationships for analogs of fragment 5 binding to the TPP riboswitch RNA. Modifications to the pendant groups of the pyridine core. Dissociation constants were obtained by ITC.

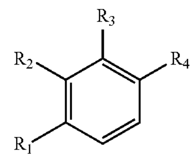

| Molecule | $R_1$ | $R_2$ | $R_3$ | $R_4$ | $K_d$ (μM) |
|---|---|---|---|---|---|
| S5 | 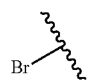 | H | H | 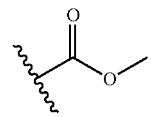 | 440 |
| S6 | 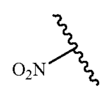 | H | H | 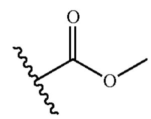 [SMILES: *C(=O)OC] | 390 |
| S7 | 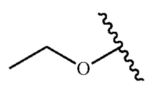 | H | H | 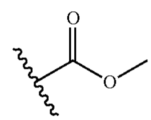 [SMILES: *C(=O)OC] | 1800 |
| S8 | 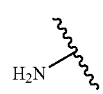 | H | H | 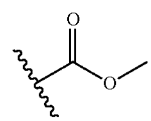 [SMILES: *C(=O)OC] | 1100 |
| S9 | 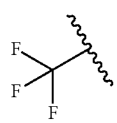 | H | H | 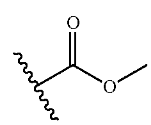 | no binding |
| S10 | 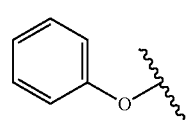 [SMILES: *Oc1ccccc1] | H | H | 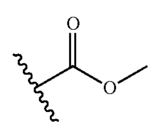 [SMILES: *C(=O)OC] | no binding |
| S11 | 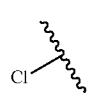 | 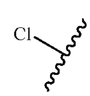 | H | 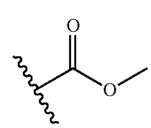 | 820 |
| S12 | 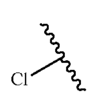 | H | 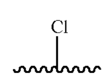 | 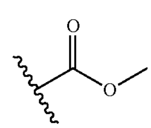 [SMILES: *C(=O)OC] | 93 |
| S13 | 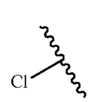 | H | H | 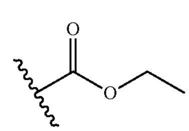 [SMILES: *C(=O)OCC] | 600 |

TABLE 4-continued

Structure-activity relationships for analogs of fragment 5 binding to the TPP riboswitch RNA. Modifications to the pendant groups of the pyridine core. Dissociation constants were obtained by ITC.

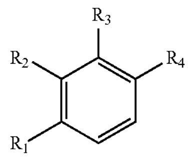

| Molecule | $R_1$ | $R_2$ | $R_3$ | $R_4$ | $K_d$ (μM) |
|---|---|---|---|---|---|
| S14 | 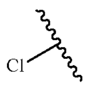 | H | H | 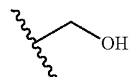 [SMILES: *CO] | 1300 |
| S15 | 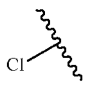 | H | H | 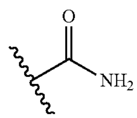 | 1800 |
| S16 | 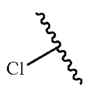 | H | H | 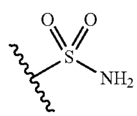 [SMILES: *S(N)(=O)=O] | 1300 |
| S17 | 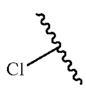 | H | H | 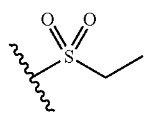 [SMILES: *S(=O)(=O)CC] | no binding |
| S18 | 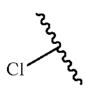 | H | H | 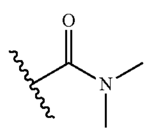 [SMILES: *C(=O)N(C)C] | no binding |

Figure 3A:
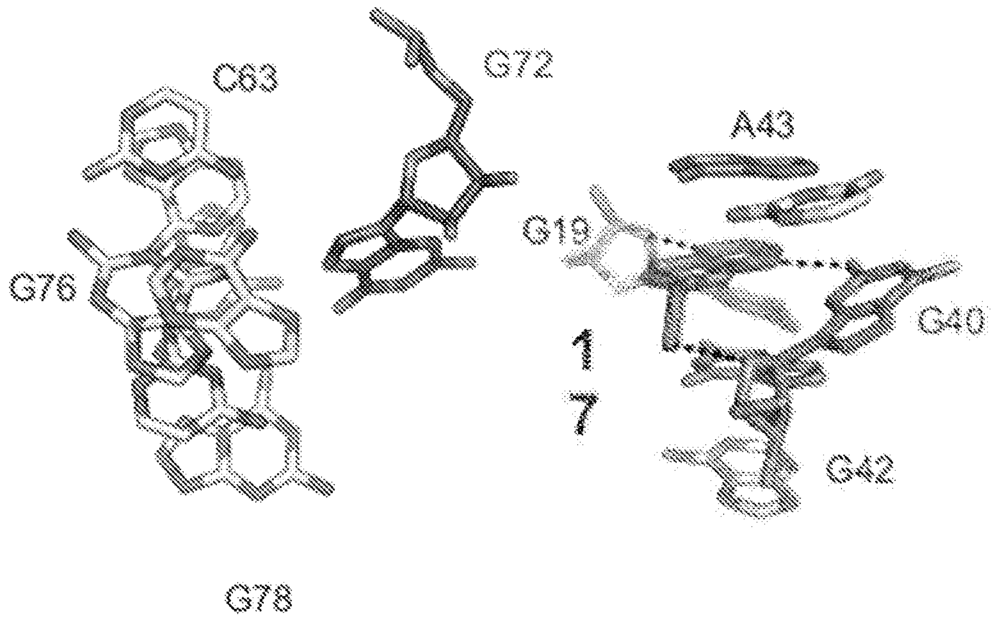
FIGS. 3A and 3B show comparison of the structures of the TPP riboswitch bound by (FIG. 3A) fragment 17 versus (FIG. 3B) the native TPP ligand (2HOJ[28]). RNA structures are shown in similar orientation in each image. Hydrogen bonds between ligands and RNA are shown as dashed lines.
Figure 3B:
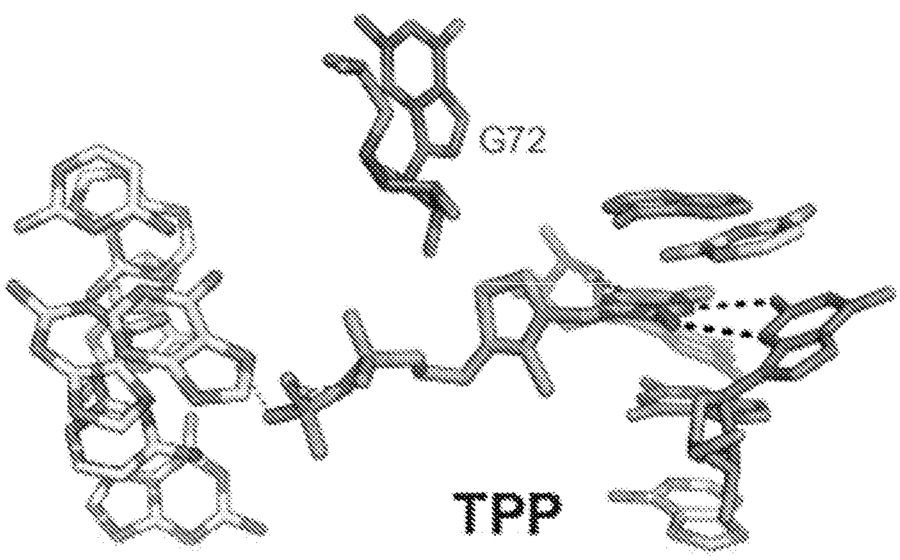

Step 3: Identification of fragments that bind to a second site on the TPP riboswitch Second-rounds screens were employed to identify fragments that bound to the TPP riboswitch region of the screening construct pre-bound to compounds 2 or S12. This screen identified fragments that preferentially interact with the TPP riboswitch when 2 or S12 are already bound, either due to cooperative effects or because new modes of binding become available due to structural changes that occur upon primary ligand binding (FIG. 3). Of the 1,500 fragments screened, five were validated to bind simultaneously with either 2 or S12 (Table 5).

TABLE 5

Fragments that bind the TPP riboswitch in the presence of a pre-bound fragment partner, as detected by SHAPE. Hits were validated by replicate SHAPE analysis. Primary binding partners (2, 6) are shown in Table 1.

| Primary Partner | ID | Structure |
|---|---|---|
| 2 | 26 | 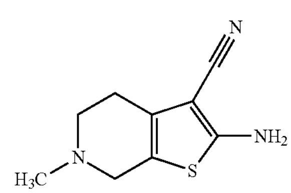 |

TABLE 5-continued

Fragments that bind the TPP riboswitch in the presence of a pre-bound fragment partner, as detected by SHAPE. Hits were validated by replicate SHAPE analysis. Primary binding partners (2, 6) are shown in Table 1.

| Primary Partner | ID | Structure |
|---|---|---|
| 2 | 27 | 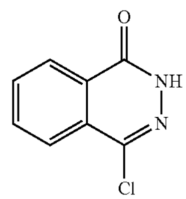 [SMILES: O=c1[nH]nc(Cl)c2ccccc12] |
| 2 | 28 | 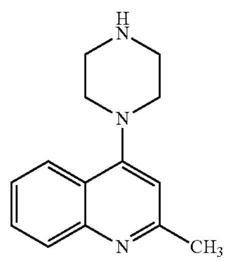 [SMILES: Cc1cc(N2CCNCC2)c2ccccc2n1] |
| 6, 2 | 29 | 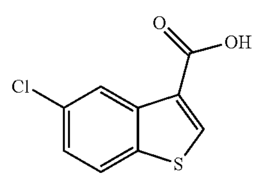 [SMILES: O=C(O)c1csc2ccc(Cl)cc12] |
| 6 | 30 | 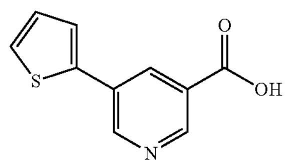 [SMILES: O=C(O)c1cncc(-c2cccs2)c1] |

One second-screen hit, 29, induced a very robust change in the SHAPE reactivity signal and appeared to cause a considerable alteration of the RNA structure, including unfolding of the P1 helix. This fragment caused changes in other areas of the RNA consistent with nonspecific interactions, so this fragment was not considered further as a candidate for fragment linking. Fragment 28 was insoluble at the concentrations needed for ITC analysis; so related analogues containing a pyridine instead of a quinoline ring were examined by ITC (Table 6). These compounds bound with weak affinities, nonetheless 31 and 32 showed clear, but modest, binding cooperativity with 2.

TABLE 6

Structure-activity relationships for analogs of fragment 28 binding to the TPP riboswitch RNA, in the presence and absence of pre-bound fragment 2.*

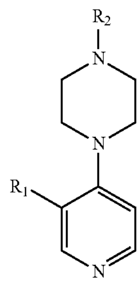

| Molecule | $R_1$ | $R_2$ | $K_d$ (mM) 5 pre-bound | No ligand bound |
|---|---|---|---|---|
| 31 | H | H | 3 | >10 |
| 32 | 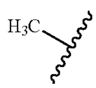 | H | 4 | >10 |
| 33 | H | 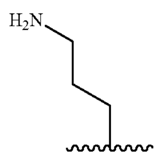 [SMILES: *CCCN] | und | >10 |
| 34 | 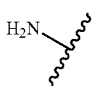 | H | und | >10 |
| 28 | 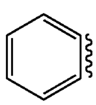 | H | insoluble | insoluble |

*und (undetermined) due to inability to fit ITC binding curve; insoluble, compound insoluble at concentrations required for ITC.

| Fragment 1 | $K_d$ Fragment 1 | Linked compound | LE | E |
|---|---|---|---|---|
| 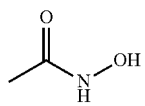 6.2 mM | 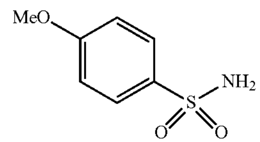 1.5 mM | 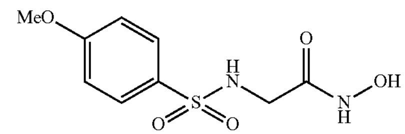 [SMILES: COc1ccc(S(=O)(=O)NCC(=O)NO)cc1] 20 nM | 0.62 | 0.0021 |
| 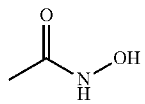 17 mM | 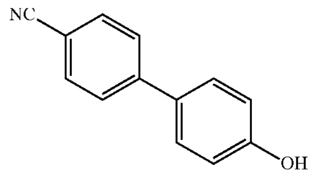 [SMILES: N#Cc1ccc(-c2ccc(O)cc2)cc1] 20 μM | 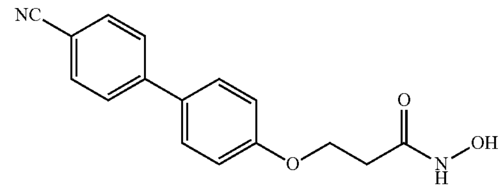 [SMILES: N#Cc1ccc(-c2ccc(OCCC(=O)NO)cc2)cc1] 25 nM | 0.49 | 0.6 |
| 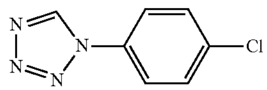 [SMILES: Clc1ccc(-n2cnnn2)cc1] 330 μM | 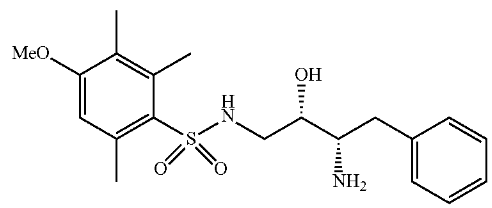 [SMILES: COc1cc(C)c(S(=O)(=O)NC[C@H](O)[C@@H](N)Cc2ccccc2)c(C)c1C] 12 μM | 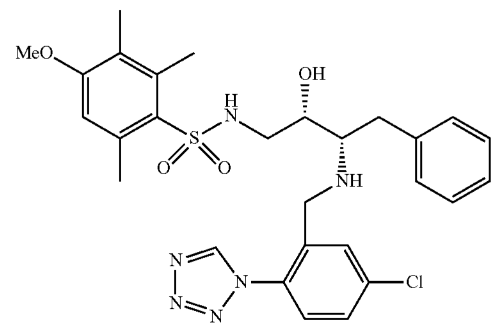 [SMILES: COc1cc(C)c(S(=O)(=O)NC[C@H](O)[C@H](Cc2ccccc2)NCc2cc(Cl)ccc2-n2cnnn2)c(C)c1C] 1.4 nM | 0.30 | 0.35 |

-continued
| Fragment 1 | $K_d$ Fragment 1 | Linked compound | LE | E |
|---|---|---|---|---|
| 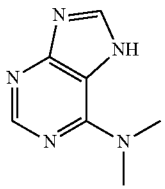 | 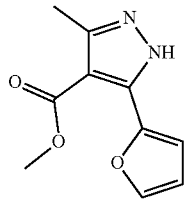 | 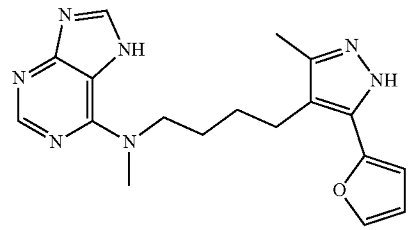 [SMILES: Cc1n[nH]c(-c2ccco2)c1CCCCN(C)c1ncnc2nc[nH]c12] | 0.31 | 1.0 |
| 1.5 mM | 1 mM | 1.5 μM | | |
| 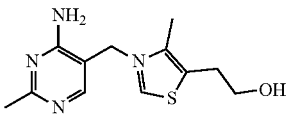 | 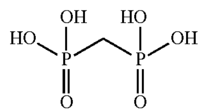 | 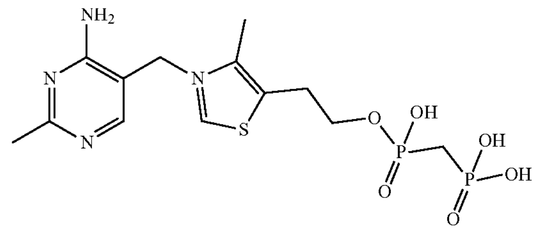 | 0.40 | 1.4* |
| 11 μM | >1 mM | 19 nM | | |
| 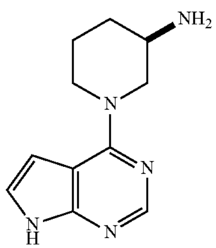 [SMILES: N[C@@H]1CCCN(c2ncnc3[nH]ccc23)C1] | 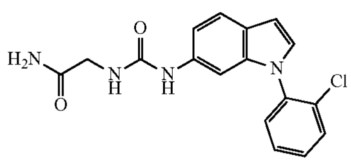 [SMILES: NC(=O)CNC(=O)Nc1ccc2ccn(-c3ccccc3Cl)c2c1] | 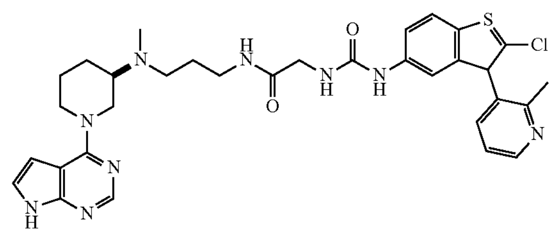 | 0.40 | 1.4 |
| 240 μM | 9.0 μM | 3 nm | | |

-continued
| Fragment 1 | $K_d$ Fragment 1 | Linked compound | LE | E |
|---|---|---|---|---|
| 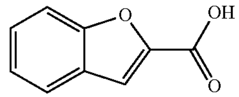 [SMILES: O=C(O)c1cc2ccccc2o1] 1 mM | 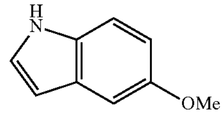 [SMILES: COc1ccc2[nH]ccc2c1] 1.1 mM | 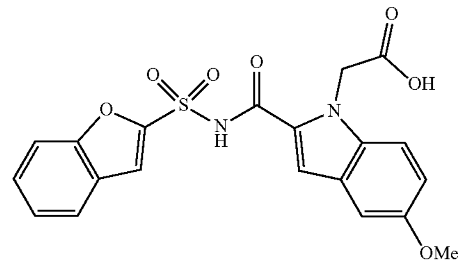 [SMILES: COc1ccc2c(c1)cc(C(=O)NS(=O)(=O)c1cc3ccccc3o1)n2CC(=O)O] 1.8 uM | 0.26 | 1.6 |
| 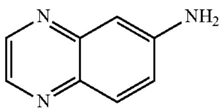 25 μM | 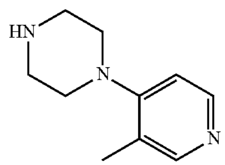 >10 mM | 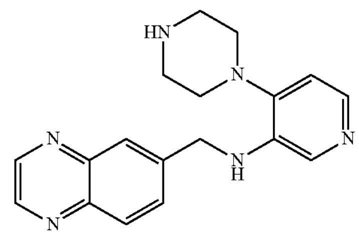 [SMILES: c1cc(N2CCNCC2)c(NCc2ccc3nccnc3c2)cn1] 620 nM | 0.34 | 2.5* |
| 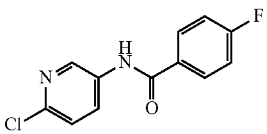 [SMILES: O=C(Nc1ccc(Cl)nc1)c1ccc(F)cc1] 114 μM | 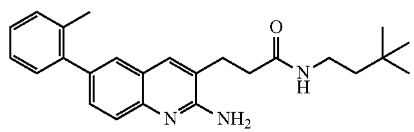 140 nM | 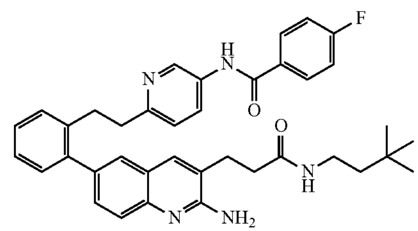 [SMILES: CC(C)(C)CCNC(=O)CCc1cc2cc(-c3ccccc3CCc3ccc(NC(=O)c4ccc(F)cc4)cn3)ccc2nc1N] 400 pM | 0.28 | 25 |

-continued
| Fragment 1 | $K_d$<br>Fragment 1 | Linked compound | LE | E |
|---|---|---|---|---|
| 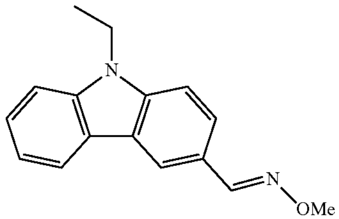 [SMILES: CCn1c2ccccc2c2cc(/C=N/OC)ccc21]<br>40 μM | 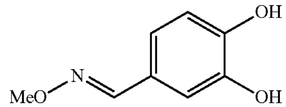<br>41 μM | 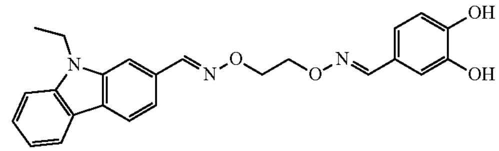 [SMILES: CCn1c2ccccc2c2ccc(/C=N/OCCO/N=C/c3ccc(O)c(O)c3)cc21]<br>64 nM | 0.32 | 39 |
| 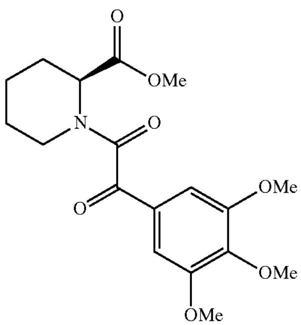 [SMILES: COC(=O)[C@@H]1CCCCN1C(=O)C(=O)c1cc(OC)c(OC)c(OC)c1]<br>2 μM | 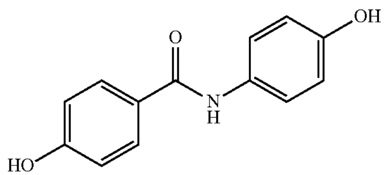 [SMILES: O=C(Nc1ccc(O)cc1)c1ccc(O)cc1]<br>100 μM | 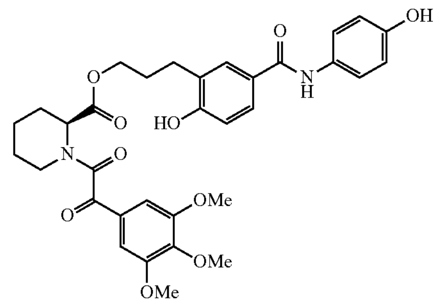 [SMILES: COc1cc(C(=O)C(=O)N2CCCC[C@H]2C(=O)OCCCc2cc(C(=O)Nc3ccc(O)cc3)ccc2O)cc(OC)c1OC]<br>49 nM | 0.22 | 250 |
| 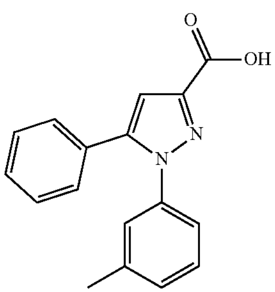 [SMILES: Cc1cccc(-n2nc(C(=O)O)cc2-c2ccccc2)c1]<br>150 μM | 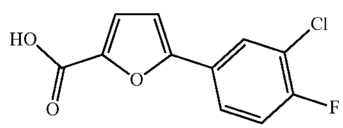 [SMILES: O=C(O)c1ccc(-c2ccc(F)c(Cl)c2)o1]<br>580 μM | 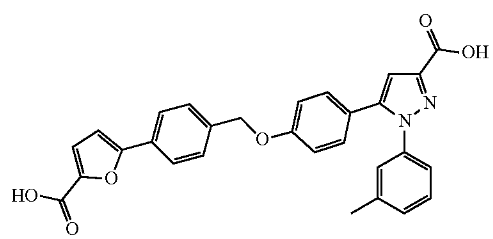 [SMILES: Cc1cccc(-n2nc(C(=O)O)cc2-c2ccc(OCc3ccc(-c4ccc(C(=O)O)o4)cc3)cc2)c1]<br>26 μM | 0.17 | 300 |

-continued
| Fragment 1 | $K_d$ Fragment 1 | Linked compound | LE | E |
|---|---|---|---|---|
| 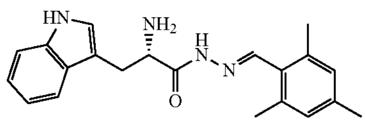 [SMILES: Cc1cc(C)c(/C=N/NC(=O)[C@@H](N)Cc2c[nH]c3ccccc23)c(C)c1] 13 μM | 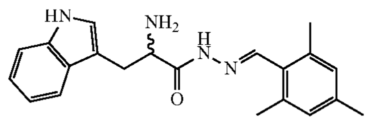 [SMILES: Cc1cc(C)c(/C=N/NC(=O)C(N)Cc2c[nH]c3ccccc23)c(C)c1] 13 μM | 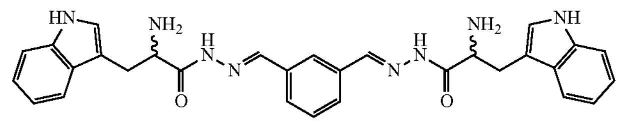 [SMILES: NC(Cc1c[nH]c2ccccc12)C(=O)N/N=C/c1cccc(/C=N/NC(=O)C(N)Cc2c[nH]c3ccccc23)c1] 54 nM | 0.25 | 330 |
| 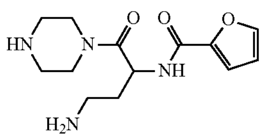 100 μM | 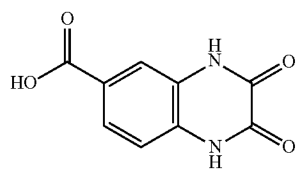 [SMILES: O=C(O)c1ccc2[nH]c(=O)c(=O)[nH]c2c1] >100 μM | 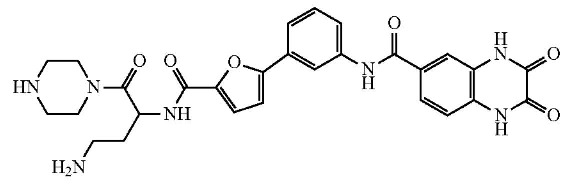 [SMILES: NCCC(NC(=O)c1ccc(-c2cccc(NC(=O)c3ccc4[nH]c(=O)c(=O)[nH]c4c3)c2)o1)C(=O)N1CCNCC1] 6.5 μM | 0.17 | 650 * |

Step 4: Cooperativity and Fragment Linking

Figure 4A:
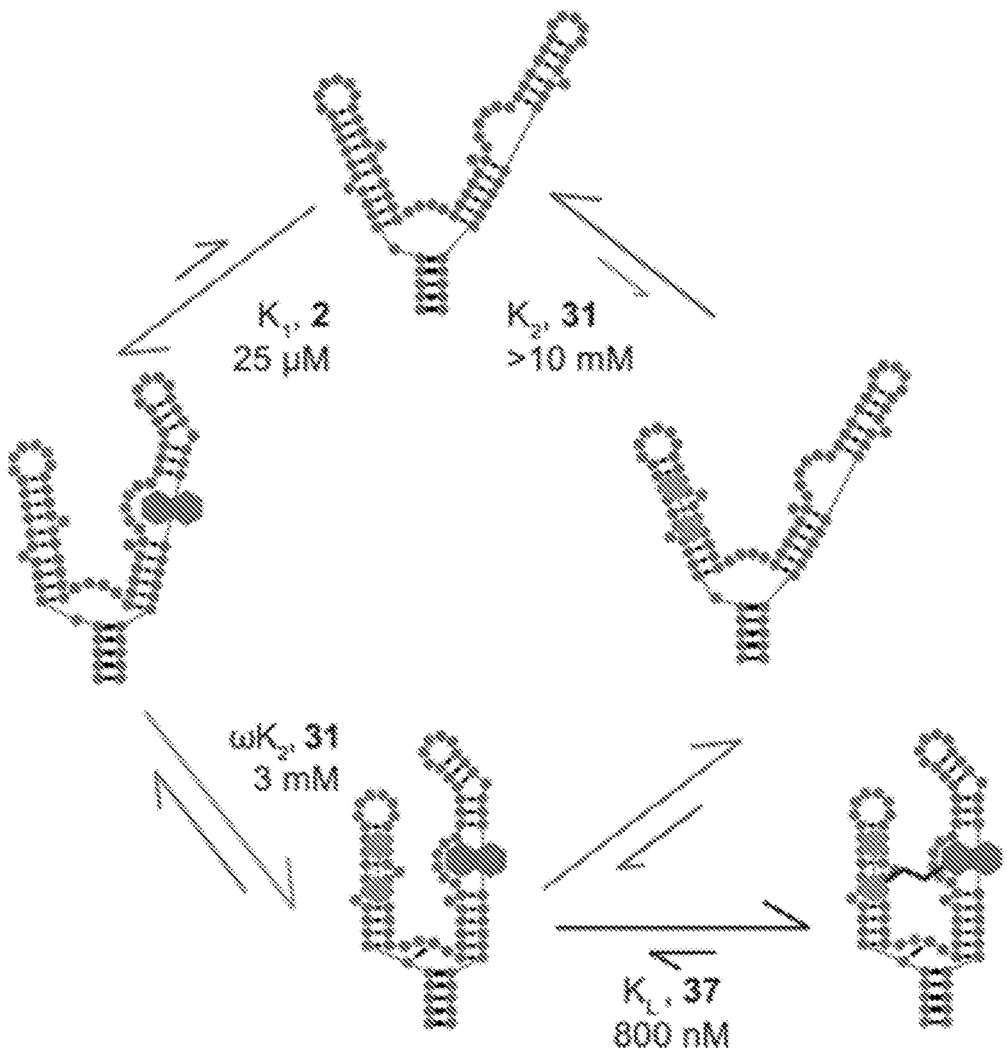
FIGS. 4A and 4B show thermodynamic cycle and step-wise ligand binding affinities for fragments 2 and 31.
Figure 4B:
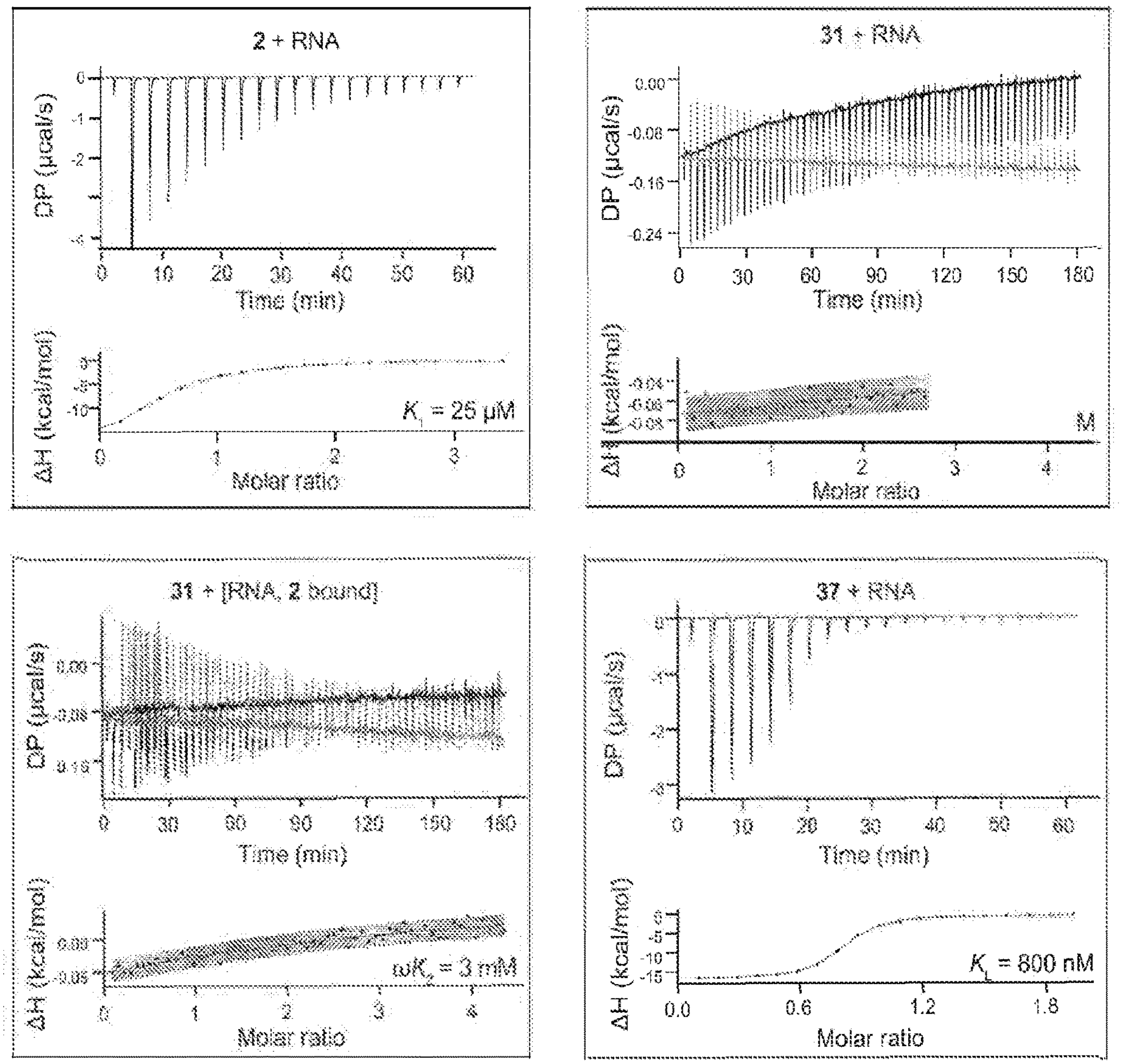

Cooperative binding interactions between 2 and 31 were quantified by ITC. Individually, 2 bound with a $K_d$ of 25 μM, and 31 with a much higher $K_d$ of 10 mM. As in the secondary screen, the affinity of fragment 31 was also examined when 2 was pre-bound to the TPP riboswitch RNA, forming a 2-RNA complex. Under these conditions, fragment 31 bound to the 2-TPP RNA complex with a $K_d$ of approximately 3 mM (FIG. 4). This experiment also showed that, when binding by 2 is saturated, 31 binds to the TPP RNA, implying that these two fragments do not bind in the same location. As 2 and 31 bound with excellent and reasonable affinity, respectively, to distinct regions of the TPP RNA, the two fragments were linked with the goal of creating a high-affinity ligand.

Figure 5:
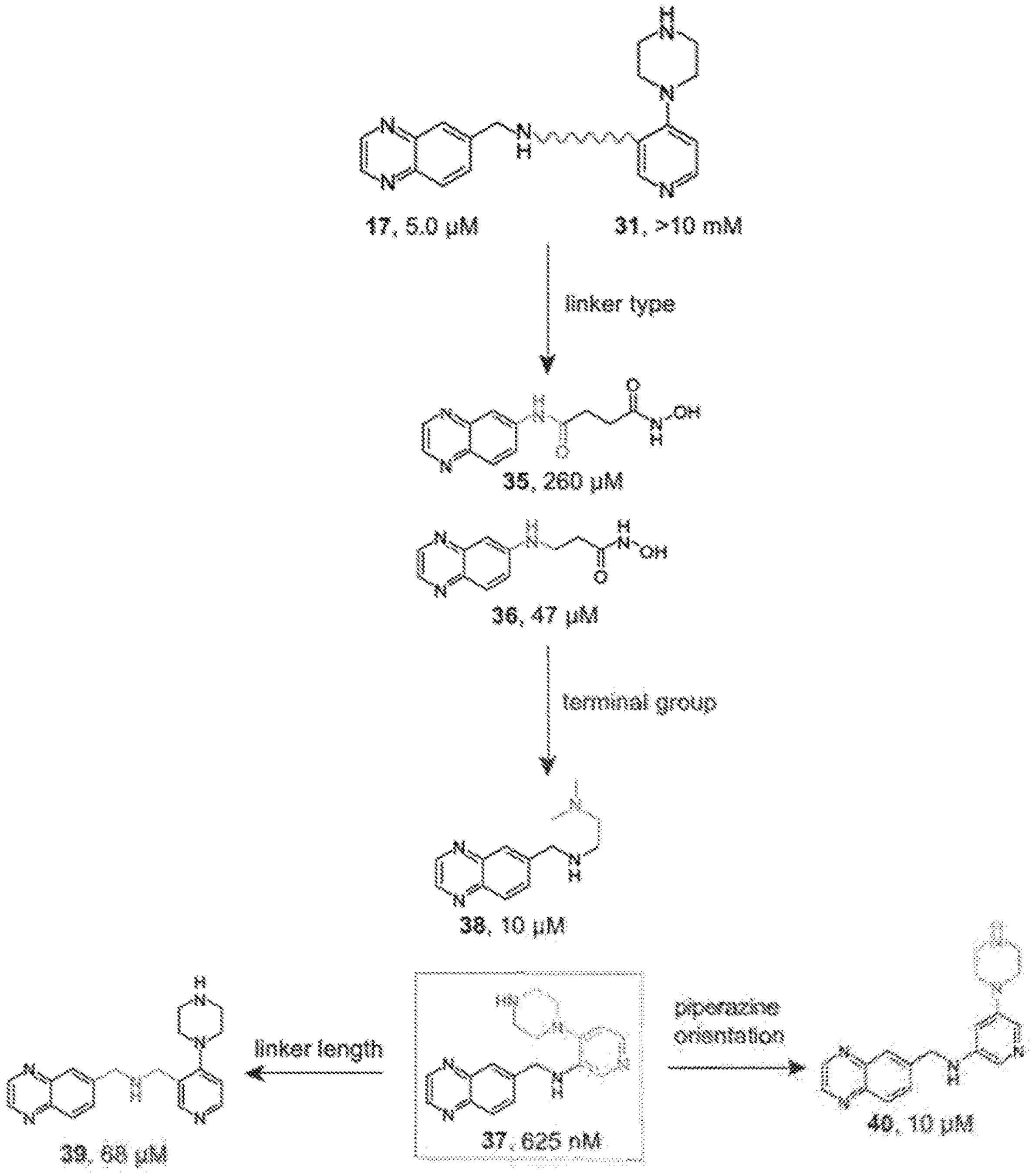
FIG. 5 shows covalent linking of fragments 17 and 31, as a function of linker type and length, terminal group chemotype, and terminal group orientation. Modifications that increase RNA binding affinity are present in compounds 36 and 37 (light grey); negative modification are present in compounds 35, 39, and 40 (light grey), and neutral modifications are present in compound 38 (light grey). Dissociation constants determined by ITC.

Based on the SAR analyses of fragment hits 2 (Table 2B) and 28 (Table 4), linked analogs of the most promising SAR fragments were prepared, focusing on the aminomethyl position of 17 and two sites in the pyridine ring of fragment 31 (FIG. 5). First, affinities of fragments conjugated with an amide or amine linker were compared. A compound with a flexible amine linker (compound 36) had fivefold higher binding affinity than the amide-linked version (compound 35, FIG. 5). These linkages were introduced in the context of a hydroxamic acid which might chelate a magnesium ion[35], as occurs with the pyrophosphate moiety of the native TPP ligand[27,28]. However, the amine-linked hydroxamic acid compound 36 bound with an affinity similar to that of the parent fragment 17, suggesting that the hydroxamic acid moiety does not confer additional binding affinity by chelating an ion. The linked compound 37 binds with a 625 nM affinity, showing that—with the right approximation—linking two fragments of modest affinity can achieve a high-nanomolar binder. Replacing the fragment 31 entity with a tertiary amine (compound 38) reduced affinity relative to compound 37, suggesting the interaction of fragment 31 with the RNA is mediated by more than just charged-based effects. Finally, changing the linkage between the 17 and 31 moieties by length (compound 39) or pyridine ring linkage site (compound 40) reduces affinity relative to compound 37 (FIG. 5). Ultimately, by linking compounds that bound individually to the TPP riboswitch affinities of 5.0 μM (compound 19) and ≥10 mM (compound 31), was created a compound (37) that binds the RNA with a $K_d$ of 625 nM.

A skilled artisan would understand that the above steps I-IV are not meant to be limiting but merely serve as an exemplary embodiment. It would be well understood that a skilled person would be able to apply the above steps I-IV to identify alternate fragments that could be linked together to render compounds as disclosed herein with suitable binding affinity for the TPP riboswitch. Further, it would be well understood that a skilled person would be able to apply the above steps I-IV to identify fragments that can be linked together to render compounds as disclosed herein that bind to other RNA molecules of interest.

D. Summary and Additional Considerations

Because both coding (mRNA) and non-coding RNAs can potentially be manipulated to alter the course of cellular regulation and disease, it was sought to develop an efficient strategy to identify small-molecule ligands for structured RNAs. The study disclosed herein demonstrates the promise of using a SHAPE screening readout detecting ligand binding to RNA melded with a fragment-based strategy. Here, this strategy was used to produce a ligand that binds with a $K_d$ of 625 nM to the TPP riboswitch that is unrelated in structure to the native ligand. The melded SHAPE and fragment-based screening approach is generic with respect to both the RNA structure that can be targeted and to the ligand chemotypes that can be developed. The strategy is specifically well-suited to finding ligands of RNAs with complex structures, which may be essential for identifying RNA motifs that bind in three-dimensional pocket[4]. Additionally, due to the use of a MaP approach and the application of multiplexing through both RNA and DNA barcoding, the effort required to screen a thousand-plus member fragment library is modest, enabling efficient screening of many structurally different targets.

Many of the ligands that were obtained were similar to those reported previously for a single-round screen also performed for the TPP riboswitch[15,17]. Hits in the primary screen appeared to be modestly biased toward higher affinities, such that the majority of ligands detected by SHAPE bound in the 10-300 μM range. The hit detection assay used is likely biased toward detection of the tightest fragment binders and those binders that induce the most substantial changes in SHAPE reactivity. Lower affinity fragments were likely missed. It is believed that this bias toward tight-binding fragments is an advantage overall. No fragments were identified that bound to the dengue pseudoknot that reached the affinity and specificity required to meet the above screening criteria. The dengue pseudoknot RNA is highly structured, and the likelihood that a fragment can perturb this structure might be low. Another possibility is that this particular pseudoknot structure might not contain a ligandable pocket.

The fragment-pair identification strategy, in which a fragment hit from the primary screen was pre-bound to the RNA and screened for additional fragment binding partners, specifically leveraged the per-nucleotide information obtainable by SHAPE and was successfully used here to discover induced-fit fragment pairs (FIG. 4). A core tenet of fragment-based ligand development is that cooperativity between two fragments can be achieved through proximal binding and that this additive binding can be exploited by linking the cooperative fragments together with a minimally invasive covalent linker[20,21,36,37]. Development of the linked compound 37 from primary and secondary fragment hits shows that fragment-based ligand discovery can be efficiently applied to RNA targets. There is a modest degree of cooperativity between 2 and 31: binding by compound was 31 was stronger by 3 to 10-fold when 2 was pre-bound to the RNA. Upon linking these two fragments, modest additivity in their binding energies were observed: 37 had an affinity of 625 nM. No super-additive effect was observed[36] of linking fragments 2 and 31, likely because no perfect positioning of the fragments was achieved. Small changes in the length or geometry of the linker resulted in large changes in the affinity of the linked ligand (FIG. 5), implying that precise orientation of the linker is important to optimally orient the two fragments. Successful development of compound 37 reveals that it is not necessary to achieve perfection in either the degree of cooperativity between the fragments or the construction of the covalent linker joining them to efficiently develop a sub-micromolar ligand.

Figure 6:
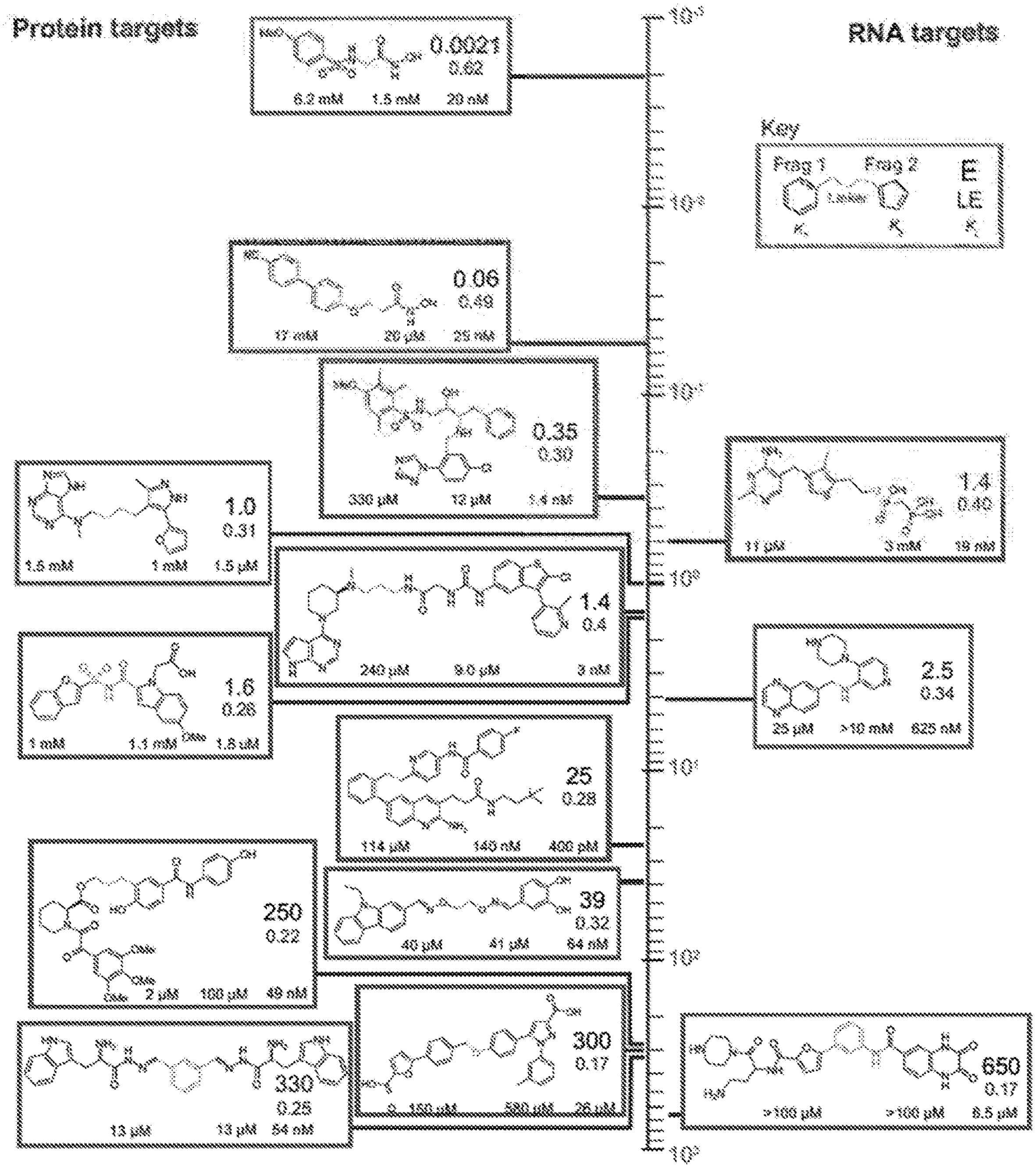
FIG. 6 shows comparison of fragment-linker-fragment ligands developed by fragment-based methods, ordered by their linking coefficient (E). Values shown on a logarithmic axis. Cooperative linking corresponds to lower E values (top of vertical axis). Fragment 37 exhibits a E value of 2.5 and an LE value of 0.34. Dissociation constants for individual fragments (left, middle) and linked ligand (right) are denoted below component fragments; E-value (top) and ligand efficiency (bottom) are shown. Covalent linkage introduced between fragments is highlighted in light grey. Structures for the component fragments are detailed in Table 7.

Although there have been a large number of efforts designed to exploit cooperativity between fragments to obtain tight-binding ligands that target proteins, targeting RNA is in its infancy. It was explored how well the disclosed SHAPE-based screening strategy coupled with linking of fragments compared with prior (protein-focused) efforts. Compounds discovered previously using fragment-based strategies according to their linking coefficients (E) were ranked, a measure of how well the entire system functions together when linked[21,38] (FIG. 6; expanded in Table 7). In the absence of positive or negative contributing factors, the binding energies of the two fragments are exactly additive, the linker is inert, and E is equal to 1.0. Cooperative effects or favorable linker interactions decrease E and anti-cooperative effects or negative linker interactions increase E. Critically, E values can vary by orders of magnitude in protein systems. The linking coefficient for 37 is 2.5, slightly above average for linked (protein-targeted) ligands in the academic literature. 37 has a ligand efficiency (LE), the free energy of binding divided by the number of non-hydrogen atoms, that compares favorably to examples of linked fragment ligands targeting proteins (FIG. 6). By these metrics, 37 performs nearly as well TPPc, a ligand closely related to the native TPP riboswitch ligand[22]. Thus, the fragment-based ligand discovery, especially as efficiently implemented by SHAPE-enabled multiplexed screening, holds significant promise to enable rapid development of unique ligands that target the vast world of RNA structures.

E. Methods of Making

The current disclosure is also directed to any methods for preparing the compounds disclosed herein. A skilled artisan would be aware that such preparative methods can vary. For example, in some embodiments, methods for the preparation of the disclosed compounds comprises:

contacting a fragment of formula IV:

Formula (IV)

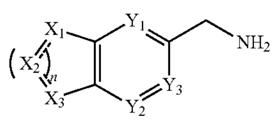

wherein $X_1$, $X_2$, and $X_3$ are independently selected from $CHR_1$, $CR_1$, and heteroatoms N, NH, O and S, wherein adjacent $X_1$, $X_2$, and $X_3$ are not simultaneously selected to be O or S;

the dashed lines represent optional double bonds;

$Y_1$, $Y_2$ and $Y_3$, are independently selected from $CR_2$ and N;

$R_1$ and $R_2$ are independently selected from —H, —Cl, —Br, —I, —F, —$CF_3$, —OH, —CN, —$NO_2$, —$NH_2$, —NH($C_1$-$C_6$ alkyl), —N($C_1$-$C_6$ alkyl)$_2$, —COOH, —COO($C_1$-$C_6$ alkyl), —CO($C_1$-$C_6$ alkyl), —O($C_1$-$C_6$ alkyl), —OCO($C_1$-$C_6$ alkyl), —NCO($C_1$-$C_6$ alkyl), —CONH $C_1$-$C_6$ (alkyl), and substituted or unsubstituted $C_1$-$C_6$ alkyl; and n is selected from integers 1 and 2, wherein when n is 1, only one of the dashed lines is a double bond;

with a fragment of formulae V-1 or V-2:

Formula V-1

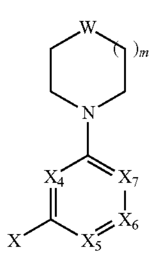

-continued

Formula V-2

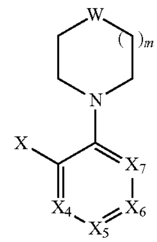

wherein X is a halogen selected from F, Br, Cl and I;

$X_4$, $X_5$, $X_6$, and $X_7$ are independently selected from $CR_3$ and N;

$R_3$ is selected from —H, —Cl, —Br, —I, —F, —$CF_3$, —OH, —CN, —$NO_2$, —$NH_2$, —NH($C_1$-$C_6$ alkyl), —N($C_1$-$C_6$ alkyl)$_2$, —COOH, —COO($C_1$-$C_6$ alkyl), —CO($C_1$-$C_6$ alkyl), —O($C_1$-$C_6$ alkyl), —OCO($C_1$-$C_6$ alkyl), —NCO($C_1$-$C_6$ alkyl), —CONH $C_1$-$C_6$ (alkyl), and substituted or unsubstituted $C_1$-$C_6$ alkyl;

m is 1 or 2; and

W is —O or —$NR_4$, wherein $R_4$ is selected from selected from —CO($C_1$-$C_6$ alkyl), substituted or unsubstituted $C_1$-$C_6$ alkyl, substituted or unsubstituted aryl, substituted or unsubstituted heteroaryl, substituted or unsubstituted cycloalkyl, —CO(aryl), —CO(heteroaryl), and —CO(cycloalkyl), in the presence of a Pd catalyst.

In some embodiments the Pd catalyst is selected from (DPPF)$PdCl_2$, $Pd_2(dba)_3$, $PdCl_2[P(o\text{-Tolyl})_3]_2$, $Pd(dba)_2$, and $Pd(OAc)_2$. In some embodiments, the contacting step further comprises a phosphine ligand. In some embodiments, the phosphine ligand is monodentate. In some embodiments, the phosphine ligand is bidentate. Exemplary phosphine ligands include, but are not limited to, DPPF, BINAP, and rac-BINAP. In some embodiments, the contacting step further comprises a base. In some embodiments, the base is inorganic. In some embodiments, the base is NaOtBu. In some embodiments, the contacting step of carried out neat (i.e., without solvent). In some embodiments, the contacting step is carried out in the presence of a solvent. In some embodiments, the solvent is a nonpolar solvent. Exemplary solvents include, but are not limited thereto, toluene, benzene, dioxane, and tetrahydrofuran. In some embodiments, the contacting step is carried out at elevated temperatures. In some embodiments, the contacting step is carried out at 50, 55, 60, 65, 70, 75, 80, 85, 90, 95, 100, 105, or 100° C.

In some embodiments, methods for preparing the disclosed compounds comprises: contacting a fragment of formulae IV:

Formual (IV)

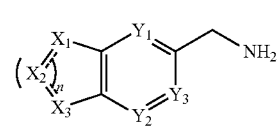

with a fragment of formula VI-1 or VI-2:

Formula VI-1

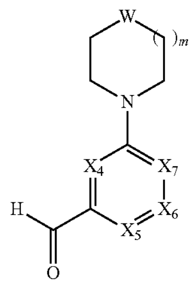

Formula VI-2

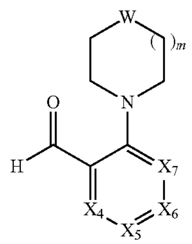

wherein $X_1$, $X_2$, $X_3$, $X_4$, $X_5$, $X_6$, $X_7$, $Y_1$, $Y_2$, $Y_3$ n, m, and W are defined as above, in the presence of a reducing agent.

In some embodiments, the reducing agent can be any reducing agent applicable for reductive amination chemistry. Exemplary reducing agents include, but are not limited to, borohydride and/or aluminum hydrides. In some embodiments, the reducing agent is a borohydride. In some embodiments, the reducing agent is sodium borohydride. In some embodiments, the contacting step is carried out neat. In some embodiments, the contacting step is carried out in a solvent. Exemplary solvents include, but are not limited thereto, alcoholic solvents (e.g., methanol, ethanol, isopropanol), chlorinated solvents (e.g., dichloromethane), and/or ether solvents (e.g., tetrahydrofuran). In some embodiments, the contacting step is carried out below room temperature. In some embodiments, the contacting step is carried out at elevated temperatures.

In some embodiments, methods for preparing the disclosed compounds comprises: contacting a fragment of formula IV:

Formual (IV)

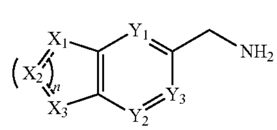

with a fragment of formulae VII-1 or VII-2:

Formula VII-1

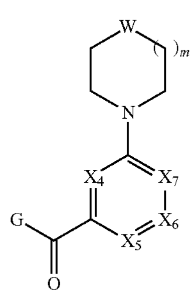

-continued

Formula VII-2

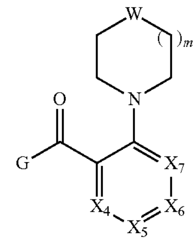

wherein $X_1$, $X_2$, $X_3$, $X_4$, $X_5$, $X_6$, $X_7$, $Y_1$, $Y_2$, $Y_3$, n, m, and W are defined as above; and G is —F, —Cl, —Br, —OH, —$OCH_3$, or —$OCH_2CH_3$;

in the presence of base.

In some embodiments the base is organic (pyridine and/or trimethylamine). In some embodiments, the base is inorganic (e.g., potassium/sodium carbonate and/or potassium/sodium bicarbonate). In some embodiments, the method further comprises a coupling agent such as DCC and/or EDCI but is not limited thereto. In some embodiments, the contacting step is carried out neat. In some embodiments, the contacting step is carried out in the presence of a solvent. Exemplary solvents include, but are not limited to THF, DCM, ACN and/or DMSO. In some embodiments, the contacting step is carried out at room temperature. In some embodiments, the contacting step is carried out elevated temperatures.

F. Compositions

The presently disclosed compounds can be formulated into pharmaceutical compositions along with a pharmaceutically acceptable carrier.

Compounds as disclosed herein can be formulated in accordance with standard pharmaceutical practice as a pharmaceutical composition. According to this aspect, there is provided a pharmaceutical composition comprising a compound as disclosed herein in association with a pharmaceutically acceptable diluent or carrier.

A typical formulation is prepared by mixing a compound as disclosed herein and a carrier, diluent, or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound as disclosed herein or pharmaceutical composition thereof) or aid in the manufacturing of the pharmaceutical product (i.e., medicament).

The formulations may be prepared using conventional dissolution and mixing procedures. For example, the bulk drug substance (i.e., compound as disclosed herein or stabilized form of the compound (e.g., complex with a cyclodextrin derivative or other known complexation agent) is dissolved in a suitable solvent in the presence of one or more of the excipients described above. The compound is typically formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound as disclosed herein having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound as disclosed herein can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds may be prepared. Suitable examples of sustained-release preparations include semipermeable matrices of solid hydrophobic polymers containing a compound as disclosed herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound as disclosed herein suitable for oral administration may be prepared as discrete units such as pills, capsules, cachets or tablets each containing a predetermined amount of a compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds as disclosed herein intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 1 to 500 μg of the active ingredient per milliliter of solution in order that infusion of a suitable volume at a rate of about 10 mL/hr to about 50 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

G. Methods of Treating

The compounds and compositions disclosed herein can also be used in methods for treating various diseases and/or disorders that have been identified as being associated with a dysfunction in RNA expression and/or function, or with the expression and/or function of the protein that is produced from an mRNA, or with a useful role of switching the conformation of an RNA using a small molecule, or with changing the native function of a riboswitch as a way inhibiting growth of an infectious organism. As such, the methods of the current disclosure are directed to treating a disease or disorder that is associated with a dysfunction in RNA expression and/or function, or creating a new switchable therapeutic. See, for example, US. Patent Application Publication No. 2018/010146, which is hereby incorporated by reference it its entirety. As such, in some embodiments, methods for treating a disease or disorder as disclosed herein (e.g., that is associated with a dysfunction in RNA expression and/or function) comprises administering to a subject in need thereof a dose of a therapeutically effective amount of a compound and/or composition as disclosed herein.

A dysfunction in RNA expression is characterized by an overexpression or underexpression of one or more RNA molecule(s). In some embodiments, the one or more RNA molecule(s) are related to promoting the disease and/or disorder to be treated. In some embodiments, the RNA molecule(s) are characterized as being part of the machinery of healthy cells and thus would prevent and/or ameliorate the disease and/or disorder to be treated. In some embodiments, the disease or disorder to be treated is associated with a dysfunction in RNA function related to transcription, processing, and/or translation. In some embodiments, the disease or disorder to be treated is associated with an inaccurate expression of proteins as a result of dysfunctional RNA molecule function. In some embodiments, the disease or disorder to be treated is associated with a dysfunction of the RNA function related to gene expression. In some embodiments, the disease or disorder is a disease or disorder where it is desired to lower protein expression by binding a molecule to the mRNA. In some embodiments, the disease is advantageously treated by a therapy that can be switched on or off using a small molecule. For example, in some embodiments, the disease or disorder is a genetic diseases, where it is desired to have the ability to switch expression of a therapeutic gene on or off.

The diseases and disorders to be treated include, but are not limited to, degenerative disorders, cancer, diabetes, autoimmune disorders, cardiovascular disorders, clotting disorders, diseases of the eye, infectious disease, and diseases caused by mutations in one or more genes.

Exemplary degenerative diseases include, but are not limited to, Alzheimer's disease (AD), Amyotrophic lateral sclerosis (ALS, Lou Gehrig's disease), Cancers, Charcot-Marie-Tooth disease (CMT), Chronic traumatic encephalopathy, Cystic fibrosis, Some cytochrome c oxidase deficiencies (often the cause of degenerative Leigh syndrome), Ehlers-Danlos syndrome, Fibrodysplasia ossificans progressive, Friedreich's ataxia, Frontotemporal dementia (FTD), Some cardiovascular diseases (e.g. atherosclerotic ones like coronary artery disease, aortic stenosis etc.), Huntington's disease, Infantile neuroaxonal dystrophy, Keratoconus (KC), Keratoglobus, Leukodystrophies, Macular degeneration (AMD), Marfan's syndrome (MFS), Some mitochondrial myopathies, Mitochondrial DNA depletion syndrome, Multiple sclerosis (MS), Multiple system atrophy, Muscular dystrophies (MD), Neuronal ceroid lipofuscinosis, Niemann-Pick diseases, Osteoarthritis, Osteoporosis, Parkinson's disease, Pulmonary arterial hypertension, All prion diseases (Creutzfeldt-Jakob disease, fatal familial insomnia etc.), Progressive supranuclear palsy, Retinitis pigmentosa (RP), Rheumatoid arthritis, Sandhoff Disease, Spinal muscular atrophy (SMA, motor neuron disease), Subacute sclerosing panencephalitis, Tay-Sachs disease, and Vascular dementia (might not itself be neurodegenerative, but often appears alongside other forms of degenerative dementia).

Exemplary cancers include, but are not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

Exemplary autoimmune disorder include, but are not limited to, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticarial, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, HI, Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

Exemplary cardiovascular disorders include, but are not limited to, coronary artery disease (CAD), angina, myocardial infarction, stroke, heart attack, heart failure, hypertensive heart disease, theumatic heart disease, cardiomyopathy, abnormal heart rythyms, congenital heart disease, valvular heart disease, carditis, aortic aneurysms, peripheral artery disease, thromboembolic disease, and venous thrombosis.

Exemplary clotting disorders include, but are not limited to, hemophilia, von Willebrand diseases, disseminated intravascular coagulation, liver disease, overdevelopment of circulating anticoagulants, vitamin K deficiency, platelet disfunction, and other clotting deficiencies.

Exemplary eye diseases include, but are not limited to, macular degeneration, bulging eye, cataract, CMV retinitis, diabetic macular edema, glaucoma, keratoconus, ocular hypertension, ocular migraine, retinoblastoma, subconjunctival hemorrhage, pterygium, keratitis, dry eye, and corneal abrasion.

Exemplary infectious diseases include, but are not limited to, Acute Flaccid Myelitis (AFM),Anaplasmosis, Anthrax, Babesiosis, Botulism, Brucellosis, Campylobacteriosis, Carbapenem-resistant Infection (CRE/CRPA), Chancroid, Chikungunya Virus Infection (Chikungunya), Chlamydia, Ciguatera (Harmful Algae Blooms (HABs)), *Clostridium difficile* Infection, *Clostridium perfringens* (Epsilon Toxin), Coccidioidomycosis fungal infection (Valley fever), COVID-19 (Coronavirus Disease 2019), Creutzfeldt-Jacob Disease, transmissible spongiform encephalopathy (CJD), Cryptosporidiosis (Crypto), Cyclosporiasis, Dengue, 1,2,3,4 (Dengue Fever), Diphtheria, *E. coli* infection, Shiga toxin-producing (STEC), Eastern Equine Encephalitis (EEE), Ebola Hemorrhagic Fever (Ebola), Ehrlichiosis, Encephalitis, Arboviral or parainfectious, Enterovirus Infection, Non-Polio (Non-Polio Enterovirus), Enterovirus Infection, D68 (EV-D68), Giardiasis (Giardia), Glanders, Gonococcal Infection (Gonorrhea), Granuloma inguinale, Haemophilus Influenza disease, Type B (Hib or H-flu), Hantavirus Pulmonary Syndrome (HPS), Hemolytic Uremic Syndrome (HUS), Hepatitis A (Hep A), Hepatitis B (Hep B), Hepatitis C (Hep C), Hepatitis D (Hep D), Hepatitis E (Hep E), Herpes, Herpes Zoster, zoster VZV (Shingles), Histoplasmosis infection (Histoplasmosis), Human Immunodeficiency Virus/AIDS (HIV/AIDS), Human Papillomavirus (HPV), Influenza (Flu), Lead Poisoning, Legionellosis (Legionnaires Disease), Leprosy (Hansens Disease), Leptospirosis, Listeriosis (Listeria), Lyme Disease, Lymphogranuloma venereum infection (LGV), Malaria, Measles, Melioidosis, Meningitis, Viral (Meningitis, viral), Meningococcal Disease, Bacterial (Meningitis, bacterial), Middle East Respiratory Syndrome Coronavirus (MERS-CoV), Mumps, Norovirus, Paralytic Shellfish Poisoning (Paralytic Shellfish Poisoning, Ciguatera), Pediculosis (Lice, Head and Body Lice), Pelvic Inflammatory Disease (PID), Pertussis (Whooping Cough), Plague; Bubonic, Septicemic, Pneumonic (Plague), Pneumococcal Disease (Pneumonia), Poliomyelitis (Polio), Powassan, Psittacosis (Parrot Fever), Pthiriasis (Crabs; Pubic Lice Infestation), Pustular Rash diseases (Small pox, monkeypox, cowpox), Q-Fever, Rabies, Ricin Poisoning, Rickettsiosis (Rocky Mountain Spotted Fever), Rubella, Including congenital (German Measles), Salmonellosis gastroenteritis (Salmonella), Scabies Infestation (Scabies), Scombroid, Septic Shock (Sepsis), Severe Acute Respiratory Syndrome (SARS), Shigellosis gastroenteritis (Shigella), Smallpox, Staphyloccal Infection, Methicillin-resistant (MRSA), Staphylococcal Food Poisoning, Enterotoxin-B Poisoning (Staph Food Poisoning), Staphylococcal Infection, Vancomycin Intermediate (VISA), Staphylococcal Infection, Vancomycin Resistant (VRSA), Streptococcal Disease, Group A (invasive) (Strep A (invasive)), Streptococcal Disease, Group B (Strep-B), Streptococcal Toxic-Shock Syndrome, STSS, Toxic Shock (STSS, TSS), Syphilis (primary, secondary, early latent, late latent, congenital), Tetanus Infection, tetani (Lock Jaw), Trichomoniasis (Trichomonas infection), Trichonosis Infection (Trichinosis), Tuberculosis (TB), Tuberculosis (Latent) (LTBI), Tularemia (Rabbit fever), Typhoid Fever (Group D), Typhus, Vaginosis, bacterial (Yeast Infection), Vaping-Associated Lung Injury (e-Cigarette Associated Lung Injury), Varicella (Chickenpox), Vibrio cholerae (Cholera), Vibriosis (Vibrio), Viral Hemorrhagic Fever (Ebola, Lassa, Marburg), West Nile Virus, Yellow Fever, Yersenia (Yersinia), and Zika Virus Infection (Zika).

EXAMPLES

Example 1: Construct Design and Preparation of RNA

The screening construct was designed to allow incorporation of a wide variety of one or more internal target RNA motifs. Two motifs were present in the construct: the TPP riboswitch domain' and a pseudoknot from the 5'-UTR of the dengue virus[26]. The design for the complete construct sequence, including structure cassettes, the RNA barcode helix, and the two test RNA structures (separated by a six-nucleotide linker), was evaluated using RNA structure[39]. To reduce the likelihood of that the two test structures would interact, a small number of sequence alterations were made to discourage misfolded structures predicted by RNA structure while retaining the native fold (FIG. 7). The structure of the final construct was confirmed by SHAPE-MaP.

RNA barcodes were designed to fold into self-contained hairpins (FIG. 7). All possible permutations of RNA barcodes were computed and folded in the context of the full construct sequence, and any barcodes that had the potential to interact with another part of the RNA construct were removed from the set. Barcoded constructs were probed by SHAPE-MaP using the "no ligand" protocol and folded using RNA structure with SHAPE reactivity constraints to confirm that barcode helices folded into the desired self-contained hairpins.

Preparation of RNA

DNA templates (Integrated DNA Technologies) for in vitro transcription encoded the target construct sequence (containing the dengue pseudoknot sequence, single stranded linker, and the TPP riboswitch sequence) and flanking structure cassettes[25]:

```
                                        (SEQ ID NO: 1)
5'-GTGGG CACTT CGGTG TCCAC ACGCG AAGGA AACCG CGTGT

CAACT GTGCA ACAGC TGACA AAGAG ATTCC TAAAA CTCAG

TACTC GGGGT GCCCT TCTGC GTGCA GGCTG AGAAA TACCC

GTATC ACCTG ATCTG GATAA TGCCA GCGTA GGGAA GTGCT

GGATC CGGTT CGCCG GATCA ATCGG GCTTC GGTCC GGTTC-

3'.
```

The primer binding sites are underlined. Forward PCR primers containing unique RNA barcodes and the T7 promoter sequence were used to individually add RNA barcodes to each of 96 constructs in individual PCR reactions. A sample forward primer sequence, with barcode nucleotides in bold and the primer binding site underlined, is:

```
                                        (SEQ ID NO: 2)
5'-GAAAT TACGA CTCAC TATAG GTCGC GAGTA ATCGC GACCG
GCGCT AGAGA TAGTG CCGTG GGCAC TTCGG TGTC-3'.
```

DNA was amplified by PCR using 200 μM dNTP mix (New England Biolabs), 500 nM forward primer, 500 nM reverse primer, 1 ng DNA template, 20% (v/v) Q5 reaction buffer, and 0.02 U/μL Q5 hot-start high-fidelity polymerase (New England Biolabs) to create templates for in vitro transcription. DNA was purified (PureLink Pro 96 PCR Purification Kit; Invitrogen) and quantified (Quant-iT dsDNA high sensitivity assay kit; Invitrogen) on a Tecan Infinite M1000 Pro microplate reader.

In vitro transcription was carried out in 96-well plate format with each well containing 100 μL total reaction volume. Each well contained 5 rnM NTPs (New England Biolabs), 0.02 U/μL inorganic pyrophosphatase (yeast, New England Biolabs), 0.05 mg/mL T7 polymerase in 25 mM $MgCl_2$, 40 mM Tris, pH 8.0, 2.5 mM spermidine, 0.01% Triton, 10 mM DTT, and 200-800 nM of a uniquely barcoded DNA template (generated by PCR). Reactions were incubated at 37° C. for 4 hours; then treated with TurboDNase (RNase-free, Invitrogen) at a final concentration of 0.04 U/μL; incubated at 37° C. for 30 min; followed by a second DNase addition to a total final concentration of 0.08 U/μL and an additional 30-minute incubation at 37° C. Enzymatic reactions were halted by the addition of EDTA to a final concentration of 50 mM and placed on ice. RNA was purified (Agencourt RNAclean XP magnetic beads; Beckman Coulter) in a 96-well format and resuspended in 10 mM Tris pH 8.0, 1 mM EDTA. RNA concentrations were quantified (Quant-iT RNA broad range assay kit; Invitrogen) on a Tecan Infinite M1000 Pro microplate reader, and RNAs in each well were individually diluted to 1 pmol/μL. RNA was stored at −80° C.

Example 2: Chemical Modification and Screening of Small-Molecule Fragments

Fragments were obtained as a fragment screening library from Maybridge, which was a subset of their Ro3 diversity fragment library and contained 1500 compounds dissolved in DMSO at 50 mM. Most of these compounds adhere to the "rule of three" for fragment compounds; having a molecular mass<300 Da, containing ≤3 hydrogen bond donors and ≤3 hydrogen bond acceptors, and ClogP≤3.0. All compounds used for ITC, with the exception of those listed in Example 5, were purchased from Millipore-Sigma and used without further purification. Screening experiments were carried out in 25 μL in 96-well plate format on a Tecan Freedom Evo-150 liquid handler equipped with an 8-channel air displacement pipetting arm, disposable filter tips, robotic manipulator arm, and an EchoTherm RIC20 remote controlled heating/cooling dry bath (Torrey Pines Scientific). Liquid handler programs used for screening are available upon request.

For the first-fragment-ligand screen, 5 pmol of RNA per well were diluted to 19.6 L in RNase-free water on a 4° C. cooling block. The plate was heated at 95° C. for 2 minutes, immediately followed by snap cooling at 4° C. for 5 minutes.

To each well was added 19.6 μL of 2× folding buffer (final concentrations 50 mM HEPES pH 8.0, 200 mM potassium acetate, and 10 mM $MgCl_2$), and plates were incubated at 37° C. for 30 minutes. For the second-fragment-ligand screen, 24.3 μL of folded RNA per well were added to 2.7 μL of primary binding fragment in DMSO to a final concentration of 10× the Ka of the fragment, and samples were incubated at 37° C. for 10 minutes. To combine the target RNA with fragment, 24.3 μL of RNA solution or RNA plus primary binding fragment were added to wells containing 2.7 μL of 10× screening fragments (in DMSO to yield a final fragment concentration of 1 mM). Solutions were mixed thoroughly by pipetting and incubated for 10 minutes at 37° C. For SHAPE probing, 22.5 μL of RNA-fragment solution from each well of the screening plate were added to 2.5 μL of 10× SHAPE reagent in DMSO on a 37° C. heating block and rapidly mixed by pipetting to achieve homogenous distribution of the SHAPE reagent with the RNA. After the appropriate reaction time, samples were placed on ice. For the first-fragment screen, 1-methyl-7-nitroisatoic anhydride (1M7) was used as the SHAPE reagent at a final concentration of 10 mM with reaction for 5 minutes. For the second-fragment screen, 5-nitroisatoic anhydride (5NIA)[40] was used as the SHAPE reagent at a final concentration of 25 mM with reaction for 15 minutes. Excess fragments, solvent, and hydrolyzed SHAPE reagent were removed using AutoScreen-A 96-Well Plates (GE Healthcare Life Sciences), and 5 μL of modified RNA from each well of a 96-well plate were pooled into a single sample per plate for sequencing library preparation.

Each screen consisted of 19 fragment test plates, two plates containing a distribution of positive (fragment 2, final concentration 1 mM) and negative (solvent, DMSO) controls, and one negative SHAPE control plate treated with solvent (DMSO) instead of SHAPE reagent. For hit validation experiments, well locations of each hit fragment were changed to control for well location and RNA barcode effects. Plate maps for both the primary and secondary screens were available as well.

Once screening of test fragments is complete, statistical tests are carried out to identify differences in modification rates of a given nucleotide. Specifically, the screening analysis requires statistical comparison of the modification rate of a given nucleotide in the presence of a fragment as compared to its absence. For each nucleotide, the number of modifications in a given reaction is a Poisson process with a known variance; the statistical significance of the observed difference in modification rates between two samples can therefore be ascertained by performing the Comparison of Two Poisson Counts test[31]. That is, if $m_1$ modifications of a tested nucleotide were counted among $n_1$ reads in sample 1 and $m_2$ modifications were counted among $n_2$ reads in sample 2, the tested null hypothesis predicts that among all the counted modifications ($m_1+m_2$), the proportion of modifications in sample 1 will be $p_1=n_1/(n_1+n_2)$. The Z-test of this hypothesis is:

$$Z_p = \frac{m_1 - p_1(m_1+m_2) + 0.5}{\sqrt{p_1(1-p_1)(m_1+m_2)}}$$

$$Z_n = \frac{m_1 - p_1(m_1+m_2) - 0.5}{\sqrt{p_1(1-p_1)(m_1+m_2)}}$$

$$Z = \min(|Z_p|, |Z_n|)$$

If the Z value exceeds a specified significance threshold, the tested nucleotide is taken to be statistically significantly affected by the presence of the test fragment.

Next, for each fragment, the Z-test has to be performed on a large number of nucleotides comprising the RNA sequence, increasing the probability of false positives. While the numbers of false positive assignments of SHAPE reactivity per nucleotide can be minimized by raising Z significance threshold, this approach would reduce the sensitivity of the screen (meaning it would reduce the ability to detect weaker binding ligands). To reduce the number of Z-tests performed, such tests were applied only to nucleotides in the region of interest, rather than to all nucleotides in the RNA screening construct. For the dengue motif of the RNA, the region of interest was positions 59-110; for the TPP motif, the region of interest was positions 100-199. The number of Z-tests was reduced further by omitting nucleotides with low modification rates in both samples. The threshold for considering a nucleotide to have a low modification rate was set at 25% of the plate-average modification rate, which was computed over all nucleotides in all 96 wells of a given plate. Z-tests were performed only on those nucleotides that, in at least one of the two compared samples, had the modification rate exceeding this 25% threshold.

Ideally, the only difference between conditions in two compared samples would be the presence of a fragment in one sample but not in the other. Testing negative-control samples against each other can be used to gauge the prevalence of uncontrolled factors that might introduce across-sample variability in nucleotide modification rates. For example, if the Z significance threshold is set at 2.7, in the absence any such factors, the Z-test applied to pairs of negative-control (no fragment) samples should, theoretically, identify differentially reactive nucleotides with a probability P=0.0035. However, when the Z-test was applied to pairs of negative-control samples selected at random from the 587 negative-control samples tested in the primary screen, the actual probability was 90 times higher with P=0.32. Thus, there was statistically significant variability in SHAPE reactivities at individual nucleotides in the absence of fragments.

Although the majority of replicates shared essentially the same profiles, there were a substantial number of replicates with dissimilar profiles; some coefficients of determination were as low as 0.85. Applying the Z-test to dissimilar negative-control samples generated large numbers of cases were nucleotides were falsely classified as differentially reactive. To avoid this outcome, each sample was compared to the five most highly correlated negative-control samples. Z-tests applied to such selective pairs of negative controls with a Z significance threshold of 2.7, resulted in identification of differentially reactive nucleotides with a probability P=0.067.

This probability is about 20 times higher than the theoretical P=0.0035 indicating that there is variability in sample processing. Some of this variability scales equally across the reactivities of all the nucleotides of all RNAs in a sample. This variability can be removed by scaling down the overall reactivity in the more reactive sample so as to match the overall reactivity in the less reactive sample. Such scaling was performed by (i) computing for each nucleotide in the RNA sequence the ratio of its modification rate in the more reactive sample to that in the less reactive sample and (ii) dividing the modification rates of all the nucleotides in the more reactive sample by the median of the ratios obtained in step (i). Such scaling of correlation-maximized pairs of negative-control wells reduced the probability of finding nucleotide hits to P=0.030, 9-fold higher than the theoretical probability. Thus, false-positive identification of fragments will occur, as indeed occurs in all high-throughput screening assays, and actual fragment hits from non-ligand variations were distinguished by replicate SHAPE validation and by direct ligand binding measurement using ITC.

Since an effective ligand is expected to affect modification rates of multiple nucleotides in the target RNA, a fragment was recognized as a hit only if the number of nucleotides with reactivity different from that in the negative control exceeded a defined threshold, which was set to 2. Second, when looking for relatively robust effects of fragments on the RNA, small relative differences in reactivity of a nucleotide, even if statistically significant, were excluded from the total count of differentially reactive nucleotides. In practice, the minimal accepted difference was set to 20% of the average:

$$|r_1-r_2|/(r_1+r_2)/2=0.2,$$

where $r_1$ and $r_2$ are the nucleotide modification rates in two samples. Third, a given sample was tested against the five negative-control samples with which it was most highly correlated. All five tests were required to find the test sample altered relative to the negative-control sample.

Finally, the sensitivity and specificity of the screen were controlled by the choice of Z significance threshold. Evaluation of samples containing fragments and all negative-control samples was performed at multiple Z significance threshold settings. For each such setting, the false-positive fraction (FPF) was computed as a fraction of the negative-control samples that were found to be altered, and the ligand fraction (LF) was estimated by subtracting FPF from the fraction of altered samples containing a fragment. The balance between LF and FPF was quantified by their ratio, LF/FPF. The best balance (LF/FPF≈1.3) for the TPP riboswitch RNA was achieved with Z significance threshold in the range between 2.5 and 2.7, at which 0.022>FPF>0.014. For the dengue pseudoknot, the best balance (LF/FPF≈4) was achieved with Z significance threshold in the range between 2.5 and 2.65, at which 0.007>FPF>0.005.

Example 3: Library Preparation and Sequencing

Reverse transcription was performed on pooled, modified RNA in a 100 μL volume. To 71 μL of pooled RNA was added 6 μL reverse transcription primer to achieve a final concentration of 150 nM primer, and the sample was incubated at 65° C. for 5 minutes and then placed on ice. To this solution, 6 μL 10× first-strand buffer (500 mM Tris pH 8.0, 750 mM KCl), 4 μL 0.4 M DTT, 8 μL dNTP mix (10 mM each), and 15 μL 500 mM $MnCl_2$ were added, and the solution was incubated at 42° C. for 2 minutes before adding 8 μL SuperScript II Reverse Transcriptase (Invitrogen). The reaction was incubated at 42° C. for 3 hours, followed by a 70° C. heat inactivation for 10 minutes before being placed on ice. The resulting cDNA product was purified (Agencourt RNAClean magnetic beads; Beckman Coulter), eluted into RNase-free water, and stored at −20° C. The sequence of the reverse transcription primer was 5'-CGGGC TTCGG TCCGG TTC-3' (SEQ ID NO:3).

DNA libraries were prepared for sequencing using a two-step PCR reaction to amplify the DNA and to add the necessary TruSeq adapters[24]. DNA was amplified by PCR using 200 μM dNTP mix (New England Biolabs), 500 nM forward primer, 500 nM reverse primer, 1 ng cDNA or double-stranded DNA template, 20% (v/v) Q5 reaction buffer (New England Biolabs), and 0.02 U/μL Q5 hot-start high-fidelity polymerase (New England Biolabs). Excess unincorporated dNTPs and primers were removed by affinity purification (Agencourt AmpureXP magnetic beads; Beckman Coulter; at a 0.7:1 sample to bead ratio). DNA libraries were quantified (Qubit dsDNA High Sensitivity assay kit; Invitrogen) on a Qubit fluorometer (Invitrogen), checked for quality (Bioanalyzer 2100 on-chip electrophoresis instrument; Agilent), and sequenced on an Illumina NextSeq 550 high-throughput sequencer.

The SHAPE-MaP library preparation amplicon-specific forward primer was (SEQ ID NO: 4)
5'-CCCTA CACGA CGCTC TTCCG ATCTN NNNNG GCCTT CGGGC CAAGG A-3'.

The SHAPE-MaP library preparation amplicon-specific reverse primer was (SEQ ID NO: 5)
5'-GACTG GAGTT CAGAC GTGTG CTCTT CCGAT CTNNN NNTTG AACCG GACCG AAGCC CGATT T-3'.

The sequences overlapping the RNA screening construct are underlined.

Example 4: Isothermal Titration Calorimetry

ITC experiments were performed using a Microcal PEAQ-ITC automated instrument (Malvern Analytical) under RNase-free conditions[41]. In vitro transcribed RNA was exchanged into folding buffer containing 100 mM CHES, pH 8.0, 200 mM potassium acetate, and 3 mM $MgCl_2$ using centrifugal concentration (Amicon Ultra centrifugal filters, 10K MWCO, Millipore-Sigma). Ligands were dissolved into the same buffer (to minimize heat of mixing upon addition of ligand to RNA) at a concentration 10-20 times the desired experimental concentration of RNA. RNA concentration was quantified (Nanodrop UV-VIS spectrometer; ThermoFisher Scientific), diluted to 1-10 times the expected Ka in buffer, and the diluted RNA was re-quantified to confirm the final experimental RNA concentration. The RNA, diluted in folding buffer, was heated at 65° C. for 5 minutes, placed on ice for 5 minutes, and allowed to fold at 37° C. for 15 minutes. If needed, the primary binding ligand (for example, 2) was pre-bound to the RNA by adding 0.1 volume at 10 times the desired final concentration of the bound ligand, followed by incubation at room temperature for 10 minutes.

Each ITC experiment involved two runs: one in which the ligand was titrated into RNA (the experimental trace) and one in which the same ligand was titrated into buffer (the control trace). ITC experiments were performed using the following parameters: 25° C. cell temperature, 8 μCal/sec reference power, 750 RPM stirring speed, high feedback mode, 0.2 μL initial injection, followed by 19 injections of 2 μL. Each injection required 4 seconds to complete, and there was a 180-second spacing between injections.

ITC data was analyzed using MicroCal PEAQ-ITC Analysis Software (Malvern Analytical). First, the baseline for each injection peak was manually adjusted to resolve any incorrectly selected injection endpoints. Second, the control trace was subtracted from the experimental trace by point-to-point subtraction. Third, a least-squares regression line was fit to the data using the Levenberg-Marquardt algorithm.

In the case of weakly binding ligands (>500 μM), N was manually set to 1.0 to enable fitting of low c-value curves.

Example 5: Chemical Synthesis of Test Compounds 35, 36, 37, 38, 39 and 40

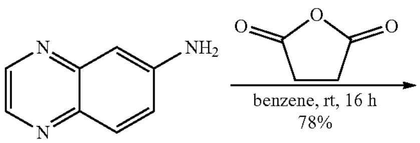

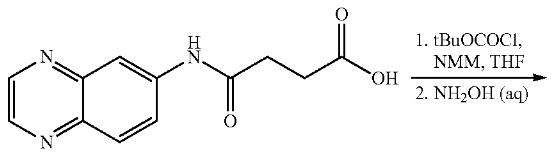

S19

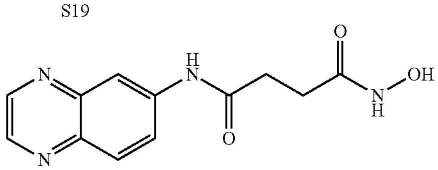

35

Compound 35: 3-C linked hydroxamic acid 35 was prepared from carboxylic acid S19 via a mixed anhydride intermediate by reacting with aqueous hydroxylamine. The acid S19 was accessed by treating quinoxalin-6-amine with cyclized anhydride dihydrofuran-2,5-dione.

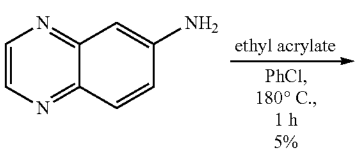

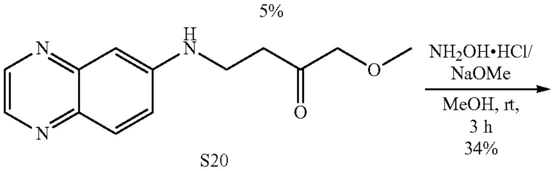

S20

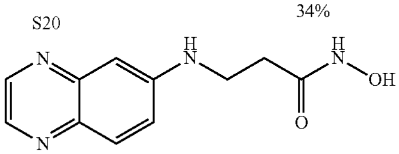

36

Compound 36: The 2-C linked analog 36 was obtained from the corresponding ester S20 by reacting with hydroxylamine formed in situ. Ester S20 was made via Michael addition of quinoxalin-6-amine with ethyl acrylate.

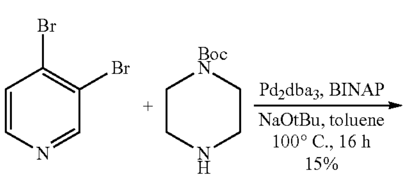

-continued

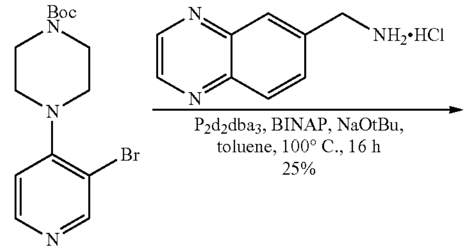

S21

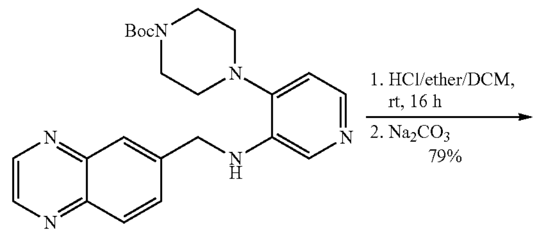

S22

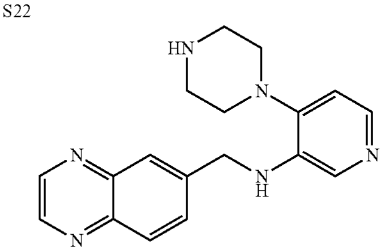

37

Compound 37: The Buchwald-Hartwig reaction was used for the synthesis of intermediate S21 and S22. Protecting group (Boc) removal was achieved with HCl in ether, followed by further treatment with $Na_2CO_3$ to give 37.

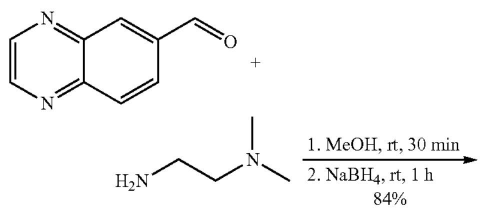

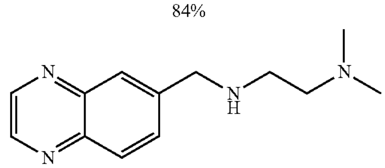

38

Compound 38: Imine formation and subsequent sodium borohydride reduction of quinoxaline-6-carbaldehyde and diamine to afford 38.

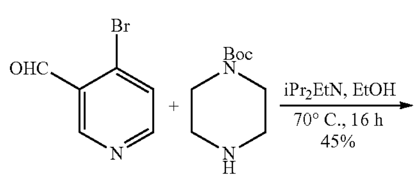

-continued

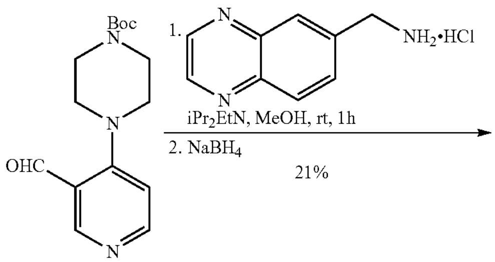

S23

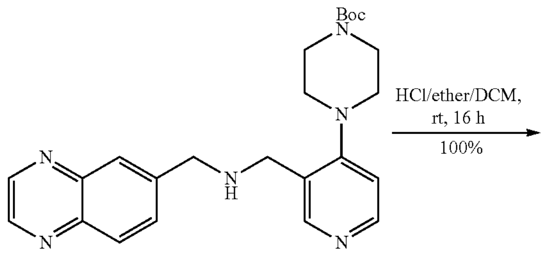

S24

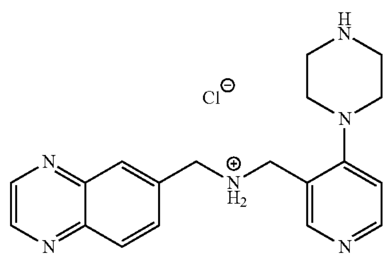

39

Compound 39: Imine formation and subsequent sodium borohydride reduction using quinoxalin-6-ylmethanamine hydrochloride and aldehyde S23, prepared via $S_NAr$ reaction afforded intermediate S24, which after (Boc) deprotection with HCl gave 39.

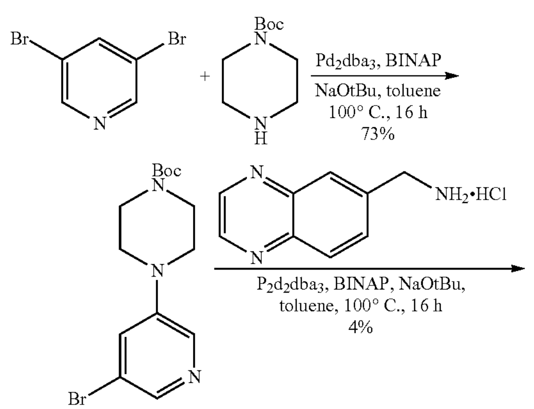

S25

-continued

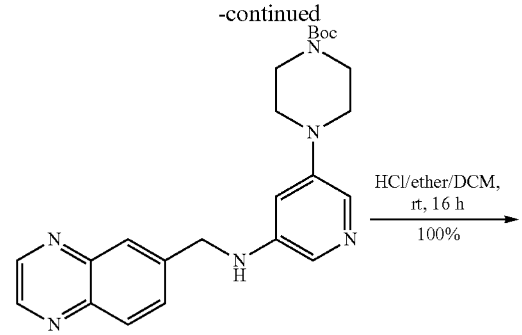

S26

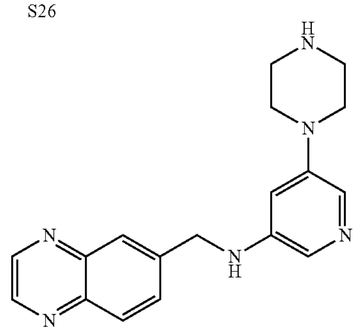

HCl

40

Compound 40: The less constrained analog 40 was made with two Buchwald-Hartwig reactions with 3,5-dibromopyridine, followed by (Boc) deprotection with HCl.

Example 6: X-Ray Crystallography

To assess whether structural variants of 2 would be good binding candidates for the TPP riboswitch, Compound 17 was investigated in X-ray crystallography studies. TPP riboswitch RNA was prepared by in vitro transcription as described[27]. TPP riboswitch RNA (0.2 mM) and 17 (2 mM) were heated in a buffer containing 50 mM potassium acetate (pH 6.8) and 5 mM $MgCl_2$ at 60° C. for 3 min, snap cooled in crushed ice, and incubated at 4° C. for 30 min prior to crystallization. For crystallization, 1.0 μl of the RNA-17 complex was mixed with 1.0 μL of reservoir solution containing 0.1 M sodium acetate (pH 4.8), 0.35 M ammonium acetate, and 28% (v/v) PEG4000. Crystallization was performed at 291K by hanging drop vapor diffusion over 2 weeks. The crystals were cryoprotected in mother liquor supplemented with 15% of glycerol prior to snap freezing in liquid nitrogen. Data were collected at the 17-1D-2 (FMX) beamline at NSLS-II (Brookhaven National Laboratory) at 0.9202 Å wavelength. Data were processed with HKL200043. The structure was solved by molecular replacement using Phenix44 and the 2GDI riboswitch RNA structure. The structure was refined in Phenix. Organic ligand, water molecules and ions were added at the late stages of refinement based on Fo-Fc and 2Fo-Fc electron density maps.

Results showed that Compound 17 binds the TPP riboswitch in a fashion similar to the thiamine moiety of the TPP ligand, stacking between G42 and A43 in the J3/2 junction (FIG. 3)[27,28]. 17 forms three hydrogen bonds with the RNA: one each to the ribose and Watson-Crick face of G40 and one to the ribose of G19. Relative to the RNA in complex with the native TPP ligand, there is a significant change in local RNA structure. In the 17-bound structure, G72 is flipped into the binding site where the pyrophosphate moiety of the TPP ligand resides. This binding mode is consistent with prior work that visualized a flipped-in G72 orientation for fragments bound in the thiamine sub-site of the riboswitch binding pocket[17,34]. Consistent with the SAR analysis, the orientation of the C-6 substituent appears to be relatively unhindered by interactions with the RNA, implying that this vector would make a good candidate for fragment elaboration.

REFERENCES

1. Hajduk, P. J., Huth, J. R. & Tse, C. Predicting protein druggability. *Drug Discov. Today* 10, 1675-1682 (2005).
2. Vukovic, S. & Huggins, D. J. Quantitative metrics for drug-target ligandability. *Drug Discov. Today* 23, 1258-1266 (2018).
3. Batey, R. T., Rambo, R. P. & Doudna, J. A. Tertiary Motifs in RNA Structure and Folding. *Angew. Chem. Int. Ed.* 38, 2326-2343 (1999).
4. Warner, K. D., Hajdin, C. E. & Weeks, K. M. Principles for targeting RNA with drug-like small molecules. *Nat. Rev. Drug Discov.* 17, 547-558 (2018).
5. Sharp, P. A. The Centrality of RNA. *Cell* 136, 577-580 (2009).
6. Kozak, M. Regulation of translation via mRNA structure in prokaryotes and eukaryotes. *Gene* 361, 13-37 (2005).
7. Corbino, K. A., Sherlock, M. E., McCown, P. J., Breaker, R. R. & Stay, S. Riboswitch diversity and distribution. *RNA* 23,995-1011 (2017).
8. Cech, T. R. & Steitz, J. A. The noncoding RNA revolution—Trashing old rules to forge new ones. *Cell* 157, 77-94 (2014).
9. Parsons, C., Slack, F. J., Zhang, W. C., Adams, B. D. & Walker, L. Targeting noncoding RNAs in disease. *J. Gin. Invest.* 127, 761-771 (2017).
10. Matsui, M. & Corey, D. R. Non-coding RNAs as drug targets. *Nat. Rev. Drug Discov.* 16, 167-179 (2017).
11. Guan, L. & Disney, M. D. Recent advances in developing small molecules targeting RNA. *ACS Chem. Biol.* 7, 73-86 (2012).
12. Connelly, C M., Moon, M. & Schneekloth, J. S. The Emerging Role of RNA as a Therapeutic Target for Small Molecules. *Cell Chem. Biol.* 23,1077-1090 (2016).
13. Murray, C. W. & Rees, D. C. The rise of fragment-based drug discovery. *Nat. Chem.* 1, 187-92 (2009).
14. Doak, B. C., Norton, R. S. & Scanlon, M. J. The ways and means of fragment-based drug design. *Pharmacol. Ther.* 167, 28-37 (2016).
15. Cressina, E., Chen, L., Abell, C., Leeper, F. J. & Smith, A. G. Fragment screening against the thiamine pyrophosphate riboswitch thiM. *Chem. Sci.* 2, 157-165 (2011).
16. Moumné, R., Catala, M., Larue, V., Micouin, L. & Tisné, C. Fragment-based design of small RNA binders: Promising developments and contribution of NMR. *Biochimie* 94, 1607-1619 (2012).
17. Warner, K. D. et al. Validating fragment-based drug discovery for biological RNAs: Lead fragments bind and remodel the TPP riboswitch specifically. *Chem. Biol.* 21, 591-595 (2014).
18. Zeiger, M. et al. Fragment based search for small molecule inhibitors of HIV-1 Tat-TAR. *Bioorganic Med. Chem. Lett.* 24, 5576-5580 (2014).
19. Bottini, A. et al. Targeting Influenza A Virus RNA Promoter. *Chem. Biol. Drug Des.* 86, 663-673 (2015).
20. Hunter, C. A. & Anderson, H. L. What is cooperativity? *Angew. Chemie-Int. Ed.* 48, 7488-7499 (2009).
21. Ichihara, O., Barker, J., Law, R. J. & Whittaker, M. Compound design by fragment-linking. *Mol. Inform.* 30, 298-306 (2011).
22. Zeller, M. J., Li, K., Aube, J. & Weeks, K. M. Multisite ligand recognition and cooperativity in the TPP riboswitch RNA. *Prep.* (2019).
23. Siegfried, N. A., Busan, S., Rice, G. M., Nelson, J. A. E. & Weeks, K. M. RNA motif discovery by SHAPE and mutational profiling (SHAPE-MaP). *Nat. Methods* 11, 959-65 (2014).
24. Smola, M. J., Rice, G. M., Busan, S., Siegfried, N. A. & Weeks, K. M. Selective 2'-hydroxyl acylation analyzed by primer extension and mutational profiling (SHAPE-MaP) for direct, versatile and accurate RNA structure analysis. Nat. Proloc. 10, 1643-1669 (2015).
25. Merino, E. J., Wilkinson, K. A., Coughlan, J. L. & Weeks, K. M. RNA structure analysis at single nucleotide resolution by selective 2'-hydroxyl acylation and primer extension (SHAPE). *J. Am. Chem. Soc.* 127, 4223-4231 (2005).
26. Liu, Z.-Y. et al. Novel cis-acting element within the capsid-coding region enhances flavivirus viral-RNA replication by regulating genome cyclization. *J. ViroL* 87, 6804-18 (2013).
27. Serganov, A., Polonskaia, A., Phan, A. T., Breaker, R. R. & Patel, D. J. Structural basis for gene regulation by a thiamine pyrophosphate-sensing riboswitch. *Nature* 441, 1167-1171 (2006).
28. Edwards, T. E. & Ferré-D'Amaré, A. R. Crystal structures of the thi-box riboswitch bound to thiamine pyrophosphate analogs reveal adaptive RNA-small molecule recognition. *Structure* 14, 1459-68 (2006).
29. Thore, S., Frick, C. & Ban, N. Structural basis of thiamine pyrophosphate analogues binding to the eukaryotic riboswitch. *J. Am. Chem. Soc.* 130, 8116-8117 (2008).
30. Busan, S. & Weeks, K. M. Accurate detection of chemical modifications in RNA by mutational profiling (MaP) with ShapeMapper 2. *RNA* 24, 143-148 (2018).
31. Woolson, R. Statistical Methods for the Analysis of *Biomedical Data*. (John Wiley & Sons, 1987).
32. Jhoti, H., Williams, G., Rees, D. C. & Murray, C. W. The 'rule of three' for fragment-based drug discovery: Where are we now? *Nat. Rev. Drug Discov.* 12, 644 (2013).
33. Chen, L. et al. Probing riboswitch-ligand interactions using thiamine pyrophosphate analogues. *Org. Biomol. Chem.* 10, 5924-5931 (2012).
34. Warner, K. D. & Ferré-D'Amaré, A. R. Crystallographic analysis of TPP riboswitch binding by small-molecule ligands discovered through fragment-based drug discovery approaches. *Methods Enzymol.* 549, 221-233 (2014).
35. Codd, R. Traversing the coordination chemistry and chemical biology of hydroxamic acids. *Coord. Chem. Rev.* 252, 1387-1408 (2008).
36. Jencks, W. P. On the attribution and additivity of binding energies. *Proc. Natl. Acad. Sci. U.S.A.* 78, 4046-4050 (1981).
37. Olejniczak, E. T. et al. Stromelysin inhibitors designed from weakly bound fragments: Effects of linking and cooperativity. *J. Am. Chem. Soc.* 119, 5828-5832 (1997).
38. Borsi, V., Calderone, V., Fragai, M., Luchinat, C. & Sarti, N. Entropic contribution to the linking coefficient in fragment based drug design: A case study. *J. Med. Chem.* 53, 4285-4289 (2010).
39. Reuter, J. S. & Mathews, D. H. RNAstructure: software for RNA secondary structure prediction and analysis. *BMC Bioinformatics* 11, 129 (2010).

40. Busan, S., Weidmann, C. A., Sengupta, A. & Weeks, K. M. Guidelines for SHAPE Reagent Choice and Detection Strategy for RNA Structure Probing Studies. *Biochemistry* 58, 2655-2664 (2019).

41. Gilbert, S. D. & Batey, R. T. Monitoring RNA-ligand interactions using isothermal titration calorimetry. *Methods Mol. Biol.* 540, 97-114 (2009).

42. Turnbull, W. B. Divided We Fall? Studying low affinity fragments of ligands by ITC. *Microcal Application Notes* (2005).

43. Otwinowski, Z. & Minor, W. Processing of X-ray diffraction data collected in oscillation mode. *Methods Enzymol*. (1997). doi:10.1016/S0076-6879(97)76066-X.

44. Liebschner, D. et al. Macromolecular structure determination using X-rays, neutrons and electrons: recent developments in Phenix. *Acta Crystallogr.* 75, 861-877 (2019).

45. Hajduk, P. J. et al. Discovery of potent nonpeptide inhibitors of stromelysin using SAR by NMR. *J. Am. Chem. Soc.* 119, 5818-5827 (1997).

46. Howard, N. et al. Application of fragment screening and fragment linking to the discovery of novel thrombin inhibitors. *J. Med. Chem.* 49, 1346-1355 (2006).

47. Barker, J. J. et al. Discovery of a novel Hsp90 inhibitor by fragment linking. *ChemMedChem* 5, 1697-1700 (2010).

48. Möbitz, H. et al. Discovery of Potent, Selective, and Structurally Novel Dot1L Inhibitors by a Fragment Linking Approach. *ACS Med. Chem. Lett.* 8, 338-343 (2017).

49. Hung, A. W. et al. Application of fragment growing and fragment linking to the discovery of inhibitors of *Mycobacterium tuberculosis* pantothenate synthetase. *Angew. Chemie-Int. Ed.* 48, 8452-8456 (2009).

50. Jordan, J. B. et al. Fragment-Linking Approach Using 19F NMR Spectroscopy to Obtain Highly Potent and Selective Inhibitors of β-Secretase. *J. Med. Chem.* 59, 3732-3749 (2016).

51. Maly, D. J., Choong, I. C. & Ellman, J. A. Combinatorial target-guided ligand assembly: Identification of potent subtype-selective c-Src inhibitors. *Proc. Natl. Acad. Sci.* 97, 2419-2424 (2000).

52. Shuker, S. B., Hajduk, P. J., Meadows, R. P. & Fesik, S. W. Discovering High-Affinity Ligands for Proteins: SAR by NMR. *Science* (80-.). 274, 1531-1534 (1996).

53. Mondal, M. et al. Fragment Linking and Optimization of Inhibitors of the Aspartic Protease Endothiapepsin: Fragment-Based Drug Design Facilitated by Dynamic Combinatorial Chemistry. *Angew. Chemie-Int. Ed.* 55, 9422-9426 (2016).

54. Swayze, E. E. et al. SAR by MS: A ligand based technique for drug lead discovery against structured RNA targets. *J. Med. Chem.* 45, 3816-3819 (2002).

That which is claimed:

1. A compound with a structure of formula (III):

Formula (III)

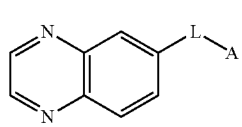

wherein

L is selected from

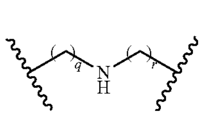, and 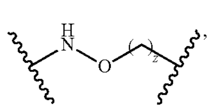, wherein q and r are independently selected from integers 0, 1, 2 and 3; and z is selected from integers 1, 2 and 3; and A is selected from

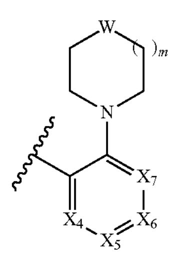,

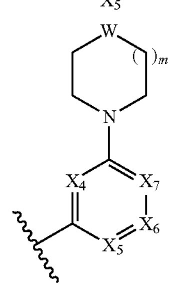, and 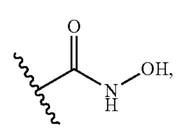

2. The compound of claim 1, wherein q and r are independently selected from integers 0, 1 and 2.

3. The compound of claim 1, wherein L is

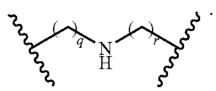

4. The compound of claim 1, wherein W is —NH.

5. The compound of claim 1, wherein A is

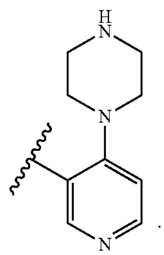 [SMILES: *c1cnccc1N1CCNCC1]

6. The compound of claim 1, wherein A is

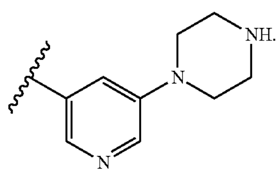 [SMILES: *c1cncc(N2CCNCC2)c1]

7. The compound of claim 1, wherein said compound has the structure:

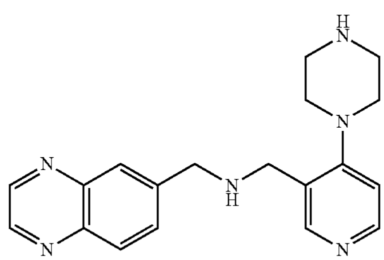

,

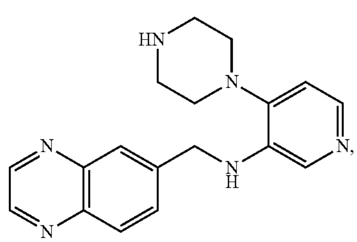

or

-continued

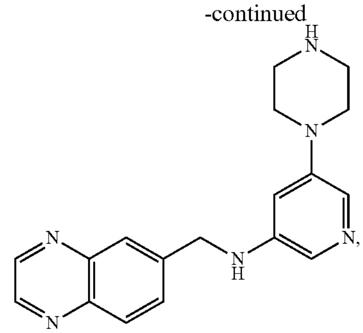

or a pharmaceutically acceptable salt thereof.

8. A composition comprising a therapeutically effective amount of the compound of claim 1 in a pharmaceutically acceptable carrier, diluent, or excipient.

9. The compound of claim 1, wherein q and r are 0 or 1.

10. The compound of claim 1, wherein q and r are 1.

11. The compound of claim 1, wherein q is 1 and r is 0.

12. The compound of claim 1, wherein m is 1.

13. The compound of claim 1, wherein q is 0 and r is 2.

14. The compound of claim 1, wherein Lis

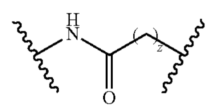

and z is 2.

15. The compound of claim 1, wherein A is

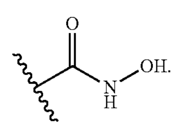 [SMILES: *C(=O)NO]

16. The compound of claim 1, wherein said compound has the structure

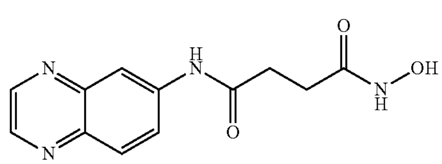

or

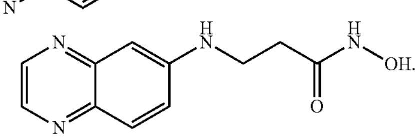

wherein $X_5$ and $X_6$ are independently selected from $CR_3$ and N, and $X_4$ and $X_7$ are $CR_3$, wherein $R_3$ is —H;
m is 1 or 2; and
W is —O or —$NR_4$, wherein $R_4$ is —H;
or a pharmaceutically acceptable salt thereof.

* * * * *

SEQUENCE LISTING

<160> NUMBER OF SEQ ID NOS: 12

<210> SEQ ID NO 1
<211> LENGTH: 200
<212> TYPE: DNA
<213> ORGANISM: Artificial Sequence
<220> FEATURE:
<223> OTHER INFORMATION: structure cassette flanking target sequence

<400> SEQUENCE: 1
gtgggcactt cggtgtccac acgcgaagga aaccgcgtgt caactgtgca acagctgaca 60
aagagattcc taaaactcag tactcggggt gcccttctgc gtgaaggctg agaaataccc 120
gtatcacctg atctggataa tgccagcgta gggaagtgct ggatccggtt cgccggatca 180
atcgggcttc ggtccggttc 200

<210> SEQ ID NO 2
<211> LENGTH: 74
<212> TYPE: DNA
<213> ORGANISM: Artificial Sequence
<220> FEATURE:
<223> OTHER INFORMATION: forward prime sequence

<400> SEQUENCE: 2
gaaattacga ctcactatag gtcgcgagta atcgcgaccg gcgctagaga tagtgccgtg 60
ggcacttcgg tgtc 74

<210> SEQ ID NO 3
<211> LENGTH: 18
<212> TYPE: DNA
<213> ORGANISM: Artificial Sequence
<220> FEATURE:
<223> OTHER INFORMATION: reverse transcription primer

<400> SEQUENCE: 3
cgggcttcgg tccggttc 18

<210> SEQ ID NO 4
<211> LENGTH: 46
<212> TYPE: DNA
<213> ORGANISM: Artificial Sequence
<220> FEATURE:
<223> OTHER INFORMATION: amplicon-specific forward primer
<220> FEATURE:
<221> NAME/KEY: misc_feature
<222> LOCATION: (25)..(29)
<223> OTHER INFORMATION: n is a, c, g, t or u

<400> SEQUENCE: 4
ccctacacga cgctcttccg atctnnnnng gccttcgggc caagga 46

<210> SEQ ID NO 5
<211> LENGTH: 61
<212> TYPE: DNA
<213> ORGANISM: Artificial Sequence
<220> FEATURE:
<223> OTHER INFORMATION: amplicon-specific reverse primer
<220> FEATURE:
<221> NAME/KEY: misc_feature
<222> LOCATION: (33)..(37)
<223> OTHER INFORMATION: n is a, c, g, t or u

<400> SEQUENCE: 5
gactggagtt cagacgtgtg ctcttccgat ctnnnnnttg aaccggaccg aagcccgatt 60
t 61

<210> SEQ ID NO 6
<211> LENGTH: 238
<212> TYPE: DNA
<213> ORGANISM: Artificial Sequence
<220> FEATURE:
<223> OTHER INFORMATION: target sequence

<400> SEQUENCE: 6
ggucgcgagu aaucgcgacc gcugcaagag auuguagcgu gggcacuucg guguccacac 60
gcgaaggaaa ccgcguguca acugugcaac agcugacaaa gagauuccua aaacucagua 120
cucggggugc ccuucugcgu gaaggcugag aaauacccgu aucaccugau cuggauaaug 180
ccagcguagg gaagugcugg auccgguucg ccggaucaau cgggcuucgg uccgguuc 238

<210> SEQ ID NO 7
<211> LENGTH: 20
<212> TYPE: DNA
<213> ORGANISM: Artificial Sequence
<220> FEATURE:
<223> OTHER INFORMATION: portion of structure cassette

<400> SEQUENCE: 7
ggucgcgagu aaucgcgacc 20

<210> SEQ ID NO 8
<211> LENGTH: 18
<212> TYPE: DNA
<213> ORGANISM: Artificial Sequence
<220> FEATURE:
<223> OTHER INFORMATION: RNA barcode

<400> SEQUENCE: 8
gcugcaagag auuguagc 18

<210> SEQ ID NO 9
<211> LENGTH: 20

-continued

<212> TYPE: DNA
<213> ORGANISM: Artificial Sequence
<220> FEATURE:
<223> OTHER INFORMATION: structure cassette

<400> SEQUENCE: 9
gugggcacuu cggguguccac 20

<210> SEQ ID NO 10
<211> LENGTH: 51
<212> TYPE: DNA
<213> ORGANISM: Artificial Sequence
<220> FEATURE:
<223> OTHER INFORMATION: DENV pseudoknot

<400> SEQUENCE: 10
acgcgaagga aaccgcgugu caacugugca acagcugaca aagagauucc u 51

<210> SEQ ID NO 11
<211> LENGTH: 84
<212> TYPE: DNA
<213> ORGANISM: Artificial Sequence
<220> FEATURE:
<223> OTHER INFORMATION: TPP riboswitch

<400> SEQUENCE: 11
caguacucgg ggugcccuuc ugcgugaagg cugagaaaua cccguaucac cugaucugga 60
uaaugccagc guagggaagu gcug 84

<210> SEQ ID NO 12
<211> LENGTH: 39
<212> TYPE: DNA
<213> ORGANISM: Artificial Sequence
<220> FEATURE:
<223> OTHER INFORMATION: structure cassette

<400> SEQUENCE: 12
gauccgguuc gccggaucaa ucgggcuucg guccgguuc 39